US012357684B2

(12) United States Patent
Pushko et al.

(10) Patent No.: US 12,357,684 B2
(45) Date of Patent: *Jul. 15, 2025

(54) MODIFIED RSV F PROTEINS AND METHODS OF THEIR USE

(71) Applicant: Novavax, Inc., Gaithersburg, MD (US)

(72) Inventors: Peter M. Pushko, Frederick, MD (US); Yingyun Wu, Clarksburg, MD (US); Michael J. Massare, Mt. Airy, MD (US); Ye Liu, Clarksville, MD (US); Gale Smith, Germantown, MD (US); Bin Zhou, Clarksburg, MD (US)

( * ) Notice: Subject to any disclaimer, the term of this patent is extended or adjusted under 35 U.S.C. 154(b) by 207 days.

This patent is subject to a terminal disclaimer.

(21) Appl. No.: 17/818,887

(22) Filed: Aug. 10, 2022

(65) Prior Publication Data

US 2023/0293667 A1     Sep. 21, 2023

Related U.S. Application Data

(63) Continuation of application No. 16/599,568, filed on Oct. 11, 2019, now Pat. No. 11,446,374, which is a continuation of application No. 16/009,257, filed on Jun. 15, 2018, now Pat. No. 11,052,146, which is a continuation of application No. 14/839,247, filed on Aug. 28, 2015, now Pat. No. 10,022,437, which is a continuation of application No. 14/221,675, filed on Mar. 21, 2014, now Pat. No. 9,675,685, which is a continuation of application No. 12/633,995, filed on Dec. 9, 2009, now Pat. No. 8,715,692.

(60) Provisional application No. 61/224,787, filed on Jul. 10, 2009, provisional application No. 61/169,077, filed on Apr. 14, 2009, provisional application No. 61/121,126, filed on Dec. 9, 2008.

(51) Int. Cl.

| | | |
|---|---|---|
| *A61K 39/155* | (2006.01) | |
| *A61K 9/00* | (2006.01) | |
| *A61K 9/107* | (2006.01) | |
| *A61K 39/12* | (2006.01) | |
| *A61K 39/39* | (2006.01) | |
| *C07K 14/005* | (2006.01) | |
| *C12N 7/00* | (2006.01) | |
| *A61K 39/00* | (2006.01) | |

(52) U.S. Cl.
CPC .......... *A61K 39/155* (2013.01); *A61K 9/0019* (2013.01); *A61K 9/1075* (2013.01); *A61K 39/12* (2013.01); *A61K 39/39* (2013.01); *C07K 14/005* (2013.01); *C12N 7/00* (2013.01); *A61K 39/00* (2013.01); *A61K 2039/5258* (2013.01); *A61K 2039/54* (2013.01); *A61K 2039/545* (2013.01); *A61K 2039/55* (2013.01); *A61K 2039/55505* (2013.01); *A61K 2039/57* (2013.01); *A61K 2039/575* (2013.01); *C07K 2319/00* (2013.01); *C12N 2760/18522* (2013.01); *C12N 2760/18523* (2013.01); *C12N 2760/18534* (2013.01); *C12N 2760/18562* (2013.01); *C12N 2760/18571* (2013.01)

(58) Field of Classification Search
None
See application file for complete search history.

(56) References Cited

U.S. PATENT DOCUMENTS

| | | |
|---|---|---|
| 5,149,650 A | 9/1992 | Wertz et al. |
| 6,245,532 B1 | 6/2001 | Smith et al. |
| 6,352,697 B1 | 3/2002 | Cox et al. |
| 8,563,002 B2 | 10/2013 | Baudoux et al. |
| 8,715,692 B2 * | 5/2014 | Pushko ................. A61K 39/39 435/325 |
| 9,675,685 B2 * | 6/2017 | Pushko ................. A61P 37/04 |
| 10,022,437 B2 * | 7/2018 | Pushko ................. A61P 31/12 |
| 10,426,829 B2 | 10/2019 | Smith et al. |
| 11,052,146 B2 | 7/2021 | Pushko et al. |
| 11,253,585 B2 | 2/2022 | Smith et al. |
| 11,446,374 B2 * | 9/2022 | Pushko ................. A61K 39/12 |
| 2004/0028698 A1 | 2/2004 | Colau et al. |
| 2005/0142148 A1 | 6/2005 | Fouchier et al. |
| 2008/0233150 A1 | 9/2008 | Smith et al. |
| 2009/0263420 A1 | 10/2009 | Morrison |
| 2010/0239617 A1 | 9/2010 | Pushko et al. |
| 2010/0239671 A1 | 9/2010 | Edelman et al. |
| 2010/0291147 A1 | 11/2010 | Baudoux et al. |
| 2013/0122032 A1 | 5/2013 | Smith et al. |
| 2014/0227309 A1 | 8/2014 | Smith et al. |
| 2014/0294879 A1 | 10/2014 | Pushko et al. |
| 2015/0265698 A1 | 9/2015 | Pushko et al. |

(Continued)

FOREIGN PATENT DOCUMENTS

| | | |
|---|---|---|
| AU | 2003245220 B2 | 1/2004 |
| AU | 2014100888 A4 | 9/2014 |

(Continued)

OTHER PUBLICATIONS

Begona et al. J Gen Virol. 2004, vol. 85, pp. 3677-3687 (Year: 2004).*

(Continued)

*Primary Examiner* — Shanon A. Foley
*Assistant Examiner* — Myron G H

(74) *Attorney, Agent, or Firm* — Carlson, Caspers, Vandenburgh & Lindquist, P.A.

(57) ABSTRACT

The present invention is generally related to modified or mutated respiratory syncytial virus fusion (F) proteins and methods for making and using them, including immunogenic compositions such as vaccines for the treatment and/or prevention of RSV infection.

14 Claims, 25 Drawing Sheets

Specification includes a Sequence Listing.

(56) References Cited

U.S. PATENT DOCUMENTS

| | | |
|---|---|---|
| 2015/0266930 A1 | 9/2015 | Pushko et al. |
| 2015/0306207 A1 | 10/2015 | Smith et al. |
| 2015/0335730 A1 | 11/2015 | Smith et al. |
| 2015/0359872 A1 | 12/2015 | Pushko et al. |
| 2018/0133308 A1 | 5/2018 | Smith et al. |
| 2019/0134187 A1 | 5/2019 | Pushko et al. |
| 2020/0030436 A1 | 1/2020 | Pushko et al. |
| 2020/0101151 A1 | 4/2020 | Smith et al. |
| 2022/0387579 A1 | 12/2022 | Smith et al. |

FOREIGN PATENT DOCUMENTS

| | | |
|---|---|---|
| CN | 101090711 A | 12/2007 |
| CN | 102107003 A | 6/2011 |
| EP | 0109942 A2 | 5/1984 |
| EP | 0180564 B1 | 5/1986 |
| EP | 0242380 B1 | 10/1987 |
| EP | 0362279 B1 | 4/1990 |
| EP | 0436620 B1 | 7/1991 |
| EP | 0889736 B1 | 1/1999 |
| EP | 1539231 B1 | 6/2005 |
| EP | 3718566 A1 | 10/2020 |
| JP | H10508301 A | 8/1998 |
| RU | 2531235 C2 | 10/2014 |
| WO | 8809336 A1 | 12/1988 |
| WO | 9003184 A1 | 4/1990 |
| WO | WO-9100104 A1 | 1/1991 |
| WO | 9611711 A1 | 4/1996 |
| WO | 9730728 A1 | 8/1997 |
| WO | 9836772 A1 | 8/1998 |
| WO | 0035481 A2 | 6/2000 |
| WO | WO-20010066137 A1 | 9/2001 |
| WO | 2004004762 A1 | 1/2004 |
| WO | WO-2005021713 A2 | 3/2005 |
| WO | WO-2005080417 A2 | 9/2005 |
| WO | WO-2007149490 A1 | 12/2007 |
| WO | WO-2008114149 A2 | 9/2008 |
| WO | WO-2008133663 A2 | 11/2008 |
| WO | WO-2009012487 A2 | 1/2009 |
| WO | WO-2009108689 A1 | 9/2009 |
| WO | WO-2010077717 A1 | 7/2010 |
| WO | WO-2010138193 A2 | 12/2010 |
| WO | WO-2011008974 A2 | 1/2011 |
| WO | WO-2012061815 A2 | 5/2012 |
| WO | WO-2013006842 A2 | 1/2013 |
| WO | WO-2013049342 A1 | 4/2013 |
| WO | WO-2014024024 A1 | 2/2014 |
| WO | WO-2014124423 A1 | 8/2014 |
| WO | WO-2014174018 A1 | 10/2014 |

OTHER PUBLICATIONS

Amorij et al., "Development of Stable Influenza Vaccine Powder Formulations: Challenges and Possibilities," Pharmaceutical Research 25(6):1256-1273 (2008).
Anderson et al., "Intracellular processing of the human respiratory syncytial virus fusion glycoprotein: amino acid substitutions affecting folding, transport and cleavage," J. Gen. Virol. 73:1177-118 (1992).
Brandenburg et al., Respiratory Syncytial Virus Specific Serum Antibodies in Infants Under Six Months of Age: Limited Serological Response Upon Infection, J. Med. Virol. 52:97-104 (1997).
Calder et al., "Electron Microscopy of the Human Respiratory Syncytial Virus Fusion Protein and Complexes That It Forms with Monoclonal Antibodies," Virol. 271:122-131 (2000).
Citovsky et al., "Fusion of Sendai Virions or Reconstituted Sendai Virus Envelopes with Liposomes or Erythrocyte Membranes Lacking Virus Receptors," The Journal of Biological Chemistry 260(22)12072-12077 (1985).
Creemers et al., "Endoproteolytic Cleavage of Its Propeptide Is a Prerequisite for Efficient Transport of Furin Out of the Endoplasmic Reticulum," J. Biol. Chem. 270(6):2695-2702 (1995).
Crowe, Jr. et al. "Passively Acquired Antibodies Suppress Humoral But Not Cell-Mediated Immunity in Mice Immunized with Live Attenuated Respiratory Syncytial Virus Vaccines," J. Immunol. 167:3910-3918 (2001).
Crowe, Jr., "Influence of Maternal Antibodies on Neonatal Immunization against Respiratory Viruses," Clin. Infect. Dis. 33:1720-1727 (2001).
Demirjian and Levy, "Safety and Efficacy of Neonatal Vaccination," Eur. J. Immunol. 39(1):36-46 (2009).
Eckert et al., "Mechanisms of Viral Membrane Fusion and Its Inhibition," Annual Review of Biochemistry 70:770-810 (2001).
European Search Report, EP Appl. No. 16166033.7, 8 pages (Aug. 10, 2016).
European Search Report, EP Appl. No. 16843191.4, 13 pages, dated Mar. 14, 2019.
Extended European Search Report issued by the European Patent Office for Application No. 19770704.5, dated Jan. 3, 2022, 10 pages.
Extended European Search Report issued by the European Patent Office for Application No. 20171841.8, dated Aug. 5, 2020, 11 pages.
Genbank Accession No. AAC55970.1, "fusion glycoprotein precursor [Human respiratory syncytial virus]" (1996), 1 page.
Glenn et al., "Safety and immunogenicity of a Sf9 insect cell-derived respiratory syncytial virus fusion protein nanoparticle vaccine," Vaccine. Jan. 7, 2013;31(3):524-532.
Glenn, "Recombinant, Insect Cell-Derived RSV Nanoparticle Vaccine," Novavax.com, 34 pages (Jul. 4, 2012) https://www.novavax.com/download/file/RSV nanoparticle Vaccine-MVADsJuly4(2).pdf.
Gonzalez-Reyes et al., "Cleavage of the human respiratory syncytial virus fusion protein at two distinct sites is required for activation of membrane fusion," Proc. Natl. Acad. Sci. USA 98(17):9859-9864 (2001).
Gruenke et al., "New Insights into the Spring-Loaded Conformational Change of Influenza Virus Hemagglutinin," Journal of Virology, May 2002, 76:(9) 4456-4466 (2002).
Halsey and Galazka, "The efficacy of DPT and oral poliomyelitis immunization schedules initiated from birth to 12 weeks of age," Bull. World Health Org. 63(6):1151-1169 (1985).
Hancock et al., "Adjuvants Recognized by Toll-Like Receptors Inhibit the Induction of Polarized Type 2 T Cell Responses by Natural Attachment (G) Protein of Respiratory Syncytial Virus," Vaccine 21(27-30):4348-4358 (2003).
Higgins et al., "Advances in RSV vaccine research and development—A global agenda," Vaccine 34:2870-2875 (2016).
Idrus, "Novavax Announces Initiation of Ebola Vaccine Phase 1 Clinical Trial Supported by Non-Human Primate Challenge Data and Documented Rapid Manufacturing Capabilities," Fierce Pharma, dated Feb. 17, 2015, 4 pages, retrieved online on Aug. 3, 2022 at : https://www.fiercepharma.com/vaccines/novavax-announces-initiation-of-ebola-vaccine-phase-1-clinical-trial-supported-by-non.
International Search Report, 4 pages, PCT appl. No. PCT/US09/67269 (mailed Mar. 4, 2010).
International Search Report, 5 pages, PCT appl. No. PCT/US2012/057546 (mailed Jan. 22, 2013).
Iyer et al., Purified, Proteolytically Mature HIV Type 1 SOSIP gp140 Envelope Trimers, AIDS Research and Human Retroviruses 23(6):817-828 (2007).
Kim et al., "Respiratory Syncytial Virus Disease in Infants Despite Prioir Administration of Antigenic Inactivated Vaccine," Am. J. Epidemil. 89(4):422-434 (1969).
Lee et al., "Recent Advances of Vaccine Adjuvants for Infectious Diseases ," Immune Network, 51-57 (2015).
Lichtenberg et al., "The Mechanism of Detergent Solubilization of Lipid Bilayers," Biophysical Journal, vol. 105:289-299 (2013).
Lieberman et al., "Preparation and immunogenic properties of a recombinant West Nile subunit vaccine," Vaccine 25:414-423 (2007).
Martin et al., "Sequence elements of the fusion peptide of human respiratory syncytial virus fusion protein required for activity," J. Gen. Virol. 87:1649-1658 (2006).

(56) References Cited

OTHER PUBLICATIONS

Martinez et al., "Combining DNA and protein vaccines for early life immunization against respiratory syncytial virus in mice," Eur. J. Immunol. 29:3390-3400 (1999).
Murphy et al., "An update on approaches to the development of respiratory syncytial virus (RSV) and parainfluenza virus type 3 (PIV3) vaccines," Virus Res. 32:13-26 (1994).
Murphy et al., "Effect of Age and Preexisting Antibody on Serum Antibody Response of Infants and Children to the F and G Glycoproteins during Respiratory Syncytial Virus Infection," J. Clin. Microbiol. 24(5):894-898 (1986).
Murphy et al., "Effect of passive antibody on the immune repspone of cotton rats to purified F and G glycoproteins of repiratory suncytial virus (RSV)," Vaccine 9:185-189 (1991).
Murphy et al., "Passive Transfer of Respiratory Syncytial Virus (RSV) Antiserum Suppresses the Immune Response to the RSV Fusion (F) and Large (G) Glycoproteins Expressed by Recombinant Vacccinia Viruses," J. Virol. 62(10):3907-3910 (1988).
"Novavax NanoFlu Achieves All Primary Endpoints In Phase 3 Clinical Trial," Press Release dated Mar. 24, 2020, 3 pages.
Nussbaum et al., "Fusion of influenza Virus particles with liposomes: requirement for cholesterol and virus receptors to allow fusion with and lysis of neutral but not of negatively charged liposomes",. Journal of General Virology, 2831-2837 (1992).
Parrington et al., "Baculovirus expression of the respiratory syncytial virus fusion protein using Trichoplusia ni insect cells," Virus Genes 14:63-72 (1997).
Rama et al., "An insect cell derived respiratory syncytial virus (RSV) F nanoparticle vaccine induces antigenic site II antibodies and protects against RSV challenge in cotton rats by active and passive immunization", Vaccine, Elsevier, Amsterdam, NL, 32(48)6485-6492 (2014).
Roder, et al., "Purification of respiratory syncytial virus F and G-proteins," Journal of Chromatography B: Biomedical Sciences and Applications 737:97-106 (2000).
Ruiz-Arguello et al., "Effect of Proterlytic Processing at Two Distinct Sites on Shape and Aggregation of an Anchorless Fusion Protein of Human Respiratory Syncytial Virus and Fate of the Intervening Segment," Virol. 298:317-326 (2002).
Ruiz-Arguello et al., "Thermostability of the human respiratory syncytial virus fusion protein before and after activation: implications for the membrane-fusion mechanism," J. Gen. Virol. 85:3677-3687 (2004).
Sales and Wang, "Respiratory syncytial virus vaccine: Is it coming?" Paediatr. Child Health 8(10):605-608 (2003).
Shi et al., "Stabilization of Human Papillomavirus Virus-Like Particles by Non-Ionic Surfactants," Journal of Pharmaceutical Sciences, 2005, p. 1538-1551.
Shinde et al., "Improved Titers Against Influenza Drift Variants with a Nanoparticle Vaccine," N Engl Med 378:24 (2018), 3 pages.
Shinde et al., Induction of Broadly Cross-Reactive Immune Responses Against A(H3N2) Viruses: Results of a Phase 2 Trial of a Novel Recombinant Hemagglutinin Saponin-Adjvanted nanoparticle Influenza Vaccine ("NanoFlu"), 30 pages (2018).
Siegrist et al., "Protective Efficacy against Respiratory Syncytial Virus following Murine Neonatal Immunization with BBG2Na Vaccine: Influence of Adjuvants and Maternal Antibodies," J. Infect. Dis. 179:1326-1333 (1999).
Siegrist, "Mechanisms by which maternal antibodies influence infant vaccine responses: review of hypotheses and definition of main determinants," Vaccine 21:3406-3412 (2003).
Smith et al., "Respiratory Syncytial Virus Fusion Glycoprotein Expressed in Insect Cells Form Protein Nanoparticles That Induce Protective Immunity in Cotton Rats," PLOS ONE 7(11):e50852, 12 pages (2012).
Supplementary European Search Report, EP Appl. No. 09836751.9, 9 pages (Apr. 29, 2013).
Supplementary European Search Report, EP Appl. No.12835033.7, 7 pages (Feb. 17, 2015).

Tekewe et al., A rapid and simple screening method to identify conditions for enhanced stability of modular vaccine candidates, Biochemical Engineering Journal 100:50-58 (2015).
Vaarala et al., "Antigenic Differences between AS03 Adjuvanted Influenza A (H1N1) Pandemic Vaccines: Implications for Pandemrix Associated Narcolepsy Risk ," PLOS One, 1-23 (2014).
Wang et al., "Expression and purification of an influenza hemagglutinin-one step closer to a recombinant protein-based influenza vaccine," Vaccine vol. 24, Issue 12, pp. 2176-2185 (2006).
Wang, "Protein aggregation and its inhibition in biopharmaceutics," International Journal of Pharmaceutics 289 (2005) 1-30.
Wathen et al., Immunization of Cotton Rats with the Human Respiratory Syncytial Virus F Glycoprotein produced using a Baculovirus Vector, The Journal of Infectious Diseases 159(2):255-264 (1989).
Weisshaar et al., "Blocking Respiratory Syncytial Virus Entry: A Story with Twists," DNA Cell Biol. 34:505-510 (2015).
Whitehead et al., "Recombinant Respiratory Syncytial Virus (RSV) Bearing a Set of Mutations from Cold-Passaged RSV is Attenuated in Chimpanzees," J. Virol. 72(5):4467-4471 (1998).
Widjaja et al., "Recombinant Soluble Respiratory Syncytial Virus F Protein That Lacks Heptad Repeat B, Contains a GCN4 Trimerization Motif and Is Not Cleaved Displays Prefusion-Like Characteristics," PLoS One 10(6):e0130829, 19 pages (2015).
Written Opinion of the International Searching Authority, 4 pages, PCT appl. No. PCT/US09/67269 (mailed Mar. 4, 2010).
Written Opinion of the International Searching Authority, 5 pages, PCT appl. No. PCT/US2012/057546 (mailed Jan. 22, 2013).
European Search Report, EP Appl. No. 16166033.7, 10 pages (Aug. 10, 2016).
Bangham et al., Human and Murin Cytotoxic T Cells, J. Immunol 137, pp. 3973-3977 (1986).
Barr, et al., ISCOMS . . . , Advanced Drug Delivery Reviews vol. 32, pp. 247-271 (1998).
Barr, et al., ISCOMS . . . , Immunol. and Cell Biology vol. 74, 19 pgs (1996).
Behboudi et al., Quaillaja Saponin Formulations that Stimulate . . . Scand. J. Immunol. 50, pp. 371-377 (1999).
Boulter, et al., Evaluation of Recombinant Sporozoite . . . , Tropical Medicine and Intl Health vol. 4, pp. A71-A77 (1999).
Claassen, et al., The Iscom Structure . . . , Characteristics and Use of New-Generation Adjuvants, pp. 531-541 (1992).
Copland, et al., Hydration of Lipid Films with an Aqueous Solution of Quil A . . . , Intl J. Pharma. vol. 196, pp. 135-139 (2000).
Coulter, et al., Studies on Experimental Adjuvanted Influenza Vaccines . . . , Vaccine vol. 16, No. 11/12 pp. 1243-1253 (1997).
Cox, et al., Adjuvants—a Classification and Review . . . Vaccine vol. 15, pp. 248-256 (1997).
Cox, et al., Development of an Influenza—ISCOM Vaccine, Vaccine Design, pp. 33-49 (1997).
Cox, et al., Prospects for the Development of New Vaccine Adjuvants, BioDrugs vol. 12, pp. 439-453 (1999).
Demana, et al., A Comparison of Pseudo-Ternary Diagrams . . . , J. of Pharm. and Pharmacology vol. 56, pp. 573-580 (2004).
Dermana, et al., Pseudo-Ternary Phase Diagrams of Aqueous Mixtures of Quil A . . . , Intl J. Pharma. vol. 270, pp. 229-239 (2004).
Ekstrom et al., Iscom and Iscom-Matrix Enhance by Intranasal Route . . . Vaccine 17, pp. 2690-2701 (1999).
Falsey et al., Comparison of the Safety, JID 198, pp. 1317-1326, 2008.
Hu, et al., Immunostimulating Complexes, Advanced Drug Delivery Reviews vol. 51, p. 149-159 (2001).
Johansson et al., Iscoms with Different Quaillaja Saponin Components . . . Vaccine 17, pp. 2894-2900 (1999).
Kensil, et al., Saponins as Vaccine Adjuvants, Critical Reviews in Therapeutic Drug Carrier Systems, pp. 1-55 (1996).
Kersten, et al., On the Structure of Immune-Stimulating Saponin . . . , Biochimica et Biophysica vol. 1062, pp. 165-171 (1991).
Lovgren, et al., The Requirement of Lipids . . . , Biotechnology and Applied Biochemistry vol. 10, pp. 161-172 (1988).
Lovgren-Bengtsson, et al., 4.5 Preparation and Use of Adjuvants, Methods in Microbiology vol. 32, pp. 551-588 (2002).
Lovgren-Bengtsson, et al., 6 Preparation and Use of Adjuvants, Methods in Microbiology vol. 25, pp. 471-502 (1998).

(56) References Cited

OTHER PUBLICATIONS

Morein, et al., Iscom, a novel structure for antigenic presentation . . . , Nature vol. 308, pp. 457-460 (1984).
O'Hagan, et al., Microparticles as Vaccine Adjuvants and Delivery Systems, Expert Rev. Vaccines vol. 2, pp. 269-283 (2003).
Ozel, et al., Quaternary Structure of the Immunostimulating Complex (Iscom), J. Ultrastructure and Molecular Structure Research vol. 102,240-248 (1989).
Ronnberg, et al., Adjuvant Activity of Non-Toxic Quillaja Saponaria . . . , Vaccine vol. 13, No. 14, pp. 1375-1382 (1995).
Sjolander, et al., ISCOMS: An Adjuvant with Multiple Functions, J. Leukocyte Biology vol. 64, pp. 713-723 (1998).
Sjolander, et al., Uptake and Adjuvant Activity . . . Advanced Drug Delivery Reviews vol. 34, pp. 321-338 (1998).

\* cited by examiner

FIGURE 1

RSV F0

Signal Peptide (SP) → | F2 | Fusion Domain (FD) | Transmembrane (TM)
F0 Cleavage Sites (CS) ↑↑     F1

RSV F0 CS

......NNRARR↓ELP....LSKKRKRR↓FLG

Wt F0 — Signal Peptide (SP) | F2 | Cleavage Site (CS) | Fusion Domain (FD) | F1

2° → ...NNRARR ELP...LSKKRKRR ← 1° Cleavage Site

RSV F Wt .....NNRARR ELP...LSKKRKRR FLG....

RSV F 1°CS .....NNRARR ELP...LSKKQKQQ FLG....

- Preserve 3D structure
- Alter the charge
- Prevent cleavage
- Down regulate fusion Arginine (R)
polar - charged Glutamine (Q)
polar - neutral

FIGURE 4

Modified RSV F0 (GeneBank Assession AAB59858): pNVAX 2023 clone

```
MELLILKANA ITTILTAVTF CFASGQNITE EFYQSTCSAV SKGYLSALRT
GWYTSVITIE LSNIKENKCN GTDAKVKLIK QELDKYKNAV TELQLLMQST
PATNNRSKVTHL LPRFMNYTLN NAKKTNVTLS    KVLPLKNYID
        KQLLPIVNKQ EGEVNKIKSA LLSTNKAVVS LSNGVSVLTS LEIT REFSVN AGV TPVSTY
MLTNSELLSL SCSISNIETV INDMPITNDQ KKLMSNNVQI VRQQSYSIMS IIKEEVLAYV
VQLPLYGVID TPCWKLHTSP LCTTNTKEGS NICLTRTDRG WYCINAGSVS
FFPQAETCKV QSNRVFCDTM NSLTLPSEVN LCNVDIFNPK YDCIKIMTSKT
DVSSSVITSL GAIVSCYGKT KCTASNKNRG TIKT FSNGCD YVS KGVDTV
SVGNTLYYVN KQEGKSLYVK GEPIINFYDP LVFPSDEFDA SIS QVNEKIN
QSLAFIRKSD ELLHNVNAGK STTNIMITTI IIVIIVILLS LIAVGLLLYC
KARSTPVTLS KDQLSGINNI AFSN
```

2° Cleavage Site     1° Cleavage Site     Fusion domain

F0 CS Mut 11
pNVAX2033
Baculovirus No. 541

Cryptic Poly(A)  P102A   Fusion   I379V   M447V

F2   KKQKQQ 1°CS   F1

Partial deletion (Δ137-146) of F fusion domain

FIGURE 7

BV #683 Modified RSV F0

F0 CS Mut 11
pNVAX2033
Baculovirus No. 541

Cryptic Poly(A)  P102A  I379V  M447V
F2  FD Δ137-146  F1
KKQKQQ 1°CS

Codon optimized
1° cleavage site inactivation (3 conservative aa changes)
Cryptic poly(A) in F2 removed
3 aa corrections to GenBank sequence
Deletion of N-terminal half of the F1 fusion domain

FIGURE 9

Purified BV #683 RSV F

FIGURE 11

Purified RSV - F #683 micelles (rosettes)

single F0 trimer ~ 20 nm
micelle diameter ~ 40 nm

FIGURE 13

Modified RSF F: BV #622 and #623

| Clone Name | Description | WB/Coomassie | Conclusion |
|---|---|---|---|
| HRSV F0 (541) W/ BRSV F0 CT | HRSV F0 CT replaced by BRSV F0 CT | +++/- | Intracellular level is similar to 541, but inhibit BRSV M when co-infection. VLP yield is not as good as 541 |
| HRSV F0(541)+BRSV M | double genes tandem | F+++, M+++/ F-, M++ | Both intracellular and VLP yield is better than 541 co-infection with BRSV M |
| HRSV F0 (541) W/BRSV F0 CT+BRSV M | double genes tandem | F+++, M+++ F-, M++ | Both intracellular and VLP yield is better than co-infection, inhibition of BRSV M solved |
| HRSV F0 FD(G139K) | introduce G139K Point mutation (G139K) into Fusion domian | ++/- | FD(G139K) doesn't improve F0 expression |
| HRSV F0 FD(G143K) | introduce G143K Point mutation (G139K) into Fusion domian | ++/- | FD(G143K) doesn't improve F0 expression |
| HRSV F0 FD(S150K) | introduce S150K Point mutation (G139K) into Fusion domian | ++/- | FD(S150K) doesn't improve F0 expression |
| HRSV F0 FD(S153K) | introduce S153K Point mutation (G139K) into Fusion domian | ++/- | FD(S153K) doesn't improve F0 expression |
| HRSV F0 FD(S146K) | introduce S146K Point mutation (G139K) into Fusion domian | ++/- | FD(S146K) doesn't improve F0 expression |
| HRSV F0 CS mut | delete 4AA in 1'CS, change 2'CS from RARR to RANN | ++/- | very poor F0 expression |
| HRSV F0 CS mut (622) | F0 Fusion domain partial deletion(10AA) Intact Cleavage Site | ++++/ +++ | excellent F0 intracellular expression, strong band on coomassie gel |
| HRSV F0 CS mut (683) | F0 Fusion domain partial deletion(10AA) Intact Cleavage Site | ++++/ ++++ | excellent F0 intracellular expression, strong band on coomassie gel |

FIGURE 16D

MODIFIED RSV F PROTEINS AND METHODS OF THEIR USE

CROSS-REFERENCE TO RELATED APPLICATIONS

This application is a continuation of U.S. Ser. No. 16/599,568, filed Oct. 11, 2019, which is a continuation of U.S. Ser. No. 16/009,257, filed. Jun. 15, 2018, now U.S. Pat. No. 11,052,146, issued Jul. 6, 2021, which is a continuation of U.S. Ser. No. 14/839,247, filed Aug. 28, 2015, now U.S. Pat. No. 10,022,437, issued Jul. 17, 2018, which is a continuation of U.S. Ser. No. 14/221,675, filed Mar. 21, 2014, now U.S. Pat. No. 9,675,685, issued Jun. 13, 2017, which is a continuation of U.S. Ser. No. 12/633,995, filed Dec. 9, 2009, now U.S. Pat. No. 8,715,692, issued May 6, 2014, which claims priority to U.S. Provisional Application Ser. No. 61/121,126, filed Dec. 9, 2008, U.S. Provisional Application Ser. No. 61/169,077, filed Apr. 14, 2009, and U.S. Provisional Application Ser. No. 61/224,787, filed Jul. 10, 2009, each of which is herein incorporated by reference in its entirety for all purposes.

REFERENCE TO AN ELECTRONIC SEQUENCE LISTING

The contents of the electronic sequence listing (NOVV_034_09US_SeqList_ST26.xml; Size: 62,550 bytes; and Date of Creation: Aug. 4, 2022) is herein incorporated by reference in its entirety.

TECHNICAL FIELD

The present invention is generally related to modified or mutated respiratory syncytial virus fusion (F) proteins and methods for making and using them, including immunogenic compositions such as vaccines for the treatment and/or prevention of RSV infection.

BACKGROUND OF THE INVENTION

Respiratory syncytial virus (RSV) is a member of the genus *Pneumovirus* of the family Paromyxaviridae. Human RSV (HRSV) is the leading cause of severe lower respiratory tract disease in young children and is responsible for considerable morbidity and mortality in humans. RSV is also recognized as an important agent of disease in immunocompromised adults and in the elderly. Due to incomplete resistance to RSV in the infected host after a natural infection, RSV may infect multiple times during childhood and adult life.

This virus has a genome comprised of a single strand negative-sense RNA, which is tightly associated with viral protein to form the nucleocapsid. The viral envelope is composed of a plasma membrane derived lipid bilayer that contains virally encoded structural proteins. A viral polymerase is packaged with the virion and transcribes genomic RNA into mRNA, The RSV genome encodes three transmembrane structural proteins, F, G, and SH, two matrix proteins, M and M2, three nucleocapsid proteins N, P, and L, and two nonstructural proteins, NS1 and NS2.

Fusion of HRSV and cell membranes is thought to occur at the cell surface and is a necessary step for the transfer of viral ribonucleoprotein into the cell cytoplasm during the early stages of infection. This process is mediated by the fusion (F) protein, which also promotes fusion of the membrane of infected cells with that of adjacent cells to form a characteristic syncytia, which is both a prominent cytopathic effect and an additional mechanism of viral spread. Accordingly, neutralization of fusion activity is important in host immunity. Indeed, monoclonal antibodies developed against the F protein have been shown to neutralize virus infectivity and inhibit membrane fusion (Calder et al., 2000, *Virology* 271: 122-131).

The F protein of RSV shares structural features and limited, but significant amino acid sequence identity with F glycoproteins of other paramyxoviruses. It is synthesized as an inactive precursor of 574 amino acids (F0) that is cotranslationally glycosylated on asparagines in the endoplasmic reticulum, where it assembles into homo-oligomers. Before reaching the cell surface, the F0 precursor is cleaved by a protease into F2 from the N terminus and F1 from the C terminus. The F2 and F1 chains remains covalently linked by one or more disulfide bonds.

Immunoaffinity purified full-length F proteins have been found to accumulate in the form of micelles (also characterized as rosettes), similar to those observed with other full-length virus membrane glycoproteins (Wrigley et 1986, in *Electron Microscopy of Proteins*, Vol 5, p. 103-163, Academic Press, London). Under electron microscopy, the molecules in the rosettes appear either as inverted cone-shaped rods (~70%) or lollipop-shaped (~30%) structures with their wider ends projecting away from the centers of the rosettes. The rod conformational state is associated with an F glycoprotein in the pre-fusion inactivate state while the lollipop conformational state is associated with an F glycoprotein in the post-fusion, active state.

Electron micrography can be used to distinguish between the prelusion and postfusion (alternatively designated prefusogenic and fusogenic) conformations, as demonstrated by Calder et al., 2000. *Virology* 271:122-131. The prefusion conformation can also be distinguished from the fusogenic (postfusion) conformation by liposome association assays. Additionally, prefusion and fusogenic conformations can be distinguished using antibodies (e.g., monoclonal antibodies) that specifically recognize conformation epitopes present on one or the other of the prefusion or fusogenic form of the RSV F protein, but not on the other form. Such conformation epitopes can be due to preferential exposure of an antigenic determinant on the surface of the molecule. Alternatively, conformational epitopes can arise from the juxtaposition of amino acids that are non-contiguous in the linear polypeptide.

It has been shown previously that the F precursor is cleaved at two sites (site 1, after residue 109 and site 11, after residue 136), both preceded by motifs recognized by furin-like proteases. Site 11 is adjacent to a fusion peptide, and cleavage of the F protein at both sites is needed for membrane fusion (Gonzalez-Reyes et al., 2001, *PNAS* 98(17): 9859-9864). When cleavage is completed at both sites, it is believed that there is a transition from cone-shaped to lollipop-shaped rods.

SUMMARY OF THE INVENTION

As described herein, the present inventors have found that surprisingly high levels of expression of the fusion (F) protein can be achieved when certain modifications are made to the structure of the RSV F protein. Such modifications also unexpectedly reduce the cellular toxicity of the RSV F protein in a host cell. In addition, the modified F proteins of the present invention demonstrate an improved ability to exhibit the post-fusion "lollipop" morphology as opposed to the pre-fusion "rod" morphology. Thus, in one aspect, the modified F proteins of the present invention can also exhibit improved immunogenicity as compared to wild-type F proteins. These modifications have significant applications to the development of vaccines and methods of using said vaccines for the treatment and/or prevention of RSV. The present invention provides recombinant RSV F proteins that demonstrate increased expression, reduced cellular toxicity, and/or enhanced immunogenic properties as compared to wild-type RSV F proteins.

In one aspect, the invention provides recombinant RSV F proteins comprising modified or mutated amino acid sequences as compared to wild-type RSV F proteins. In general, these modifications or mutations increase the expression, reduce the cellular toxicity, and/or enhance the immunogenic properties of the RSV F proteins as compared to wild-type RSV F proteins. In certain exemplary embodiments, the RSV F proteins are human RSV F proteins.

The RSV F protein preferably comprises a modified or mutated amino acid sequence as compared to the wild-type RSV F protein (e.g. as exemplified in SEQ ID NO: 2). In one embodiment, the RSV F protein contains a modification or mutation at the amino acid corresponding to position P102 of the wild-type RSV F protein (SEQ ID NO: 2). In another embodiment, the RSV F protein contains a modification or mutation at the amino acid corresponding to position I379 of the wild-type RSV F protein (SEQ ID NO: 2). In another embodiment, the RSV F protein contains a modification or mutation at the amino acid corresponding to position M447 of the wild-type RSV F protein (SEQ ID NO: 2).

In one embodiment, the RSV F protein contains two or more modifications or mutations at the amino acids corresponding to the positions described above. In another embodiment, the RSV F protein contains three modifications or mutations at the amino acids corresponding to the positions described above.

In one specific embodiment, the invention is directed to RSV F proteins wherein the proline at position 102 is replaced with alanine. In another specific embodiment, the invention is directed to RSV F proteins wherein the isoleucine at position 379 is replaced with valine. In yet another specific embodiment, the invention is directed to RSV F proteins wherein the methionine at position 447 is replaced with valine. In certain embodiments, the RSV F protein contains two or more modifications or mutations at the amino acids corresponding to the positions described in these specific embodiments. In certain other embodiments, the RSV F protein contains three modifications or mutations at the amino acids corresponding to the positions described in these specific embodiments. In an exemplary embodiment, the RSV protein has the amino acid sequence described in SEQ ID NO: 4.

In one embodiment, the coding sequence of the RSV F protein is further optimized to enhance its expression in a suitable host cell. In one embodiment, the host cell is an insect cell. In an exemplary embodiment, the insect cell is an Sf9 cell.

In one embodiment, the coding sequence of the codon optimized RSV F gene is SEQ ID NO: 3. In another embodiment, the codon optimized RSV F protein has the amino acid sequence described in SEQ ID NO: 4.

In one embodiment, the RSV F protein further comprises at least one modification in the cryptic poly(A) site of F2. In another embodiment, the RSV F protein further comprises one or more amino acid mutations at the primary cleavage site (CS). In one embodiment, the RSV F protein contains a modification or mutation at the amino acid corresponding to position R133 of the wild-type RSV F protein (SEQ ID NO: 2) or the codon optimized RSV F protein (SEQ NO: 4). In another embodiment, the RSV F protein contains a modification or imitation at the amino acid corresponding to position R135 of the wild-type RSV F protein (SEQ ID NO: 2) or the codon optimized RSV F protein (SEQ ID NO: 4). In yet another embodiment, the RSV F protein contains a modification or mutation at the amino acid corresponding to position 8136 of the wild-type RSV F protein (SEQ 11) NO: 2) or the codon optimized RSV F protein (SEQ ID NO: 4).

In one specific embodiment, the invention is directed to RSV F proteins wherein the arginine at position 133 is replaced with glutamine. In another specific embodiment, the invention is directed to RSV F proteins wherein the arginine at position 135 is replaced with glutamine. In yet another specific embodiment, the invention is directed to RSV F proteins wherein arginine at position 136 is replaced with glutamine. In certain embodiments, the RSV F protein contains two or more modifications or mutations at the amino acids corresponding to the positions described in these specific embodiments. In certain other embodiment, the RSV F protein contains three modifications or mutations at the amino acids corresponding to the positions described in these specific embodiments. In an exemplary embodiment, the RSV protein has the amino acid sequence described in SEQ ID NO: 6.

In another embodiment, the RSV F protein further comprises a deletion in the N-terminal half of the fusion domain corresponding to amino acids 137-146 of SEQ ID NO: 2, SEQ ID NO: 4, and SEQ ID NO: 6. In an exemplary embodiment, the RSV F protein has the amino acid sequence described in SEQ ID NO: 8. In an alternative embodiment, the RSV F protein has the amino acid sequence described in SEQ 11) NO: 10.

Further included within the scope of the invention are RSV F proteins, other than human RSV F protein (SEQ ID NO: 2), which contain alterations corresponding to those set out above. Such RSV F proteins may include, but are not limited to, the RSV F proteins from A strains of human RSV, B strains of human RSV, strains of bovine RSV, and strains of avian RSV.

In some embodiments, the invention is directed to modified or mutated RSV F proteins that demonstrate increased expression in a host cell as compared to wild-type RSV F proteins, such as the one shown by SEQ ID NO: 2. In other embodiments, the invention is directed to modified or mutated RSV F proteins that demonstrate reduced cellular toxicity in a host cell as compared to wild-type RSV F proteins, such as the one shown by SEQ ID NO: 2. In yet other embodiments, the invention is directed to modified or mutated RSV F proteins that demonstrate enhanced immunogenic properties as compared to wild-type RSV F proteins, such as the one shown by SEQ ID NO: 2.

In additional aspects, the invention provides immunogenic compositions comprising one or more modified or mutated RSV F proteins as described herein. In one embodiment, the invention provides a micelle comprised of one or more modified or mutated RSV F proteins (e.g. an RSV F micelle).

In another embodiment, the present invention provides a virus-like particle (VLP) comprising a modified or mutated RSV F protein. In some embodiments, the VLP further comprises one or more additional proteins.

In one embodiment, the VLP further comprises a matrix (M) protein. In one embodiment, the M protein is derived from a human strain of RSV. In another embodiment, the M protein is derived from a bovine strain of RSV. In other embodiments, the matrix protein may be an M1 protein from an influenza virus strain. In one embodiment, the influenza virus strain is an avian influenza virus strain. In other embodiments, the M protein may be derived from a Newcastle Disease Virus (NDV) strain.

In additional embodiments, the VLP further comprises the RSV glycoprotein G. In another embodiment, the VLP further comprises the RSV glycoprotein SH. In yet another embodiment, the VLP further comprises the RSV nucleocapsid N protein.

The modified or mutated RSV F proteins may be used for the prevention and/or treatment of RSV infection. Thus, in another aspect, the invention provides a method for eliciting an immune response against RSV. The method involves administering an immunologically effective amount of a composition containing a modified or mutated RSV F protein to a subject, such as a human or animal subject.

In another aspect, the present invention provides pharmaceutically acceptable vaccine compositions comprising a modified or mutated RSV F protein, an RSV F micelle comprising a modified or mutated RSV F protein, or a VLP comprising a modified or mutated RSV F protein.

In one embodiment, the invention comprises an immunogenic formulation comprising at least one effective dose of a modified or mutated RSV F protein. In another embodiment, the invention comprises an immunogenic formulation comprising at least one effective dose of an RSV F micelle comprising a modified or mutated RSV F protein. In yet another embodiment, the invention comprises an immunogenic formulation comprising at least one effective dose of a VLP comprising a modified or mutated RSV F protein.

In another embodiment, the invention provides for a pharmaceutical pack or kit comprising one or more containers filled with one or more of the ingredients of the vaccine formulations of the invention.

In another embodiment, the invention provides a method of formulating a vaccine or antigenic composition that induces immunity to an infection or at least one disease symptom thereof to a mammal, comprising adding to the formulation an effective dose of a modified or mutated RSV F protein, an RSV F micelle comprising a modified or mutated RSV F protein, or a VLP comprising a modified or mutated RSV F protein. In a preferred embodiment, the infection is an RSV infection.

The modified or mutated RSV F proteins of the invention are useful for preparing compositions that stimulate an immune response that confers immunity or substantial immunity to infectious agents. Thus, in one embodiment, the invention provides a method of inducing immunity to infections or at least one disease symptom thereof in a subject, comprising administering at least one effective dose of a modified or mutated RSV F protein, an RSV F micelle comprising a modified or mutated RSV F protein, or a VLP comprising a modified or mutated RSV F protein.

In yet another aspect, the invention provides a method of inducing substantial immunity to RSV virus infection or at least one disease symptom in a subject, comprising administering at least one effective dose of a modified or mutated RSV F protein, an RSV F micelle comprising a modified or mutated RSV F protein, or a VLP comprising a modified or mutated RSV F protein.

Compositions of the invention can induce substantial immunity in a vertebrate (e.g. a human) when administered to the vertebrate. Thus, in one embodiment, the invention provides a method of inducing substantial immunity to RSV virus infection or at least one disease symptom in a subject, comprising administering at least one effective dose of a modified or mutated RSV F protein, an RSV F micelle comprising a modified or mutated RSV F protein, or a VLP comprising a modified or mutated RSV F protein. In another embodiment, the invention provides a method of vaccinating a mammal against RSV comprising administering to the mammal a protection-inducing amount of a modified or mutated RSV F protein, an RSV F micelle comprising a modified or mutated RSV F protein, or a VLP comprising a modified or mutated RSV F protein.

In another embodiment, the invention comprises a method of inducing a protective antibody response to an infection or at least one symptom thereof in a subject, comprising administering at least one effective dose of a modified or mutated RSV F protein, an RSV F micelle comprising a modified or mutated RSV F protein, or a VLP comprising a modified or mutated RSV F protein.

In another embodiment, the invention comprises a method of inducing a protective cellular response to RSV infection or at least one disease symptom in a subject, comprising administering at least one effective dose of a modified or mutated RSV F protein. In another embodiment, the invention comprises a method of inducing a protective cellular response to RSV infection or at least one disease symptom in a subject, comprising administering at least one effective dose of an RSV F micelle comprising a modified or mutated. RSV F protein. In yet another embodiment, the invention comprises a method of inducing a protective cellular response to RSV infection or at least one disease symptom in a subject, comprising administering at least one effective dose of a VLP, wherein the VLP comprises a modified or mutated RSV F protein.

In yet another aspect, the invention provides an isolated nucleic acid encoding a modified or mutated RSV F protein of the invention. In an exemplary embodiment, the isolated nucleic acid encoding a modified or mutated RSV F protein is selected from the group consisting of SEQ ID NO: 3, SEQ ID NO: 5, SEQ ID NO: 7, or SEQ ID NO: 9.

In yet another aspect, the invention provides an isolated cell comprising a nucleic acid encoding a modified or mutated RSV F protein of the invention. In an exemplary embodiment, the isolated nucleic acid encoding a modified or mutated RSV F protein is selected from the group consisting of SEQ ID NO: 3, SEQ ID NO: 5, SEQ ID NO: 7, or SEQ ID NO: 9.

In yet another aspect, the invention provides a vector comprising a nucleic acid encoding a modified or mutated RSV F protein of the invention. In an exemplary embodiment, the isolated nucleic acid encoding a modified or mutated RSV F protein is selected from the group consisting of SEQ ID NO: 3, SEQ ID NO: 5, SEQ ID NO: 7, or SEQ ID NO: 9. In one embodiment, the vector is a baculovirus vector.

In yet another aspect, the invention provides a method of making a RSV F protein, comprising (a) transforming a host cell to express a nucleic acid encoding a modified or mutated RSV F protein of the invention; and (b) culturing said host cell under conditions conducive to the production of said RSV F protein. In one embodiment, the nucleic acid encoding a modified or mutated RSV F protein is selected from the group consisting of SEQ ID NO: 3, SEQ ID NO: 5, SEQ ID NO: 7, or SEQ ID NO: 9. In another embodiment, the host cell is an insect cell. In a further embodiment, the host cell is an is an insect cell transfected with a baculovirus vector comprising a modified or mutated RSV F protein of the invention.

In yet another aspect, the invention provides a method of making a RSV F protein micelle, comprising (a) transforming a host cell to express a nucleic acid encoding a modified or mutated RSV F protein of the invention; and (b) culturing said host cell under conditions conducive to the production of said RSV F protein micelle. In one embodiment, the nucleic acid encoding a modified or mutated RSV F protein is selected from the group consisting of SEQ ID NO: 3, SEQ ID NO: 5. SEQ ID NO: 7, or SEQ ID NO: 9. In one embodiment, the host cell is an insect cell. In an exemplary embodiment, the host cell is an is an insect cell transfected with a baculovirus vector comprising a modified or mutated RSV F protein of the invention.

BRIEF DESCRIPTION OF THE FIGURES

FIG. 1 depicts structure of wild type HRSV $F_0$ protein comprising the cleavage site regions NNRARRELP (SEQ ID NO:30) and LSKKRKRRFLG (SEQ ID NO:31).

FIG. 3 depicts conservative substitutions (R133Q, R135Q and R136Q) in the primary cleavage site of modified HRSV F protein BV #541 (SEQ ID NO: 6). The mutated cleavage site region is shown as LSKKQKQQFLG (SEQ ID NO:35).

FIG. 4 depicts sequence and structure of modified. HRSV F protein BV #541 (SEQ ID NO: 6), and the sequence of the KKQKQQ cleavage site (SEQ ID NO:28).

FIG. 7 depicts structure of modified HRSV F protein BV #683, and the KKQKQQ cleavage site (SEQ ID NO: 28).

FIG. 9 depicts SDS-PAGE coomassie-stained gel (on the left) and Western Blot (on the right) analysis of purified recombinant HRSV F protein BV #683 with or without the presence of βME.

FIG. 11 depicts images of purified recombinant HRSV F protein BV #683 micelles (rosettes) taken in negative stain electron microscopy.

FIG. 13 depicts SDS-PAGE coomassie-stained gel (on the left) and Western. Blot (on the right) analysis of modified HRSV F proteins BV #622 and BV #623 (SEQ ID NO: 21) with or without co-expression with HRSV N and BRSV M proteins in the crude cell culture harvests (intracellular) or pelleted samples by 30% sucrose gradient separation, and structures of BV #622 and BV #623. Also featured is the KKRKRR cleavage site (SEQ ID NO:24)

FIG. 14 depicts SDS-PAGE coomassie-stained gel (on the left) and Western Blot (on the right) analysis of modified HRSV F protein BV #622, double tandem chimeric BV #636 (BV #541+BRSV M), BV #683, BV #684 (BV #541 with YIAL L-domain), and BV #685 (BV #541 with YKKL L-domain) with or without co-expression with HRSV N and BRSV M proteins in the crude cell culture harvests (intracellular) samples, and structure of each analyzed modified HRSV F protein. Also featured is the KKQKQQ cleavage site (SEQ ID NO:28), and the KKRKRR cleavage site (SEQ ID NO:24).

Figure 16B:
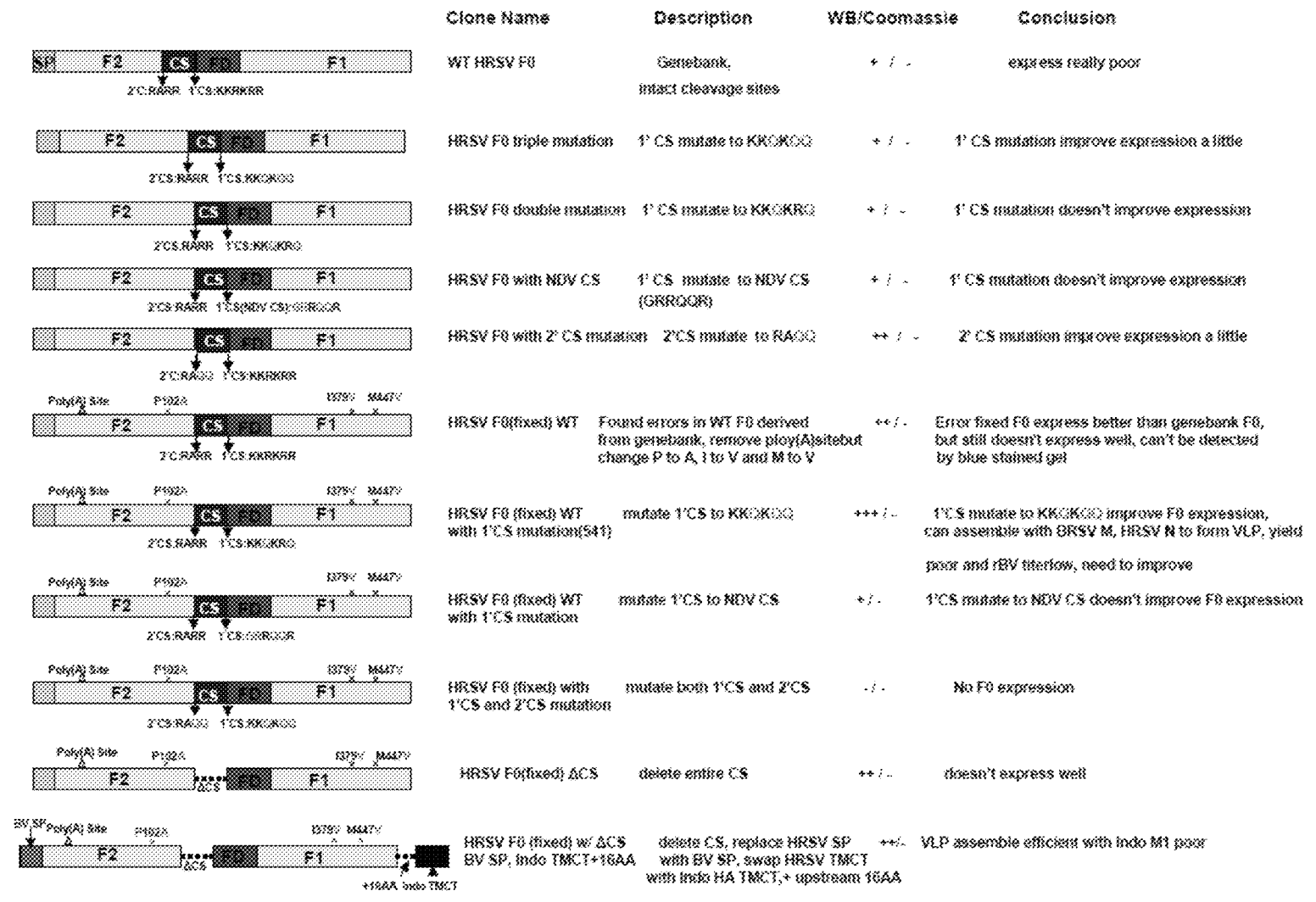
Figure 16D:
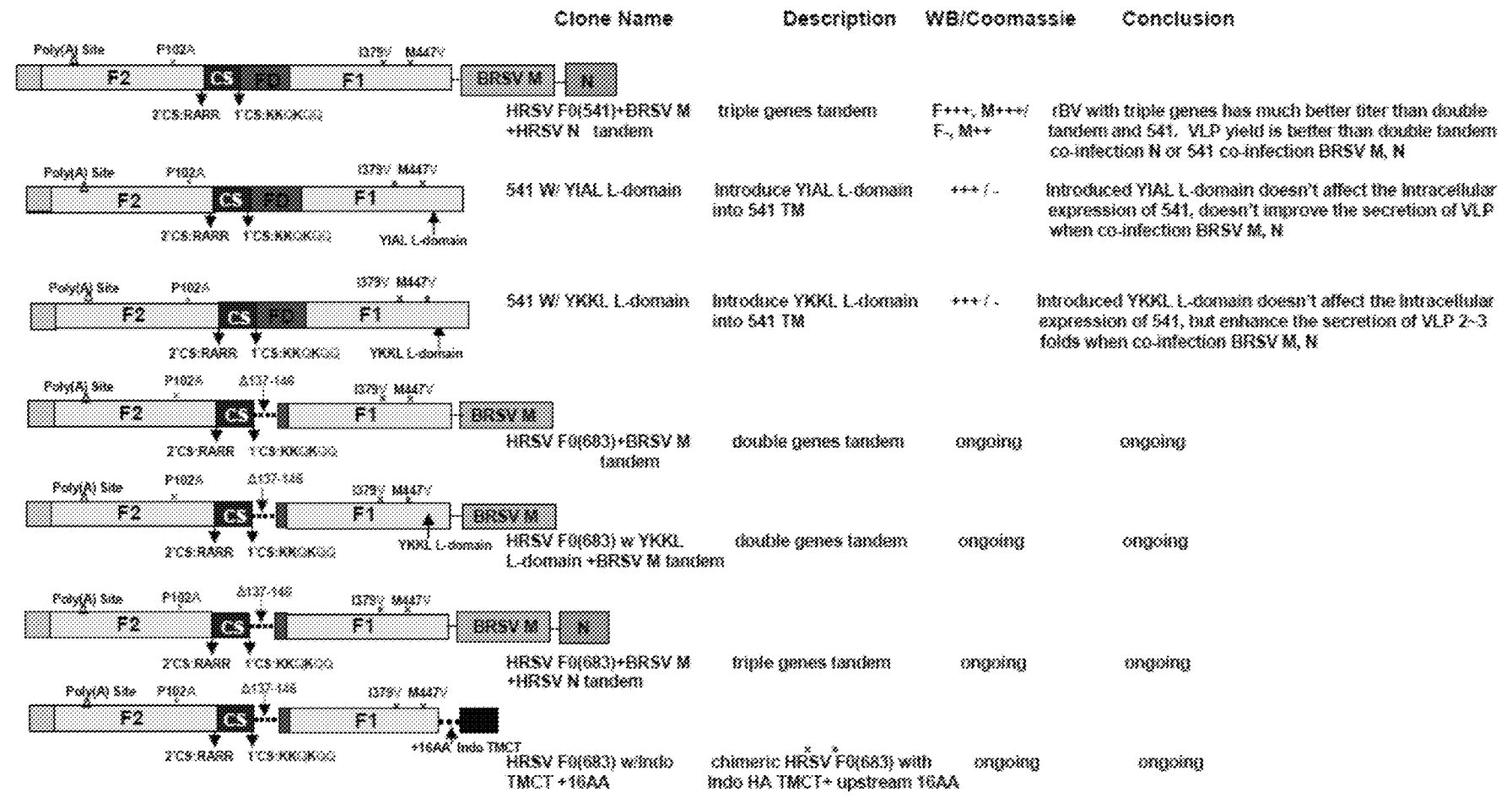

FIGS. 16A-16D depict structure, clone name, description, Western Blot and SDS-PAGE coomassie results, and conclusion for each modified RSV F protein as described in Example 9. Also featured are the KKQKQQ (SEQ ID NO:28), GRRQQR (SEQ ID NO:29), RANN (SEQ ID NO:34), RARR (SEQ NO:23), and KKRKRR (SEQ ID NO:24) cleavage site sequences.

DETAILED DESCRIPTION

Definitions

Figure 2:
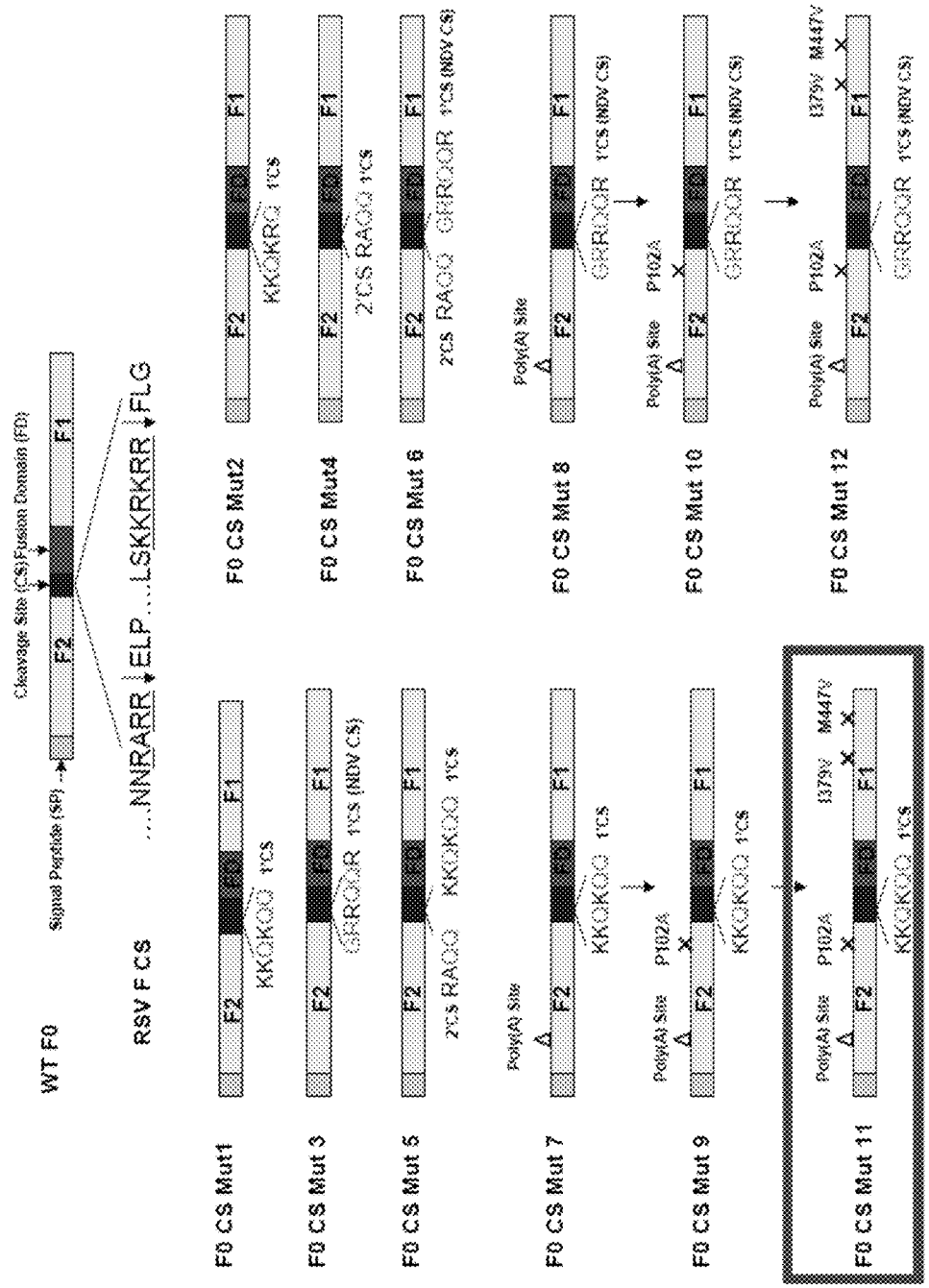
FIG. 2 depicts structures of modified RSV $F_0$ proteins with cleavage site mutations as described in Example 3. The cleavage site regions are shown as NNRARRELP (SEQ NO:30) and LSKKRKRRFLG (SEQ ID NO:31). Particular cleavage site sequences are shown as KKQKQQ (SEQ ID NO:28), GRRQQR (SEQ ID NO:29), KKQKRQ (SEQ ID NO:32), RAQQ (SEQ ID NO:33), and RANK (SEQ ID NO:34).

As used herein the term "adjuvant" refers to a compound that, when used in combination with a specific immunogen (e.g. a modified or mutated RSV F protein, an RSV F micelle comprising a modified or mutated RSV F protein, or a VLP comprising a modified or mutated RSV F protein) in a formulation, will augment or otherwise alter or modify the resultant immune response. Modification of the immune response includes intensification or broadening the specificity of either or both antibody and cellular immune responses.

Modification of the immune response can also mean decreasing or suppressing certain antigen-specific immune responses.

As use herein, the term "antigenic formulation" or "antigenic composition" refers to a preparation which, when administered to a vertebrate, especially a bird or a mammal, will induce an immune response.

As used herein the term "avian influenza virus" refers to influenza viruses found chiefly in birds but that can also infect humans or other animals. In some instances, avian influenza viruses may be transmitted or spread from one human to another. An avian influenza virus that infects humans has the potential to cause an influenza pandemic, i.e., morbidity and/or mortality in humans. A pandemic occurs when a new strain of influenza virus (a virus in which human have no natural immunity, emerges, spreading beyond individual localities, possibly around the globe, and infecting many humans at once.

As used herein an "effective dose" generally refers to that amount of a modified or mutated RSV F protein, an RSV F micelle comprising a modified or mutated RSV F protein, or a VLP comprising a modified or mutated RSV F protein of the invention sufficient to induce immunity, to prevent and/or ameliorate an infection or to reduce at least one symptom of an infection or disease, and/or to enhance the efficacy of another dose of a modified or mutated RSV F protein, an RSV F micelle comprising a modified or mutated RSV F protein, or a VLP comprising a modified or mutated RSV F protein. An effective dose may refer to the amount of a modified or mutated RSV F protein, an RSV F micelle comprising a modified or mutated RSV F protein, or a VLP comprising a modified or mutated RSV F protein sufficient to delay or minimize the onset of an infection or disease. An effective dose may also refer to the amount of a modified or mutated RSV F protein, an RSV F micelle comprising a modified or mutated RSV F protein, or a VLP comprising a modified or mutated RSV F protein that provides a therapeutic benefit in the treatment or management of an infection or disease. Further, an effective dose is the amount with respect to a modified or mutated RSV F protein, an RSV F micelle comprising a modified or mutated RSV F protein, or a VLP comprising a modified or mutated RSV F protein of the invention alone, or in combination with other therapies, that provides a therapeutic benefit in the treatment or management of an infection or disease. An effective dose may also be the amount sufficient to enhance a subject's (e.g., a human's) own immune response against a subsequent exposure to an infectious agent or disease. Levels of immunity can be monitored, e.g., by measuring amounts of neutralizing secretory and/or serum antibodies, e.g., by plaque neutralization, complement fixation, enzyme-linked immunosorbent, or microneutralization assay, or by measuring cellular responses, such as, but not limited to cytotoxic T cells, antigen presenting cells, helper T cells, dendritic cells and/or other cellular responses. T cell responses can be monitored, e.g., by measuring, for example, the amount of $CD4^+$ and $CD8^+$ cells present using specific markers by fluorescent flow cytometry or T cell assays, such as hut not limited to T-cell proliferation assay, T-cell cytotoxic assay, TETRAMER assay, and/or ELISPOT assay. In the case of a vaccine, an "effective dose" is one that prevents disease and/or reduces the severity of symptoms.

As used herein, the term "effective amount" refers to an amount of a modified or mutated RSV F protein, an RSV F micelle comprising a modified or mutated RSV F protein, or a VLP comprising a modified or mutated RSV F protein necessary or sufficient to realize a desired biologic effect. An effective amount of the composition would be the amount that achieves a selected result, and such an amount could be determined as a matter of routine experimentation by a person skilled in the art. For example, an effective amount for preventing, treating and/or ameliorating an infection could be that amount necessary to cause activation of the immune system, resulting in the development of an antigen specific immune response upon exposure to a modified or mutated RSV F protein, an RSV F micelle comprising a modified or mutated RSV F protein, or a VLP comprising a modified or mutated RSV F protein of the invention. The term is also synonymous with "sufficient amount."

As used herein, the term "expression" refers to the process by which polynucleic acids are transcribed into mRNA and translated into peptides, polypeptides, or proteins. If the polynucleic acid is derived from genomic DNA, expression may, if an appropriate eukaryotic host cell or organism is selected, include splicing of the mRNA. In the context of the present invention, the term also encompasses the yield of RSV F gene mRNA and RSV F proteins achieved following expression thereof.

As used herein, the term "F protein" or "Fusion protein" or "F protein polypeptide" or "Fusion protein polypeptide" refers to a polypeptide or protein having all or part of an amino acid sequence of an RSV Fusion protein polypeptide. Similarly, the term "G protein" or "G protein polypeptide" refers to a polypeptide or protein having all or part of an amino acid sequence of an RSV Attachment protein polypeptide. Numerous RSV Fusion and Attachment proteins have been described and are known to those of skill in the art. WO/2008/114149, which is herein incorporated by reference in its entirety, sets out exemplary F and G protein variants (for example, naturally occurring variants As used herein, the terms "immunogens" or "antigens" refer to substances such as proteins, peptides, peptides, nucleic acids that are capable of eliciting an immune response. Both terms also encompass epitopes, and are used interchangeably.

As used herein the term "immune stimulator" refers to a compound that enhances an immune response via the body's own chemical messengers (cytokines). These molecules comprise various cytokines, lymphokines and chemokines with immunostimulatory, immunopotentiating, and pro-inflammatory activities, such as interferons (IFN-γ), interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immune stimulator molecules can be administered in the same formulation as VLPs of the invention, or can be administered separately. Either the protein or an expression vector encoding the protein can be administered to produce an immunostimulatory effect.

As use herein, the term "immunogenic formulation" refers to a preparation which, when administered to a vertebrate, e.g. a mammal, will induce an immune response.

As use herein, the term "infectious agent" refers to microorganisms that cause an infection in a vertebrate. Usually, the organisms are viruses, bacteria, parasites, protozoa and/or fungi.

As used herein, the terms "mutated," "modified," "mutation," or "modification" indicate any modification of a nucleic acid and/or polypeptide which results in an altered nucleic acid or polypeptide. Mutations include, for example, point mutations, deletions, or insertions of single or multiple residues in a polynucleotide, which includes alterations arising within a protein-encoding region of a gene as well as alterations in regions outside of a protein-encoding sequence, such as, but not limited to, regulatory or promoter sequences. A genetic alteration may be a mutation of any type. For instance, the mutation may constitute a point mutation, a frame-shift mutation, an insertion, or a deletion of part or all of a gene. In some embodiments, the mutations are naturally-occurring. In other embodiments, the mutations are the results of artificial mutation pressure. In still other embodiments, the mutations in the RSV F proteins are the result of genetic engineering.

As used herein, the term "multivalent" refers to compositions which have one or more antigenic proteins/peptides or immunogens against multiple types or strains of infectious agents or diseases.

As used herein, the term "pharmaceutically acceptable vaccine" refers to a formulation which contains a modified or mutated RSV F protein, an RSV F micelle comprising a modified or mutated RSV F protein, or a VLP comprising a modified or mutated RSV F protein of the present invention, which is in a form that is capable of being administered to a vertebrate and which induces a protective immune response sufficient to induce immunity to prevent and/or ameliorate an infection or disease, and/or to reduce at least one symptom of an infection or disease, and/or to enhance the efficacy of another dose of a modified or mutated RSV F protein, an RSV F micelle comprising a modified or mutated RSV F protein, or a VLP comprising a modified or mutated RSV F protein. Typically, the vaccine comprises a conventional saline or buffered aqueous solution medium in which the composition of the present invention is suspended or dissolved. In this form, the composition of the present invention can be used conveniently to prevent, ameliorate, or otherwise treat an infection. Upon introduction into a host, the vaccine is able to provoke an immune response including, but not limited to, the production of antibodies and/or cytokines and/or the activation of cytotoxic T cells, antigen presenting cells, helper T cells, dendritic cells and/or other cellular responses.

As used herein, the phrase "protective immune response" or "protective response" refers to an immune response mediated by antibodies against an infectious agent or disease, which is exhibited by a vertebrate (e.g., a human), that prevents or ameliorates an infection or reduces at least one disease symptom thereof. Modified or mutated RSV F proteins, RSV F micelles comprising a modified or mutated RSV F protein, or VLPs comprising a modified or mutated RSV F protein of the invention can stimulate the production of antibodies that, for example, neutralize infectious agents, blocks infectious agents from entering cells, blocks replication of the infectious agents, and/or protect host cells from infection and destruction. The term can also refer to an immune response that is mediated by T-lymphocytes and/or other white blood cells against an infectious agent or disease; exhibited by a vertebrate a human), that prevents or ameliorates infection or disease, or reduces at least one symptom thereof.

As use herein, the term "vertebrate" or "subject" or "patient" refers to any member of the subphylum cordata, including, without limitation, humans and other primates, including non-human primates such as chimpanzees and other apes and monkey species. Farm animals such as cattle, sheep, pigs, goats and horses; domestic mammals such as dogs and cats; laboratory animals including rodents such as mice, rats (including cotton rats) and guinea pigs; birds, including domestic, wild and game birds such as chickens, turkeys and other gallinaceous birds, ducks, geese, and the like are also non-limiting examples. The terms "mammals" and "animals" are included in this definition. Both adult and newborn individuals are intended to be covered. In particular, infants and young children are appropriate subjects or patients for a RSV vaccine.

As used herein, the term "virus-like particle" (VLP) refers to a structure that in al least one attribute resembles a virus but which has not been demonstrated to be infectious. Virus-like particles in accordance with the invention do not carry genetic information encoding for the proteins of the virus-like particles. In general, virus-like particles lack a viral genome and, therefore, are noninfectious. In addition, virus-like particles can often be produced in large quantities by heterologous expression and can be easily purified.

As used herein, the term "chimeric VLP" refers to VLPs that contain proteins, or portions thereof, from at least two different infectious agents (heterologous proteins). Usually, one of the proteins is derived from a virus that can drive the formation of VLPs from host cells. Examples, for illustrative purposes, are the BRSV M protein and/or the HRSV G or F proteins. The terms RSV VLPs and chimeric VLPs can be used interchangeably where appropriate.

As used herein, the term "vaccine" refers to a preparation of dead or weakened pathogens, or of derived antigenic determinants that is used to induce formation of antibodies or immunity against the pathogen. A vaccine is given to provide immunity to the disease, for example, influenza, which is caused by influenza viruses. In addition, the term "vaccine" also refers to a suspension or solution of an immunogen (e.g. a modified or mutated RSV F protein, an RSV F micelle comprising a modified or mutated RSV F protein, or a VLP comprising a modified or mutated RSV F protein) that is administered to a vertebrate to produce protective immunity, i.e., immunity that prevents or reduces the severity of disease associated with infection. The present invention provides for vaccine compositions that are immunogenic and may provide protection against a disease associated with infection.

RSV F Proteins

Two structural membrane proteins, F and G proteins, are expressed on the surface of RSV, and have been shown to be targets of neutralizing antibodies (Sullender, W., 2000, *Clinical Microbiology Review* 13, 1-15). These two proteins are also primarily responsible for viral recognition and entry into target cells; G protein binds to a specific cellular receptor and the F protein promotes fusion of the virus with the cell. The F protein is also expressed on the surface of infected cells and is responsible for subsequent fusion with other cells leading to syncytia formation. Thus, antibodies to the F protein can neutralize virus or block entry of the virus into the cell or prevent syncytia formation. Although antigenic and structural differences between A and B subtypes have been described for both the G and F proteins, the more significant antigenic differences reside on the G protein, where amino acid sequences are only 53% homologous and antigenic relatedness is 5% (Walsh et al. (1987) J. Infect. Dis. 155, 1198-1204; and Johnson et at, (1987) Proc. Natl. Acad. Sci. USA 84, 5625-5629). Conversely, antibodies raised to the F protein show a high degree of cross-reactivity among subtype A and B viruses.

The RSV F protein directs penetration of RSV by fusion between the virion's envelope protein and the host cell plasma membrane. Later in infection, the F protein expressed on the cell surface can mediate fusion with neighboring cells to form syncytia. The F protein is a type I transmembrane surface protein that has a N-terminal cleaved signal peptide and a membrane anchor near the C-terminus. RSV F is synthesized as an inactive $F_0$ precursor that assembles into a homotrimer and is activated by cleavage in the trans-Golgi complex by a cellular endoprotease to yield two disulfide-linked subunits, $F_1$ and $F_2$ subunits. The N-terminus of the $F_1$ subunit that is created by cleavage contains a hydrophobic domain (the fusion peptide) that inserts directly into the target membrane to initiate fusion. The $F_1$ subunit also contains heptad repeats that associate during fusion, driving a conformational shift that brings the viral and cellular membranes into close proximity (Collins and Crowe, 2007, Fields Virology, $5^{th}$ ed., D. M Kipe et al., Lipincott, Williams and Wilkons, p. 1604). SEQ ID NO: 2 (GenBank Accession No. AAB59858) depicts a representative RSV F protein, which is encoded by the gene shown in SEQ ID NO: 1 (GenBank Accession No. M11486).

In nature, the RSV F protein is expressed as a single polypeptide precursor, 574 amino acids in length, designated FO. In vivo, FO oligomerizes in the endoplasmic reticulum and is proteolytically processed by a furin protease at two conserved furin consensus sequences (furin cleavage sites), RARR (SEQ ID NO: 23) (secondary) and KKRKRR (SEQ ID NO: 24) (primary) to generate an oligomer consisting of two disulfide-linked fragments. The smaller of these fragments is termed F2 and originates from the N-terminal portion of the FO precursor. It will be recognized by those of skill in the art that the abbreviations FO, F1 and F2 are commonly designated $F_0$, $F_1$ and $F_2$ in the scientific literature. The larger, C-terminal F1 fragment anchors the F protein in the membrane via a sequence of hydrophobic amino acids, which are adjacent to a 24 amino acid cytoplasmic tail. Three F2-F1 dimers associate to form a mature F protein, which adopts a metastable prefusogenic ("prefusion") conformation that is triggered to undergo a conformational change upon contact with a target cell membrane. This conformational change exposes a hydrophobic sequence, known as the fusion peptide, which associates with the host cell membrane and promotes fusion of the membrane of the virus, or an infected cell, with the target cell membrane.

The F1 fragment contains at least two heptad repeat domains, designated HRA and HRB, and is situated in proximity to the fusion peptide and transmembrane anchor domains, respectively. In the prefusion conformation, the F2-F1 dimer forms a globular head and stalk structure, in which the HRA domains are in a segmented (extended) conformation in the globular head. In contrast, the HRB domains form a three-stranded coiled coil stalk extending from the head region. During transition from the prefusion to the postfusion confirmations, the HRA domains collapse and are brought into proximity to the HRB domains to form an anti-parallel six helix bundle. In the postfusion state the fusion peptide and transmembrane domains are juxtaposed to facilitate membrane fusion.

Although the conformational description provided above is based on molecular modeling of crystallographic data, the structural distinctions between the prefusion and postfusion conformations can be monitored without resort to crystallography. For example, electron micrography can be used to distinguish between the prefusion and postfusion (alternatively designated prefusogenic and fusogenic) conformations, as demonstrated by et al., *Virology,* 271:122-131 (2000) and Morton et al., *Virology,* 311: 275-288, which are incorporated herein by reference for the purpose of their technological teachings. The prefusion conformation can also be distinguished from the fusogenic (post-fusion) conformation by liposome association assays as described by Connolly et al, *Proc. Natl. Acad. Set. USA,* 103:17903-17908 (2006), which is also incorporated herein by reference for the purpose of its technological teachings. Additionally, prefusion and fusogenic conformations can be distinguished using antibodies (e.g., monoclonal antibodies) that specifically recognize conformation epitopes present on one or the other of the prefusion or fusogenic form of the RSV F protein, but not on the other form. Such conformation epitopes can be due to preferential exposure of an antigenic determinant on the surface of the molecule. Alternatively, conformational epitopes can arise from the juxtaposition of amino acids that are non-contiguous in the linear polypeptide.

Modified or Mutated RSV F Proteins

The present inventors have found that surprisingly high levels of expression of the fusion (F) protein can be achieved when specific modifications are made to the structure of the RSV F protein. Such modifications also unexpectedly reduce the cellular toxicity of the RSV F protein in a host cell. In addition, the modified F proteins of the present invention demonstrate an improved ability to exhibit the post-fusion "lollipop" morphology as opposed to the prefusion "rod" morphology. Thus, in one aspect, the modified F proteins of the present invention can also exhibit improved (e.g. enhanced) immunogenicity as compared to wild-type F proteins (e.g. exemplified by SEQ ID NO: 2, which corresponds to GenBank Accession No. AAB59858). These modifications have significant applications to the development of vaccines and methods of using said vaccines for the treatment and/or prevention of RSV.

In accordance with the invention, any number of mutations can be made to native or wild-type RSV F proteins, and in a preferred aspect, multiple mutations can be made to result in improved expression and/or immunogenic properties as compared to native or wild-type RSV F proteins. Such mutations include point mutations, frame shift mutations, deletions, and insertions, with one or more (e.g., one, two, three, or four, etc.) mutations preferred.

The native F protein polypeptide can be selected from any F protein of an RSV A strain, RSV B strain, HRSV A strain, HRSV B strain, BRSV strain, or avian RSV strain, or from variants thereof (as defined above). In certain exemplary embodiments, the native F protein polypeptide is the F protein represented by SEQ ID NO: 2 (GenBank Accession No AAB59858). To facilitate understanding of this disclosure, all amino acid residue positions, regardless of strain, are given with respect to (that is, the amino acid residue position corresponds to) the amino acid position of the exemplary F protein. Comparable amino acid positions of the F protein from other RSV strains can be determined easily by those of ordinary skill in the art by aligning the amino acid sequences of the selected RSV strain with that of the exemplary sequence using readily available and well-known alignment algorithms (such as BLAST, e.g., using default parameters). Numerous additional examples of F protein polypeptides from different RSV strains are disclosed in WO/2008/114149 (which is incorporated herein by reference in its entirety). Additional variants can arise through genetic drift, or can be produced artificially using site directed or random mutagenesis, or by recombination of two or more preexisting variants. Such additional variants are also suitable in the context of the modified or mutated RSV F proteins disclosed herein.

Mutations may be introduced into the RSV F proteins of the present invention using any methodology known to those skilled in the art. Mutations may be introduced randomly by, for example, conducting a PCR reaction in the presence of manganese as a divalent metal ion cofactor. Alternatively, oligonucleotide directed mutagenesis may be used to create the mutant or modified RSV F proteins which allows for all possible classes of base pair changes at any determined site along the encoding DNA molecule. In general, this technique involves annealing an oligonucleotide complementary (except for one or more mismatches) to a single stranded nucleotide sequence coding for the RSV F protein of interest. The mismatched oligonucleotide is then extended by DNA polymerase, generating a double-stranded DNA molecule which contains the desired change in sequence in one strand. The changes in sequence can, for example, result in the deletion, substitution, or insertion of an amino acid. The double-stranded polynucleotide can then be inserted into an appropriate expression vector, and a mutant or modified polypeptide can thus be produced. The above-described oligonucleotide directed mutagenesis can, for example, be carried out via PCR.

Additional RSV Proteins

The invention also encompasses RSV virus-like particles (VLPs) comprising a modified or mutated RSV F protein that can be formulated into vaccines or antigenic formulations for protecting vertebrates (e.g. humans) against RSV infection or at least one disease symptom thereof. In some embodiments, the VLP comprising a modified or mutated RSV F protein further comprises additional RSV proteins, such as M, N, G, and SH. In other embodiments, the VLP comprising a modified or mutated RSV F protein further comprises proteins from heterologous strains of virus, such as influenza virus proteins HA, NA, and M1. In one embodiment, the influenza virus protein M1 is derived from an avian influenza virus strain.

RSV N protein binds tightly to both genomic RNA and the replicative intermediate anti-genomic RNA to form RNAse resistant nucleocapsid. SEQ ID NOs: 16 (wild-type) and 18 (codon-optimized) depict representative amino acid sequences of the RSV N protein and SEQ ID NOs: 15 (wild-type) and 17 (codon-optimized) depict representative nucleic acid sequences encoding the RSV N protein. Encompassed in this invention are RSV N proteins that are at least about 20%, about 30%, about 40%, about 50%, about 60%, about 70% or about 80%, about 85%, about 90%, about 95%, about 96%, about 97%, about 98% or about 99% identical to SEQ ID NO: 18, and all fragments and variants (including chimeric proteins) thereof.

RSV M protein is a non-glycosylated internal virion protein that accumulates in the plasma membrane that interacts with RSV F protein and other factors during virus morphogenesis. In certain preferred embodiments, the RSV M protein is a bovine RSV (BRSV) M protein. SEQ ID NOs: 12 (wild-type) and 14 (codon-optimized) depict representative amino acid sequences of the BRSV M protein and SEQ ID NOs: 11 (wild-type) and 13 (codon-optimized) depict representative nucleic acid sequences encoding the BRSV M protein. Encompassed in this invention are RSV (including, but not limited to, BRSV) M proteins that are at least about 20%, about 30%, about 40%, about 50%, about 60%, about 70% or about 80%, about 85%, about 90%, about 95%, about 96%, about 97%, about 98% or about 99% identical to SEQ ID NOs: 12 and 14, and all fragments and variants (including chimeric proteins) thereof.

RSV G protein is a type II transmembrane glycoprotein with a single hydrophobic region near the N-terminal end that serves as both an uncleaved signal peptide and a membrane anchor, leaving the C-terminal two-thirds of the molecule oriented externally. RSV G is also expressed as a secreted protein that arises from translational initiation at the second AUG in the ORF (at about amino acid 48), which lies within the signal/anchor. Most of the ectodomain of RSV G is highly divergent between RSV strains (Id., p. 1607). SEQ ID NO: 26 depicts a representative RSV G protein, which is encoded by the gene sequence shown in SEQ FD NO: 25. Encompassed in this invention are RSV G proteins that are at least about 20%, about 30%, about 40%, about 50%, about 60%, about 70% or about 80%, about 85%, about 90%, about 95%, about 96%, about 97%, about 98% or about 99% identical to SEQ ID NO: 26, and all fragments and variants (including chimeric proteins) thereof.

The SH protein of RSV is a type II transmembrane protein that contains 64 (RSV subgroup A) or 65 amino acid residues (RSV subgroup B). Some studies have suggested that the RSV SH protein may have a role in viral fusion or in changing membrane permeability. However, RSV lacking the SH gene are viable, cause syncytia formation and grow as well as the wild-type virus, indicating that the SH protein is not necessary for virus entry into host cells or syncytia formation. The SH protein of RSV has shown the ability of inhibit TNF-α signaling. SEQ ID NO: 27 depicts a representative amino acid sequence of the RSV SH protein. Encompassed in this invention are RSV SH proteins that are at least about 20%, about 30%, about 40%, about 50%, about 60%, about 70% or about 80%, about 85%, about 90%, about 95%, about 96%, about 97%, about 98% or about 99% identical to SEQ ID NO: 27, and all fragments and variants (including chimeric proteins) thereof.

RSV Vaccines

Currently, the only approved approach to prophylaxis of RSV disease is passive immunization. Initial evidence suggesting a protective role for IgG was obtained from observations involving maternal antibody in ferrets (Prince, G. A., Ph.D. diss., University of California, Los Angeles, 1975) and humans (Lambrecht et al., (1976) J. Infect. Dis. 134, 211-217; and Glezen et al. (1981) J. Pediatr, 98, 708-715). Hemming et al. (Morell et al., eds., 1986, Clinical Use of Intravenous Immunoglobulins, Academic Press, London at pages 285-294) recognized the possible utility of RSV antibody in treatment or prevention of RSV infection during studies involving the pharmacokinetics of an intravenous immunoglobulin (IVIG) in newborns suspected of having neonatal sepsis. They noted that one infant, whose respiratory secretions yielded RSV, recovered rapidly after IVIG infusion. Subsequent analysis of the IVIG lot revealed an unusually high titer of RSV neutralizing antibody. This same group of investigators then examined the ability of hyperimmune serum or immunoglobulin, enriched for RSV neutralizing antibody, to protect cotton rats and primates against RSV infection (Prince et al. (1985) Virus Res. 3, 193-206; Prince et al. (1990) J. Virol. 64, 3091-3092. Results of these studies suggested that RSV neutralizing antibody given prophylactically inhibited respiratory tract replication of RSV in cotton rats. When given therapeutically, RSV antibody reduced pulmonary viral replication both in cotton rats and in a nonhuman primate model. Furthermore, passive infusion of immune serum or immune globulin did not produce enhanced pulmonary pathology in cotton rats subsequently challenged with RSV.

Since RSV infection can be prevented by providing neutralizing antibodies to a vertebrate, a vaccine comprising a modified or mutated RSV F protein may induce, when administered to a vertebrate, neutralizing antibodies in vivo. The modified or mutated RSV F proteins are favorably used for the prevention and/or treatment of RSV infection. Thus, another aspect of this disclosure concerns a method for eliciting an immune response against RSV. The method involves administering an immunologically effective amount of a composition containing a modified or mutated RSV F protein to a subject (such as a human or animal subject). Administration of an immunologically effective amount of the composition elicits an immune response specific for epitopes present on the modified or mutated RSV F protein. Such an immune response can include B cell responses (e.g., the production of neutralizing antibodies) and/or T cell responses (e.g., the production of cytokines). Preferably, the immune response elicited by the modified or mutated RSV F protein includes elements that are specific for at least one conformational epitope present on the modified or mutated RSV F protein. In one embodiment, the immune response is specific for an epitope present on an RSV F protein found in the "lollipop" post-fusion active state. The RSV F proteins and compositions can be administered to a subject without enhancing viral disease following contact with RSV. Preferably, the modified or mutated RSV F proteins disclosed herein and suitably formulated immunogenic compositions elicit a Th1 biased immune response that reduces or prevents infection with a RSV and/or reduces or prevents a pathological response following infection with a RSV.

In one embodiment, the RSV F proteins of the present invention are found in the form of micelles (e.g. rosettes). The micelles obtainable in accordance with the invention consist of aggregates of the immunogenically active F spike proteins having a rosette-like structure. The rosettes are visible in the electron microscope (Calder et cal., 2000. *Virology* 271: 122-131). Preferably, the micelles of the present invention comprising modified or mutated RSV F proteins exhibit the "lollipop" morphology indicative of the post-fusion active state. In one embodiment, the micelles are purified following expression in a host cell. When administered to a subject, the micelles of the present invention preferably induce neutralizing antibodies. In some embodiments, the micelles may be administered with an adjuvant. In other embodiments, the micelles may be administered without an adjuvant.

In another embodiment, the invention encompasses RSV virus-like particles (VLPs) comprising a modified or mutated RSV F protein that can be formulated into vaccines or antigenic formulations for protecting vertebrates (e.g. humans) against RSV infection or at least one disease symptom thereof. The present invention also relates to RSV VLPs and vectors comprising wild-type and mutated RSV genes or a combination thereof derived from different strains of RSV virus, which when transfected into host cells, will produce virus like particles (VLPs) comprising RSV proteins.

In some embodiments, RSV virus-like particles may further comprise at least one viral matrix protein (e.g. an RSV M protein). In one embodiment, the M protein is derived from a human strain of RSV. In another embodiment, the M protein is derived from a bovine strain of RSV. In other embodiments, the matrix protein may be an M1 protein from a strain of influenza virus. In one embodiment, the strain of influenza virus is an avian influenza strain. In a preferred embodiment, the avian influenza strain is the H5N1 strain A/Indonesia/5/05. In other embodiments, the matrix protein may be from Newcastle Disease Virus (NDV).

In some embodiments, the VLPs may further comprise an RSV G protein. In one embodiment, the G protein may be from HRSV group A. In another embodiment, the G protein may be from HRSV group B. In yet another embodiment, the RSV G may be derived from HRSV group A and/or group B.

In some embodiments, the VLPs may further comprise an RSV SH protein. In one embodiment, the SH protein may be from HRSV group A. In another embodiment, the SH protein may be from HRSV group B. In yet another embodiment, the RSV SH may be derived from HRSV group A and/or group B.

In some embodiments, VLPs may further comprise an RSV N protein. In one embodiment, the N protein may be from HRSV group A. In another embodiment, the N protein may be from HRSV group B. In yet another embodiment, the RSV N may be derived from HRSV group A and/or group B.

In further embodiments, VLPs of the invention may comprise one or more heterologous immunogens, such as influenza hemagglutinin (HA) and/or neuraminidase (NA).

In some embodiments, the invention also comprises combinations of different RSV M, F, N, SH, and/or G proteins from the same and/or different strains in one or more VLPs. In addition, the VLPs can include one or more additional molecules for the enhancement of an immune response.

In another embodiment of the invention, the RSV VLPs can carry agents such as nucleic acids, siRNA, micro-RNA, chemotherapeutic agents, imaging agents, and/or other agents that need to be delivered to a patient.

VLPs of the invention are useful for preparing vaccines and immunogenic compositions. One important feature of VLPs is the ability to express surface proteins of interest so that the immune system of a vertebrate induces an immune response against the protein of interest. However, not all proteins can be expressed on the surface of VLPs. There may be many reasons why certain proteins are not expressed, or be poorly expressed, on the surface of VLPs. One reason is that the protein is not directed to the membrane of a host cell or that the protein does not have a transmembrane domain. As an example, sequences near the carboxyl terminus of influenza hemagglutinin may be important for incorporation of HA into the lipid Mayer of the mature influenza enveloped nucleocapsids and for the assembly of HA trimer interaction with the influenza matrix protein M1 (Ali, et at., (2000) J. Virol. 74, 8709-19).

Thus, one embodiment of the invention comprises chimeric VLPs comprising a modified or mutated F protein from RSV and at least one immunogen which is not normally efficiently expressed on the cell surface or is not a normal RSV protein. In one embodiment, the modified or mutated RSV F protein may be fused with an immunogen of interest. In another embodiment, the modified or mutated RSV F protein associates with the immunogen via the transmembrane domain and cytoplasmic tail of a heterologous viral surface membrane protein, e.g., MMTV envelope protein.

Other chimeric VLPs of the invention comprise VLPs comprising a modified or mutated RSV F protein and at least one protein from a heterologous infectious agent. Examples of heterologous infectious agent include but are not limited to a virus, a bacterium, a protozoan, a fungi and/or a parasite. In one embodiment, the immunogen from another infectious agent is a heterologous viral protein. In another embodiment, the protein from a heterologous infectious agent is an envelope-associated protein. In another embodiment, the protein from another heterologous infectious agent is expressed on the surface of VLPs. In another embodiment, the protein from an infectious agent comprises an epitope that will generate a protective immune response in a vertebrate. In one embodiment, the protein from another infectious agent is co-expressed with a modified or mutated RSV F protein. In another embodiment, the protein from another infectious agent is fused to a modified or mutated RSV F protein. In another embodiment, only a portion of a protein from another infectious agent is fused to a modified or mutated RSV F protein. In another embodiment, only a portion of a protein from another infectious agent is fused to a portion of a modified or mutated RSV F protein. In another embodiment, the portion of the protein from another infectious agent fused to modified or mutated RSV F protein is expressed on the surface of VLPs.

The invention also encompasses variants of the proteins expressed on or in the VLPs of the invention. The variants may contain alterations in the amino acid sequences of the constituent proteins. The term "variant" with respect to a protein refers to an amino acid sequence that is altered by one or more amino acids with respect to a reference sequence. The variant can have "conservative" changes, wherein a substituted amino acid has similar structural or chemical properties, e.g., replacement of leucine with isoleucine. Alternatively, a variant can have "nonconservative" changes, e.g., replacement of a glycine with a tryptophan. Analogous minor variations can also include amino acid deletion or insertion, or both. Guidance in determining which amino acid residues can be substituted, inserted, or deleted without eliminating biological or immunological activity can be found using computer programs well known in the art, for example, DNASTAR software.

Natural variants can occur due to mutations in the proteins. These mutations may lead to antigenic variability within individual groups of infectious agents, for example influenza. Thus, a person infected with, for example, an influenza strain develops antibody against that virus, as newer virus strains appear, the antibodies against the older strains no longer recognize the newer virus and re-infection can occur. The invention encompasses all antigenic and genetic variability of proteins from infectious agents for making VLPs.

General texts which describe molecular biological techniques, which are applicable to the present invention, such as cloning, mutation, cell culture and the like, include Berger and Kimmel, Guide to Molecular Cloning Techniques, Methods in Enzymology volume 152 Academic Press, Inc., San Diego, Calif. (Berger) Sambrook et al., Molecular Cloning—A Laboratory Manual (3rd Ed.), Vol. 1-3, Cold Spring Harbor Laboratory, Cold Spring Harbor, N.Y., 2000 ("Sambrook") and Current Protocols in Molecular Biology, F. M. Ausubel et al., eds., Current Protocols, a joint venture between Greene Publishing Associates, Inc. and John Wiley & Sons, Inc., ("Ausubel"). These texts describe mutagenesis, the use of vectors, promoters and many other relevant topics related to, e.g., the cloning and mutating and/or G molecules of RSV, etc. Thus, the invention also encompasses using known methods of protein engineering and recombinant DNA technology to improve or alter the characteristics of the proteins expressed on or in the VLPs of the invention. Various types of mutagenesis can be used to produce and/or isolate variant nucleic acids that encode for protein molecules and/or to further modify/mutate the proteins in or on the VLPs of the invention. They include but are not limited to site-directed, random point mutagenesis, homologous recombination (DNA shuffling), mutagenesis using uracil containing templates, oligonucleotide-directed mutagenesis, phosphorothioate-modified DNA mutagenesis, mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like.

The invention further comprises protein variants which show substantial biological activity, e.g., able to elicit an effective antibody response when expressed on or in VLPs of the invention. Such variants include deletions, insertions, inversions, repeats, and substitutions selected according to general rules known in the art so as have little effect on activity.

Methods of cloning the proteins are known in the art. For example, the gene encoding a specific RSV protein can be isolated by RT-PCR from polyadenylated mRNA extracted from cells which had been infected with a RSV virus. The resulting product gene can be cloned as a DNA insert into a vector. The term "vector" refers to the means by which a nucleic acid can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. In many, but not all, common embodiments, the vectors of the present invention are plasmids or bacmids.

Thus, the invention comprises nucleotides that encode proteins, including chimeric molecules, cloned into an expression vector that can be expressed in a cell that induces the formation of VLPs of the invention. An "expression vector" is a vector, such as a plasmid that is capable of promoting expression, as well as replication of a nucleic acid incorporated therein. Typically, the nucleic acid to be expressed is "operably linked" to a promoter and/or enhancer, and is subject to transcription regulatory control by the promoter and/or enhancer. In one embodiment, the nucleotides encode for a modified or mutated RSV F protein (as discussed above). In another embodiment, the vector further comprises nucleotides that encode the M and/or G RSV proteins. In another embodiment, the vector further comprises nucleotides that encode the M and/or N RSV proteins. In another embodiment, the vector further comprises nucleotides that encode the M, G and/or N RSV proteins. In another embodiment, the vector further comprises nucleotides that encode a BRSV M protein and/or N RSV proteins. In another embodiment, the vector further comprises nucleotides that encode a BRSV M and/or G protein, or influenza HA and/or NA protein. In another embodiment, the nucleotides encode a modified or mutated RSV F and/or RSV G protein with an influenza HA and/or NA protein. In another embodiment, the expression vector is a baculovirus vector.

In some embodiments of the invention, proteins may comprise mutations containing alterations which produce silent substitutions, additions, or deletions, but do not alter the properties or activities of the encoded protein or how the proteins are made. Nucleotide variants can be produced for a variety of reasons, e.g., to optimize codon expression for a particular host (change codons in the human mRNA to those preferred by insect cells such as Sf9 cells. See U.S.

Patent Publication 2005/0118191, herein incorporated by reference in its entirely for all purposes.

In addition, the nucleotides can be sequenced to ensure that the correct coding regions were cloned and do not contain any unwanted mutations. The nucleotides can be subcloned into an expression vector (e.g. baculovirus) for expression in any cell. The above is only one example of how the RSV viral proteins can be cloned. A person with skill in the art understands that additional methods are available and are possible.

The invention also provides for constructs and/or vectors that comprise RSV nucleotides that encode for RSV structural genes, including F, M, G, N, SH, or portions thereof, and/or any chimeric molecule described above. The vector may be, for example, a phage, plasmid, viral, or retro-viral vector. The constructs and/or vectors that comprise RSV structural genes, including F, M, G, N, SH, or portions thereof, and/or any chimeric molecule described above, should be operatively linked to an appropriate promoter, such as the AcMNPV polyhedrin promoter (or other baculovirus), phage lambda PL promoter, the *E. coli* lac, phoA and tac promoters, the SV40 early and late promoters, and promoters of retroviral LTRs are non-limiting examples. Other suitable promoters will be known to the skilled artisan depending on the host cell and/or the rate of expression desired. The expression constructs will further contain sites for transcription initiation, termination, and, in the transcribed region, a ribosome-binding site for translation. The coding portion of the transcripts expressed by the constructs will preferably include a translation initiating codon at the beginning and a termination codon appropriately positioned at the end of the polypeptide to be translated.

Expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Among vectors preferred are virus vectors, such as baculovirus, poxvirus (e.g., vaccinia virus, avipox virus, canarypox virus, fowlpox virus, raccoonpox virus, swinepox virus, etc.), adenovirus (e.g., canine adenovirus), herpesvirus, and retrovirus. Other vectors that can be used with the invention comprise vectors for use in bacteria, which comprise pQE70, pQE60 and pQE-9, pBluescript vectors, Phagescript vectors, pNH8A, pNH16a, pNH18A, pNH46A, ptrc99a, pKK223-3, pKK233-3, pDR540, pRIT5. Among preferred eukaryotic vectors are pFastBac1 pWINEO, pSV2CAT, pOG44, pXT1 and pSG, pSVK3, pBPV, pMSG, and pSVL. Other suitable vectors will be readily apparent to the skilled artisan. In one embodiment, the vector that comprises nucleotides encoding for RSV genes, including modified or mutated RSV F genes, as well as genes for M, G, N, SH or portions thereof, and/or any chimeric molecule described above, is pFastBac.

The recombinant constructs mentioned above could be used to transfect, infect, or transform and can express RSV proteins, including a modified or mutated RSV F protein and at least one immunogen. In one embodiment, the recombinant construct comprises a modified or mutated RSV F, M, G, N, SH, or portions thereof, and/or any molecule described above, into eukaryotic cells and/or prokaryotic cells. Thus, the invention provides for host cells which comprise a vector (or vectors) that contain nucleic acids which code for RSV structural genes, including a modified or mutated RSV F; and at least one immunogen such as but not limited to RSV G, N, and SH, or portions thereof, and/or any molecule described above, and permit the expression of genes, including RSV F, G, N, M, or SH or portions thereof, and/or any molecule described above in the host cell under conditions which allow the formation of VLPs.

Among eukaryotic host cells are yeast, insect, avian, plant, *C. elegans* (or nematode) and mammalian host cells. Non limiting examples of insect cells are, *Spodoptera frugiperda* (Sf) cells, e.g. Sf9, Sf21, *Trichoplusia ni* cells, e.g. High Five cells, and *Drosophila* S2 cells. Examples of fungi (including yeast) host cells are *S. cerevisiae*, *Kluyveromyces lactis* (*K. lacus*), species of *Candida* including *C. albicans* and *C. glabraia*, *Aspergillus nidulans*, *Schizosaccharomyces pombe* (*S. pombe*), *Pichia pastoris*, and *Yarrowia lipolytica*. Examples of mammalian cells are COS cells, baby hamster kidney cells, mouse L cells, LNCaP cells, Chinese hamster ovary (CHO) cells, human embryonic kidney (HEK) cells, and African green monkey cells, CV1 cells, HeLa cells, MDCK cells, Vero and Hep-2 cells. *Xenopus laevis* oocytes, or other cells of amphibian origin, may also be used. Examples of prokaryotic host cells include bacterial cells, for example, *E. coli*, *B. subtilis*, *Salmonella typhi* and mycobacteria.

Vectors, e.g., vectors comprising polynucleotides of a modified or mutated RSV F protein; and at least one immunogen including but not limited to RSV G, N, or SH or portions thereof, and/or any chimeric molecule described above, can be transfected into host cells according to methods well known in the art. For example, introducing nucleic acids into eukaryotic cells can be by calcium phosphate co-precipitation, electroporation, microinjection, lipofection, and transfection employing polyamine transfection reagents. In one embodiment, the vector is a recombinant baculovirus. In another embodiment, the recombinant baculovirus is transfected into a eukaryotic cell. In a preferred embodiment, the cell is an insect cell. In another embodiment, the insect cell is a Sf9 cell.

This invention also provides for constructs and methods that will increase the efficiency of VLP production. For example, the addition of leader sequences to the RSV F, M, G, N, SH, or portions thereof, and/or any chimeric air heterologous molecules described above, can improve the efficiency of protein transporting within the cell. For example, a heterologous signal sequence can be fused to the F, M, G, N, SH, or portions thereof, and/or any chimeric or heterologous molecule described above. In one embodiment, the signal sequence can be derived from the gene of an insect cell and fused to M, F, G, N, SH, or portions thereof, and/or any chimeric or heterologous molecules described above. In another embodiment, the signal peptide is the chitinase signal sequence, which works efficiently in baculovirus expression systems.

Another method to increase efficiency of VLP production is to codon optimize the nucleotides that encode RSV including a modified or mutated RSV F protein, M, G, N, SH or portions thereof, and/or any chimeric or heterologous molecules described above for a specific cell type. For examples of codon optimizing nucleic acids for expression in Sf9 cell see SEQ ID Nos: 3, 5, 7, 9, 13, 17, 19, and 25.

The invention also provides for methods of producing VLPs, the methods comprising expressing RSV genes including a modified or mutated RSV F protein, and at least one additional protein, including but not limited to RSV M, G, N, SH, or portions thereof, and/or any chimeric or heterologous molecules described above under conditions that allow VLP formation. Depending on the expression system and host cell selected, the VLPs are produced by growing host cells transformed by an expression vector under conditions whereby the recombinant proteins are expressed and VLPs are formed. In one embodiment, the invention comprises a method of producing a VLP, comprising transfecting vectors encoding at least one modified or mutated RSV F protein into a suitable host cell and expressing the modified or mutated RSV F protein under conditions that allow VLP formation. In another embodiment, the eukaryotic cell is selected from the group consisting of, yeast, insect, amphibian, avian or mammalian cells. The selection of the appropriate growth conditions is within the skill or a person with skill of one of ordinary skill in the art.

Methods to grow cells engineered to produce VLPs of the invention include, but are not limited to, batch, batch-fed, continuous and perfusion cell culture techniques. Cell culture means the growth and propagation of cells in a bioreactor (a fermentation chamber) where cells propagate and express protein (e.g. recombinant proteins) for purification and isolation. Typically, cell culture is performed under sterile, controlled temperature and atmospheric conditions in a bioreactor. A bioreactor is a chamber used to culture cells in which environmental conditions such as temperature, atmosphere, agitation and/or pH can be monitored. In one embodiment, the bioreactor is a stainless steel chamber. In another embodiment, the bioreactor is a pre-sterilized plastic bag (e.g. Cellbag®, Wave Biotech, Bridgewater, NJ). In other embodiment, the pre-sterilized plastic bags are about 50 L to 1000 L bags.

The VLPs are then isolated using methods that preserve the integrity thereof such as by gradient centrifugation, e.g., cesium chloride, sucrose and iodixanol, as well as standard purification techniques including, e.g., ion exchange and gel filtration chromatography.

The following is an example of how VLPs of the invention can be made, isolated and purified. Usually VLPs are produced from recombinant cell lines engineered to create VLPs when the cells are grown in cell culture (see above). A person of skill in the art would understand that there are additional methods that can be utilized to make and purify VLPs of the invention, thus the invention is not limited to the method described.

Production of VLPs of the invention can start by seeding Sf9 cells (non-infected) into shaker flasks, allowing the cells to expand and scaling up as the cells grow and multiply (for example from a 125-ml flask to a 50 L Wave bag). The medium used to grow the cell is formulated for the appropriate cell line (preferably serum free media, e.g. insect medium ExCell-420, JRH). Next, the cells are infected with recombinant baculovirus at the most efficient multiplicity of infection (e.g. from about 1 to about 3 plaque forming units per cell). Once infection has occurred, the modified or mutated RSV F protein, M, G, N, SH, or portions thereof, and/or any chimeric or heterologous molecule described above, are expressed from the virus genome, self assemble into VLPs and are secreted from the cells approximately 24 to 72 hours post infection. Usually, infection is most efficient when the cells are in mid-log phase of growth ($4-8\times10^6$ cells/ml) and are at least about 90% viable.

VLPs of the invention can be harvested approximately 48 to 96 hours post infection, when the levels of VLPs in the cell culture medium are near the maximum but before extensive cell lysis. The Sf9 cell density and viability at the time of harvest can be about $0.5\times10^6$ cells/ml to about $1.5\times10^6$ cells/ml with at least 20% viability, as shown by dye exclusion assay. Next, the medium is removed and clarified. NaCl can be added to the medium to a concentration of about 0.4 to about 1.0 M, preferably to about 0.5 M, to avoid VLP aggregation. The removal of cell and cellular debris from the cell culture medium containing VLPs of the invention can be accomplished by tangential flow filtration (TFF) with a single use, pre-sterilized hollow fiber 0.5 or 1.00 μm filter cartridge or a similar device.

Next, VLPs in the clarified culture medium can be concentrated by ultra-filtration using a disposable, pre-sterilized 500,000 molecular weight cut off hollow fiber cartridge. The concentrated VLPs can be diafiltrated against 10 volumes pH 7.0 to 8.0 phosphate-buffered saline (PBS) containing 0.5 M NaCl to remove residual medium components.

The concentrated, diafiltered VLPs can be furthered purified on a 20% to 60% discontinuous sucrose gradient in pH 7.2 PBS buffer with 0.5 M NaCl by centrifugation at 6,500×g for 18 hours at about 4° C. to about 10° C. Usually VLPs will form a distinctive visible band between about 30% to about 40% sucrose or at the interface (in a 20% and 60% step gradient) that can be collected from the gradient and stored. This product can be diluted to comprise 200 mM of NaCl in preparation for the next step in the purification process. This product contains VLPs and may contain intact baculovirus particles.

Further purification of VLPs can be achieved by anion exchange chromatography, or 44% isopycnic sucrose cushion centrifugation. In anion exchange chromatography, the sample from the sucrose gradient (see above) is loaded into column containing a medium with an anion (e.g. Matrix Fractolzel EMD TMAE) and eluded via a salt gradient (from about 0.2 M to about 1.0 M of NaCl) that can separate the VLP from other contaminates (e.g. baculovirus and DNA/RNA). In the sucrose cushion method, the sample comprising the VLPs is added to a 44% sucrose cushion and centrifuged for about 18 hours at 30,000 g. VLPs form a band at the top of 44% sucrose, while baculovirus precipitates at the bottom and other contaminating proteins stay in the 0% sucrose layer at the top. The VLP peak or band is collected.

The intact baculovirus can be inactivated, if desired. Inactivation can be accomplished by chemical methods, for example, formalin or β-propiolactone (BPL). Removal and/or inactivation of intact baculovirus can also be largely accomplished by using selective precipitation and chromatographic methods known in the art, as exemplified above. Methods of inactivation comprise incubating the sample containing the VLPs in 0.2% of BPL for 3 hours at about 25° C. to about 27° C. The baculovirus can also be inactivated by incubating the sample containing the VLPs at 0.05% BPL at 4° C. for 3 days, then at 37° C. for one hour.

After the inactivation/removal step, the product comprising VLPs can be run through another diafiltration step to remove any reagent from the inactivation step and/or any residual sucrose, and to place the VLPs into the desired buffer (e.g. PBS). The solution comprising VLPs can be sterilized by methods known in the art (e.g. sterile filtration) and stored in the refrigerator or freezer.

The above techniques can be practiced across a variety of scales. For example, T-flasks, shake-flasks, spinner battles, up to industrial sized bioreactors. The bioreactors can comprise either a stainless steel tank or a pre-sterilized plastic bag (for example, the system sold by Wave Biotech, Bridgewater, NJ). A person with skill in the art will know what is most desirable for their purposes.

Expansion and production of baculovirus expression vectors and infection of cells with recombinant baculovirus to produce recombinant RSV VLPs can be accomplished in insect cells, for example Sf9 insect cells as previously described. In one embodiment, the cells are SF9 infected with recombinant baculovirus engineered to produce RSV VLPs.

Pharmaceutical or Vaccine Formulations and Administration

The pharmaceutical compositions useful herein contain a pharmaceutically acceptable carrier, including any suitable diluent or excipient, which includes any pharmaceutical agent that does not itself induce the production of an immune response harmful to the vertebrate receiving the composition, and which may be administered without undue toxicity and a. modified or mutated RSV F protein, an RSV F micelle comprising a modified or mutated RSV F protein, or a VLP comprising a modified or mutated RSV F protein of the invention. As used herein, the term "pharmaceutically acceptable" means being approved by a regulatory agency of the Federal or a state government or listed in the U.S. Pharmacopia, European Pharmacopia or other generally recognized pharmacopia for use in mammals, and more particularly in humans. These compositions can be useful as a vaccine and/or antigenic compositions for inducing a protective immune response in a vertebrate.

The invention encompasses a pharmaceutically acceptable vaccine composition comprising VLPs comprising at least one modified or mutated RSV F protein, and at least one additional protein, including but not limited to RSV M, G, N, SH, or portions thereof, and/or any chimeric or heterologous molecules described above. In one embodiment, the pharmaceutically acceptable vaccine composition comprises VLPs comprising at least one modified or mutated RSV F protein and at least one additional immunogen. In another embodiment, the pharmaceutically acceptable vaccine composition comprises VLPs comprising at least one modified or mutated RSV F protein and at least one RSV M protein. In another embodiment, the pharmaceutically acceptable vaccine composition comprises VLPs comprising at least one modified or mutated. RSV F protein and at least one BRSV M protein. In another embodiment, the pharmaceutically acceptable vaccine composition comprises VLPs comprising at least one modified or mutated RSV F protein and at least one influenza M1 protein. In another embodiment, the pharmaceutically acceptable vaccine composition comprises VLPs comprising at least one modified or mutated RSV F protein and at least one avian influenza M1 protein.

In another embodiment, the pharmaceutically acceptable vaccine composition comprises VLPs further comprising an RSV G protein, including but not limited to a HRSV, BRSV or avian RSV G protein. In another embodiment, the pharmaceutically acceptable vaccine composition comprises VLPs further comprising RSV N protein, including but not limited to a HRSV, BRSV or avian RSV N protein. In another embodiment, the pharmaceutically acceptable vaccine composition comprises VLPs further comprising RSV SH protein, including but not limited to a HRSV, BRSV or avian RSV SH protein.

In another embodiment, the invention encompasses a pharmaceutically acceptable vaccine composition comprising chimeric VLPs such as VLPs comprising BRSV M and a modified or mutated RSV F protein and/or G, H, or SH protein from a RSV and optionally HA or NA protein derived from an influenza virus, wherein the HA or NA protein is a fused to the transmembrane domain and cytoplasmic tail of RSV F and/or G protein.

The invention also encompasses a pharmaceutically acceptable vaccine composition comprising modified or mutated RSV F protein, an RSV F micelle comprising a modified or mutated RSV F protein, or a VLP comprising a modified or mutated RSV F protein as described above.

In one embodiment, the pharmaceutically acceptable vaccine composition comprises VIPs comprising a modified or mutated RSV F protein and at least one additional protein. In another embodiment, the pharmaceutically acceptable vaccine composition comprises VLPs further comprising RSV M protein, such as but not limited to a BRSV M protein. In another embodiment, the pharmaceutically acceptable vaccine composition comprises VLPs further comprising RSV G protein, including but not limited to a HRSV G protein. In another embodiment, the pharmaceutically acceptable vaccine composition comprises VLPs further comprising RSV N protein, including but not limited to a HRSV, BRSV or avian RSV N protein. In another embodiment, the pharmaceutically acceptable vaccine composition comprises VLPs further comprising RSV SH protein, including but not limited to a HRSV, BRSV or avian RSV SH protein. In another embodiment, the pharmaceutically acceptable vaccine composition comprises VLPs comprising BRSV M protein and F and/or G protein from HRSV group A. In another embodiment, the pharmaceutically acceptable vaccine composition comprises VLPs comprising BRSV M protein and F and/or G protein from HRSV group B. In another embodiment, the invention encompasses a pharmaceutically acceptable vaccine composition comprising chimeric VLPs such as VLPs comprising chimeric M protein from a BRSV and optionally HA protein derived from an influenza virus, wherein the M protein is fused to the influenza. HA protein. In another embodiment, the invention encompasses a pharmaceutically acceptable vaccine composition comprising chimeric VLPs such as VLPs comprising BRSV M, and a chimeric F and/or G protein from a RSV and optionally HA protein derived from an influenza virus, wherein the chimeric influenza HA protein is fused to the transmembrane domain and cytoplasmic tail of RSV F and/or G protein. In another embodiment, the invention encompasses a pharmaceutically acceptable vaccine composition comprising chimeric VLPs such as VLPs comprising BRSV M and a chimeric F and/or G protein from a RSV and optionally HA or NA protein derived from an influenza virus, wherein the HA or NA protein is a fused to the transmembrane domain and cytoplasmic tail of RSV F and/or G protein.

The invention also encompasses a pharmaceutically acceptable vaccine composition comprising a chimeric VLP that comprises at least one RSV protein. In one embodiment, the pharmaceutically acceptable vaccine composition comprises VLPs comprising a modified or mutated RSV F protein and at least one immunogen from a heterologous infectious agent or diseased cell. In another embodiment, the immunogen from a heterologous infectious agent is a viral protein. In another embodiment, the viral protein from a heterologous infectious agent is an envelope associated protein. In another embodiment, the viral protein from a heterologous infectious agent is expressed on the surface of VLPs. In another embodiment, the protein from an infectious agent comprises an epitope that will generate a protective immune response in a vertebrate.

The invention also encompasses a kit for immunizing a vertebrate, such as a human subject, comprising VLPs that comprise at least one RSV protein. In one embodiment, the kit comprises VLPs comprising a modified or mutated RSV F protein. In one embodiment, the kit further comprises a RSV M protein such as a BRSV M protein. In another embodiment, the kit further comprises a RSV G protein. In another embodiment, the invention encompasses a kit comprising VLPs which comprises a chimeric M protein from a BRSV and optionally HA protein derived from an influenza virus, wherein the M protein is fused to the BRSV M. In another embodiment, the invention encompasses a kit comprising VLPs which comprises a chimeric M protein from a BRSV, a RSV F and/or G protein and an immunogen from a heterologous infectious agent. In another embodiment, the invention encompasses a kit comprising VLPs which comprises a M protein from a BRSV, a chimeric RSV F and/or G protein and optionally HA protein derived from an influenza virus, wherein the HA protein is fused to the transmembrane domain and cytoplasmic tail of RSV F or G protein. In another embodiment, the invention encompasses a kit comprising VLPs which comprises M protein from a BRSV, a chimeric RSV F and/or G protein and optionally HA or NA protein derived from an influenza virus, wherein the HA protein is fused to the transmembrane domain and cytoplasmic tail of RSV F and/or G protein.

In one embodiment, the invention comprises an immunogenic formulation comprising at least one effective dose of a modified or mutated RSV F protein. In another embodiment, the invention comprises an immunogenic formulation comprising at least one effective dose of an RSV F micelle comprising a modified or mutated RSV F protein. In yet another embodiment, the invention comprises an immunogenic formulation comprising at least one effective dose of a VLP comprising a modified or mutated RSV F protein as described above.

The immunogenic formulation of the invention comprises a modified or mutated RSV F protein, an RSV F micelle comprising a modified or mutated RSV F protein, or a VLP comprising a modified or mutated RSV F protein, and a pharmaceutically acceptable carrier or excipient. Pharmaceutically acceptable carriers include but are not limited to saline, buffered saline, dextrose, water, glycerol, sterile isotonic aqueous buffer, and combinations thereof. A thorough discussion of pharmaceutically acceptable carriers, diluents, and other excipients is presented in Remington's Pharmaceutical Sciences (Mack Pub. Co. N.J. current edition). The formulation should suit the mode of administration, in a preferred embodiment, the formulation is suitable for administration to humans, preferably is sterile, non-particulate and/or non-pyrogenic.

The composition, if desired, can also contain minor amounts of wetting or emulsifying agents, or pH buffering agents. The composition can be a solid form, such as a lyophilized powder suitable for reconstitution, a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

The invention also provides for a pharmaceutical pack or kit comprising one or more containers filled with one or more of the ingredients of the vaccine formulations of the invention. In a preferred embodiment, the kit comprises two containers, one containing a modified or mutated RSV F protein, an RSV F micelle comprising a modified or mutated RSV F protein, or a VLP comprising a modified or mutated RSV F protein, and the other containing an adjuvant. Associated with such container(s) can be a notice in the form prescribed by a governmental agency regulating the manufacture, use or sale of pharmaceuticals or biological products, which notice reflects approval by the agency of manufacture, use or sale for human administration.

The invention also provides that the formulation be packaged in a hermetically sealed container such as an ampoule or sachette indicating the quantity of composition. In one embodiment, the composition is supplied as a liquid, in another embodiment, as a dry sterilized lyophilized powder or water free concentrate in a hermetically sealed container and can be reconstituted, e.g., with water or saline to the appropriate concentration for administration to a subject.

In an alternative embodiment, the composition is supplied in liquid form in a hermetically sealed container indicating the quantity and concentration of the composition. Preferably, the liquid form of the composition is supplied in a hermetically sealed container at least about 50 µg/ml, more preferably at least about 100 µg/ml, at least about 200 µg/ml, at least 500 µg/ml, or at least 1 mg/ml.

As an example, chimeric RSV VLPs comprising a modified or mutated RSV F protein of the invention are administered in an effective amount or quantity (as defined above) sufficient to stimulate an immune response, each a response against one or more strains of RSV. Administration of the modified or mutated RSV F protein, an RSV F micelle comprising a modified or mutated RSV F protein, or VLP of the invention elicits immunity against RSV. Typically, the dose can be adjusted within this range based on, e.g., age, physical condition, body weight, sex, diet, time of administration, and other clinical factors. The prophylactic vaccine formulation is systemically administered, e.g., by subcutaneous or intramuscular injection using a needle and syringe, or a needle-less injection device. Alternatively, the vaccine formulation is administered intranasally, either by drops, large particle aerosol (greater than about 10 microns), or spray into the upper respiratory tract. While any of the above routes of delivery results in an immune response, intranasal administration confers the added benefit of eliciting mucosal immunity at the site of entry of many viruses, including RSV and influenza.

Thus, the invention also comprises a method of formulating a vaccine or antigenic composition that induces immunity to an infection or at least one disease symptom thereof to a mammal, comprising adding to the formulation an effective dose of a modified or mutated RSV F protein, an RSV F micelle comprising a modified or mutated RSV F protein, or a VLP comprising a modified or mutated RSV F protein. In one embodiment, the infection is an RSV infection.

While stimulation of immunity with a single dose is possible, additional dosages can be administered, by the same or different route, to achieve the desired effect. In neonates and infants, for example, multiple administrations may be required to elicit sufficient levels of immunity. Administration can continue at intervals throughout childhood, as necessary to maintain sufficient levels of protection against infections, e.g. RSV infection. Similarly, adults who are particularly susceptible to repeated or serious infections, such as, for example, health care workers, day care workers, family members of young children, the elderly, and individuals with compromised cardiopulmonary function may require multiple immunizations to establish and/or maintain protective immune response Levels of induced immunity can be monitored, for example, by measuring amounts of neutralizing secretory and serum antibodies, and dosages adjusted or vaccinations repeated as necessary to elicit and maintain desired levels of protection.

Methods of administering a composition comprising a modified or mutated RSV F protein, an RSV F micelle comprising a modified or mutated RSV F protein, or a VLP comprising a modified or mutated RSV F protein (e.g. vaccine and/or antigenic formulations) include, but are not limited to, parenteral administration (e.g., intradermal, intramuscular, intravenous and subcutaneous), epidural, and mucosal (e.g., intranasal and oral or pulmonary routes or by suppositories). In a specific embodiment, compositions of the present invention are administered intramuscularly, intravenously, subcutaneously, transdermally or intradermally. The compositions may be administered by any convenient route, for example by infusion or bolus injection, by absorption through epithelial or mucocutaneous linings (e.g., oral mucous, colon, conjunctiva, nasopharynx, oropharynx, vagina, urethra, urinary bladder and intestinal mucosa, etc.) and may be administered together with other biologically active agents. In some embodiments, intranasal or other mucosal routes of administration of a composition of the invention may induce an antibody or other immune response that is substantially higher than other routes of administration. In another embodiment, intranasal or other mucosal routes of administration of a composition of the invention may induce an antibody or other immune response that will induce cross protection against other strains of RSV. Administration can be systemic or local.

In yet another embodiment, the vaccine and/or immunogenic formulation is administered in such a manner as to target mucosal tissues in order to elicit an immune response at the site of immunization. For example, mucosal tissues such as gut associated lymphoid tissue (GALT) can be targeted for immunization by using oral administration of compositions which contain adjuvants with particular mucosal targeting properties. Additional mucosal tissues can also be targeted, such as nasopharyngeal lymphoid tissue (NALT) and bronchial-associated lymphoid tissue (BALT).

Vaccines and/or immunogenic formulations of the invention may also be administered on a dosage schedule, for example, an initial administration of the vaccine composition with subsequent booster administrations. In particular embodiments, a second dose of the composition is administered anywhere from two weeks to one year, preferably from about 1, about 2, about 3, about 4, about 5 to about 6 months, after the initial administration. Additionally, a third dose may be administered after the second dose and from about three months to about two years, or even longer, preferably about 4, about 5, or about 6 months, or about 7 months to about one year after the initial administration. The third dose may be optionally administered when no or low levels of specific immunoglobulins are detected in the serum and/or urine and/or mucosal secretions of the subject after the second dose. In a preferred embodiment, a second dose is administered about one month after the first administration and a third dose is administered about six months after the first administration. In another embodiment, the second dose is administered about six months after the first administration. In another embodiment, the compositions of the invention can be administered as part of a combination therapy. For example, compositions of the invention can be formulated with other immunogenic compositions, antivirals and/or antibiotics The dosage of the pharmaceutical composition can be determined readily by the skilled artisan, for example, by first identifying doses effective to elicit a prophylactic or therapeutic immune response, by measuring the serum titer of virus specific immunoglobulins or by measuring the inhibitory ratio of antibodies in serum samples, or urine samples, or mucosal secretions. The dosages can be determined from animal studies. A non-limiting list of animals used to study the efficacy of vaccines include the guinea pig, hamster, ferrets, chinchilla, mouse and cotton rat. Most animals are not natural hosts to infectious agents but can still serve in studies of various aspects of the disease. For example, any of the above animals can be dosed with a vaccine candidate, e.g. modified or mutated RSV F proteins, an RSV F micelle comprising a modified or mutated RSV F protein, or VLPs of the invention, to partially characterize the immune response induced, and/or to determine if any neutralizing antibodies have been produced. For example, many studies have been conducted in the mouse model because mice are small size and their low cost allows researchers to conduct studies on a larger scale.

In addition, human clinical studies can be performed to determine the preferred effective dose for humans by a skilled artisan. Such clinical studies are routine and well known in the art. The precise dose to be employed will also depend on the route of administration. Effective doses may be extrapolated from dose-response curves derived from in vitro or animal test systems.

As also well known in the art, the immunogenicity of a particular composition can be enhanced by the use of non-specific stimulators of the immune response, known as adjuvants. Adjuvants have been used experimentally to promote a generalized increase in immunity against unknown antigens (e.g., U.S. Pat. No. 4,877,611). Immunization protocols have used adjuvants to stimulate responses for many years, and as such, adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation. The inclusion of any adjuvant described in Vogel et al., "A Compendium of Vaccine Adjuvants and Excipients ($2^{nd}$ Edition)," herein incorporated by reference in its entirety for all purposes, is envisioned within the scope of this invention.

Exemplary, adjuvants include complete Freund's adjuvant (a non-specific stimulator of the immune response containing killed Mycobacterium tuberculosis), incomplete Freund's adjuvants and aluminum hydroxide adjuvant. Other adjuvants comprise GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion also is contemplated. MF-59, Novasomes®, MHC antigens may also be used.

In one embodiment of the invention the adjuvant is a paucilamellar lipid vesicle having about two to ten bilayers arranged in the form of substantially spherical shells separated by aqueous layers surrounding a large amorphous central cavity free of lipid bilayers. Paucilamellar lipid vesicles may act to stimulate the immune response several ways, as non-specific stimulators, as carriers for the antigen, as carriers of additional adjuvants, and combinations thereof. Paucilamellar lipid vesicles act as non-specific immune stimulators when, for example, a vaccine is prepared by intermixing the antigen with the preformed vesicles such that the antigen remains extracellular to the vesicles. By encapsulating an antigen within the central cavity of the vesicle, the vesicle acts both as an immune stimulator and a carrier for the antigen. In another embodiment, the vesicles are primarily made of nonphospholipid vesicles. In other embodiment, the vesicles are Novasomes®. Novasomes® are paucilamellar nonphospholipid vesicles ranging from about 100 nm to about 500 nm. They comprise Brij 72, cholesterol, oleic acid and squalene. Novasomes have been shown to be an effective adjuvant for influenza antigens (see, U.S. Pat. Nos. 5,629,021, 6,387,373, and 4,911,928, herein incorporated by reference in their entireties for all purposes).

The compositions of the invention can also be formulated with "immune stimulators." These are the body's own chemical messengers (cytokines) to increase the immune system's response. Immune stimulators include, but not limited to, various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7,2, etc. The immunostimulatory molecules can be administered in the same formulation as the compositions of the invention, or can be administered separately. Either the protein or an expression vector encoding the protein can be administered to produce an immunostimulatory effect. Thus in one embodiment, the invention comprises antigenic and vaccine formulations comprising an adjuvant and/or an immune stimulator.

Methods of Stimulating an Immune Response

The modified or mutated. RSV F proteins, the RSV F micelles comprising a modified or mutated RSV F protein, or the VLPs of the invention are useful for preparing compositions that stimulate an immune response that confers immunity or substantial immunity to infectious agents. Both mucosal and cellular immunity may contribute to immunity to infectious agents and disease. Antibodies secreted locally in the upper respirators, tract are a major factor in resistance to natural infection. Secretory immunoglobulin A (sIgA) is involved in the protection of the upper respiratory tract and serum IgG in protection of the lower respiratory tract. The immune response induced by an infection protects against reinfection with the same virus or an antigenically similar viral strain. For example, RSV undergoes frequent and unpredictable changes; therefore, after natural infection, the effective period of protection provided by the host's immunity may only be effective for a few years against the new strains of virus circulating in the community.

Thus, the invention encompasses a method of inducing immunity to infections or at least one disease symptom thereof in a subject, comprising administering at least one effective dose of a modified or mutated RSV F protein, an RSV F micelle comprising a modified or mutated RSV F protein, or a VLP comprising a modified or mutated RSV F protein. In one embodiment, the method comprises administering VLPs comprising a modified or mutated RSV F protein and at least one additional protein. In another embodiment, the method comprises administering VLPs further comprising an RSV M protein, for example, a BRSV M protein. In another embodiment, the method comprises administering VLPs further comprising a RSV N protein. In another embodiment, the method comprises administering VLPs further comprising a RSV G protein. In another embodiment, the method comprises administering VLPs further comprising a RSV SH protein. In another embodiment, the method comprises administering VLPs further comprising F and/or G protein from HRSV group A and/or group B. In another embodiment, the method comprises administering VLPs comprising M protein from BRSV and a chimeric RSV F and/or G protein or MMTV envelope protein, for example, HA or NA protein derived from an influenza virus, wherein the HA and/or NA protein is fused to the transmembrane domain and cytoplasmic tail of the RSV F and/or G protein or MMTV envelope protein. In another embodiment, the method comprises administering VLPs comprising M protein from BRSV and a chimeric RSV F and/or G protein and optionally HA or NA protein derived from an influenza virus, wherein the HA or NA protein is fused to the transmembrane domain and cytoplasmic tail of RSV F and/or G protein. In another embodiment, the subject is a mammal. In another embodiment, the mammal is a human. In another embodiment, RSV VLPs are formulated with an adjuvant or immune stimulator.

In one embodiment, the invention comprises a method to induce immunity to RSV infection or at least one disease symptom thereof in a subject, comprising administering at least one effective dose of a modified or mutated RSV F protein. In another embodiment, the invention comprises a method to induce immunity to RSV infection or at least one disease symptom thereof in a subject, comprising administering at least one effective dose of an RSV F micelle comprising a modified or mutated RSV F protein. In yet another embodiment, the invention comprises a method to induce immunity to RSV infection or at least one disease symptom thereof in a subject, comprising administering at least one effective dose of a RSV VLPs, wherein the VLPs comprise a modified or mutated RSV F protein, M, G, SH, and/or N proteins. In another embodiment, a method of inducing immunity to RSV infection or at least one symptom thereof in a subject, comprises administering at least one effective dose of a RSV VLPs, wherein the VlPs consists essentially of BRSV M (including chimeric M), and RSV F, G, and/or or N proteins. The VLPs may comprise additional RSV proteins and/or protein contaminates in negligible concentrations. In another embodiment, a method of inducing immunity to RSV infection or at least one symptom thereof in a subject, comprises administering at least one effective dose of a RSV VLPs, wherein the VLPs consists of BRSV M (including chimeric M), RSV G and/or F. In another embodiment, a, method of inducing immunity to RSV infection or at least one disease symptom in a subject, comprises administering at least one effective dose of a RSV VLPs comprising RSV proteins, wherein the RSV proteins consist of BRSV M (including chimeric M), F, G, and/or N proteins, including chimeric F, G, and/or or N proteins. These VLPs contain BRSV M (including chimeric M), RSV F, G, and/or N proteins and may contain additional cellular constituents such as cellular proteins, baculovirus proteins, lipids, carbohydrates etc., but do not contain additional RSV proteins (other than fragments of BRSV M (including chimeric M), BRSV/RSV F, G, and/or N proteins. In another embodiment, the subject is a vertebrate. In one embodiment the vertebrate is a mammal. In another embodiment, the mammal is a human. In another embodiment, the method comprises inducing immunity to RSV infection or at least one disease symptom by administering the formulation in one dose. In another embodiment, the method comprises inducing immunity to RSV infection or at least one disease symptom by administering the formulation in multiple doses.

The invention also encompasses inducing immunity to an infection, or at least one symptom thereof, in a subject caused by an infectious agent, comprising administering at least one effective dose of a modified or mutated RSV F protein, an RSV F micelle comprising a modified or mutated RSV F protein, or a VLP comprising a modified or mutated RSV F protein. In one embodiment, the method comprises administering VLPs comprising a modified or mutated RSV F protein and at least one protein from a heterologous infectious agent. In one embodiment, the method comprises administering VLPs comprising a modified or mutated RSV F protein and at least one protein from the same or a heterologous infectious agent. In another embodiment, the protein from the heterologous infectious agent is a viral protein. In another embodiment, the protein from the infectious agent is an envelope associated protein. In another embodiment, the protein from the infectious agent is expressed on the surface of VLPs. In another embodiment, the protein from the infectious agent comprises an epitope that will generate a protective immune response in a vertebrate. In another embodiment, the protein from the infectious agent can associate with RSV M protein such as BRSV M protein, RSV F, G and/or N protein. In another embodiment, the protein from the infectious agent is fused to a RSV protein such as a BRSV M protein, RSV F, G and/or N protein, in another embodiment, only a portion of a protein from the infectious agent is fused to a RSV protein such as a BRSV M protein, RSV F, G and/or N protein. In another embodiment, only a portion of a protein from the infectious agent is fused to a portion of a RSV protein such as a BRSV M protein, RSV F, G and/or N protein. In another embodiment, the portion of the protein from the infectious agent fused to the RSV protein is expressed on the surface of VLPs. In other embodiment, the RSV protein, or portion thereof, fused to the protein from the infectious agent associates with the RSV M protein. In other embodiment, the RSV protein, or portion thereof, is derived from RSV F, G, N and/or P. In another embodiment, the chimeric VLPs further comprise N and/or P protein from RSV. In another embodiment, the chimeric VLPs comprise more than one protein from the same and/or a heterologous infectious agent. In another embodiment, the chimeric. VLPs comprise more than one infectious agent protein, thus creating a multivalent VLP.

Compositions of the invention can induce substantial immunity in a vertebrate (e.g. a human) when administered to the vertebrate. The substantial immunity results from an immune response against compositions of the invention that protects or ameliorates infection or at least reduces a symptom of infection in the vertebrate. In some instances, if the vertebrate is infected, the infection will be asymptomatic. The response may not be a fully protective response. In this case, if the vertebrate is infected with an infectious agent, the vertebrate will experience reduced symptoms or a shorter duration of symptoms compared to a non-immunized vertebrate.

In one embodiment, the invention comprises a method of inducing substantial immunity to RSV virus infection or at least one disease symptom in a subject, comprising administering at least one effective dose of a modified or mutated RSV F protein, an RSV F micelle comprising a modified or mutated RSV F protein, or a VLP comprising a modified or mutated RSV F protein. In another embodiment, the invention comprises a method of vaccinating a mammal against RSV comprising administering to the mammal a protection-inducing amount of a modified or mutated RSV F protein, an RSV F micelle comprising a modified or mutated RSV F protein, or a VLP comprising a modified or mutated RSV F protein. In one embodiment, the method comprises administering VLPs further comprising an RSV M protein, such as BRSV M protein. In another embodiment, the method further comprises administering VLPs comprising RSV G protein, for example a HRSV G protein. In another embodiment, the method further comprises administering VLPs comprising the N protein from HRSV group A. In another embodiment, the method further comprises administering VLPs comprising the N protein from HRSV group B. In another embodiment, the method comprises administering VLPs comprising chimeric M protein from BRSV and F and/or G protein derived from RSV wherein the F and/or G protein is fused to the transmembrane and cytoplasmic tail of the M protein. In another embodiment, the method comprises administering VLPs comprising M protein from BRSV and chimeric RSV F and/or G protein wherein the F and/or G protein is a fused to the transmembrane domain and cytoplasmic tail of influenza HA and/or NA protein. In another embodiment, the method comprises administering VLPs comprising M protein from BRSV and chimeric RSV F and/or G protein and optionally an influenza HA and/or NA protein wherein the F and/or G protein is a fused to the transmembrane domain and cytoplasmic tail of the HA protein. In another embodiment, the method comprises administering VLPs comprising M protein from BRS and chimeric RSV F and/or G protein, and optionally an influenza. HA and/or NA protein wherein the HA and/or NA protein is fused to the transmembrane domain and cytoplasmic tail of RSV F and/or G protein.

The invention also encompasses a method of inducing substantial immunity to an infection, or at least one disease symptom in a subject caused by an infectious agent, comprising administering at least one effective dose of a modified or mutated RSV F protein, an RSV F micelle comprising a modified or mutated RSV F protein, or a VLP comprising a modified or mutated RSV F protein. In one embodiment, the method comprises administering VLPs further comprising a RSV M protein, such as BRSV M protein, and at least one protein from another infectious agent. In one embodiment, the method comprises administering VLPs further comprising a BRSV M protein and at least one protein from the same or a heterologous infectious agent. In another embodiment, the protein from the infectious agent is a viral protein. In another embodiment, the protein from the infectious agent is an envelope associated protein. In another embodiment, the protein from the infectious agent is expressed on the surface of VLPs. In another embodiment, the protein from the infectious agent comprises an epitope that will generate a protective immune response in a vertebrate. In another embodiment, the protein from the infectious agent can associate with RSV M protein. In another embodiment, the protein from the infectious agent can associate with BRSV M protein. In another embodiment, the protein from the infectious agent is fused to a RSV protein. In another embodiment, only a portion of a protein from the infectious agent is fused to a RSV protein. In another embodiment, only a portion of a protein from the infectious agent is fused to a portion of a RSV protein. In another embodiment, the portion of the protein from the infectious agent fused to the RSV protein is expressed on the surface of VLPs. In other embodiment, the RSV protein, or portion thereof, fused to the protein from the infectious agent associates with the RSV M protein. In other embodiment, the RSV protein, or portion thereof, fused to the protein from the infectious agent associates with the BRSV M protein. In other embodiment, the RSV protein, or portion thereof, is derived from RSV F, G, N and/or P. In another embodiment, the VLPs further comprise N and/or P protein from RSV. In another embodiment, the VLPs comprise more than one protein from the infectious agent. In another embodiment, the VLPs comprise more than one infectious agent protein, thus creating a multivalent VLP.

In another embodiment, the invention comprises a method of inducing a protective antibody response to an infection or at least one symptom thereof in a subject, comprising administering at least one effective dose of a modified or mutated RSV F protein, an RSV F micelle comprising a modified or mutated RSV F protein, or a VLP comprising a modified or mutated RSV F protein as described above.

As used herein, an "antibody" is a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. Antibodies exist as intact immunoglobulins or as a number of well-characterized fragments produced by digestion with various peptidases.

In one embodiment, the invention comprises a method of inducing a protective cellular response to RSV infection or at least one disease symptom in a subject, comprising administering at least one effective dose of a modified or mutated RSV F protein. In another embodiment, the invention comprises a method of inducing a protective cellular response to RSV infection or at least one disease symptom in a subject, comprising administering at least one effective dose an RSV F micelle comprising a modified or mutated RSV F protein. In yet another embodiment, the invention comprises a method of inducing a protective cellular response to RSV infection or at least one disease symptom in a subject, comprising administering at least one effective dose a VLP, wherein the VLP comprises a modified or mutated RSV F protein as described above. Cell-mediated immunity also plays a role in recovery from RSV infection and may prevent RSV-associated complications. RSV-specific cellular lymphocytes have been detected in the blood and the lower respiratory tract secretions of infected subjects. Cytolysis of RSV-infected cells is mediated by CTLs in concert with RSV-specific antibodies and complement. The primary cytotoxic response is detectable in blood after 6-14 days and disappears by day 21 in infected or vaccinated individuals (Ennis et al., 1981). Cell-mediated immunity may also play a role in recovery from RSV infection and may prevent RSV-associated complications. RSV-specific cellular lymphocytes have been detected in the blood and the lower respiratory tract secretions of infected subjects.

As mentioned above, the immunogenic compositions of the invention prevent or reduce at least one symptom of RSV infection in a subject. Symptoms of RSV are well known in the art. They include rhinorrhea, sore throat, headache, hoarseness, cough, sputum, fever, rales, wheezing, and dyspnea. Thus, the method of the invention comprises the prevention or reduction of at least one symptom associated with RSV infection. A reduction in a symptom may be determined subjectively or objectively, e.g., self assessment by a subject, by a clinician's assessment or by conducting an appropriate assay or measurement (e.g. body temperature), including, e.g., a quality of life assessment, a slowed progression of a RSV infection or additional symptoms, a reduced severity of a RSV symptoms or a suitable assays (e.g. antibody titer and/or T-cell activation assay). The objective assessment comprises both animal and human assessments.

This invention is further illustrated by the following examples that should not be construed as limiting. The contents of all references, patents and published patent applications cited throughout this application, as well as the Figures and the Sequence Listing, are incorporated herein by reference for all purposes.

EXAMPLES

Example 1

Generating Recombinant Bacmids, Transfection of Insect Cells to Make Recombinant Virus Stocks, Plaque Purification, and Infecting Insect Cells with Primary Virus Stock To construct recombinant virus, the viral genes of interest were codon optimized for Sf9 insect cells expression and cloned into pFastBac™ vectors.

Once the desired constructs were confirmed and purified, one vial of MAX Efficiency® DH10Bac™ competent cells for each construct was thawed on ice. Approximately 1 ng (5 µl) of the desired pFastBac™ construct plasmid DNA was added to the cells and mixed gently. The cells were incubated on ice for 30 minutes. This was followed by heat-shock of the cells for 45 seconds at 42° C. without shaking. Next, the tubes were transferred to ice and chilled for 2 minutes. Subsequently 900 µl of room temperature S.O.C. Medium was added to each tube. The tubes were put on a shaker at 37° C. at 225 rpm for 4 hours. For each pFastBac™ transformation, 10-fold serial dilutions of the cells (10-1, 10-2 and 10-3) was prepared using S.O.C. medium. Next, 100 µl of each dilution was plated on an LB agar plate containing 50 µg/ml kanamycin, 7 µg/ml gentamicin, 10 µg/ml tetracycline, 100 µg/ml Bluo-gal, and 40 µg/ml IPTG. The plates were incubated for 48 hours at 37° C. White colonies were picked for analysis.

Different bacmid DNAs from above were made for each construct and were isolated. These DNAs were precipitation and added to Sf9 cells for 5 hours.

Next, 30 ml of Sf9 insect cells ($2\times10^6$ cells/ml) were infected with baculovirus expressing viral proteins of interest with 0.3 ml of plaque eluate and incubated 48-72 hrs. Approximately 1 ml of crude culture (cells+medium) and clarified culture harvests were saved for expression analysis and the rest were saved for purification purposes.

Example 2

Expression, Purification, and Analysis of Modified HRSV F Proteins

Genes encoding modified HRSV F proteins of interest were synthesized in vitro as overlapping oligonucleotides, cloned and expressed in host cells. Cloning and expression of the modified RSV F genes were achieved following the methods known in the art.

Recombinant plaques containing viral proteins of interest were picked and confirmed. The recombinant virus was then amplified by infection of Sf9 insect cells. In some cases, Sf9 insect cells were co-infected by a recombinant virus expressing modified F protein and another recombinant virus expressing other viral proteins (e.g., BRSV M protein and/or HRSV N protein). A culture of insect cells was infected at ~3 MOI (Multiplicity of infection=virus ffu or pfu/cell) with baculovirus carrying the various constructs. The culture and supernatant were harvested 48-72 post-infection. The crude harvest, approximately 30 mL, was clarified by centrifugation for 15 minutes at approximately 800×g. The resulting crude cell harvests containing modified HRSV F protein were purified as described below.

Modified HRSV F proteins of interest were purified from the infected Sf9 insect cell culture harvests. Non-ionic surfactant Tergitol® NP-9 (Nonylphenol Ethoxylate) was used to in a membrane protein extraction protocol. Crude extraction was further purified by passing through anion exchange chromatography, lentil lectin affinity/HIC, and cation exchange chromatography.

Protein expression was analyzed by SDS-PAGE and stained for total proteins by coomassie stain. Equal volumes of cell samples from crude harvest and 2× sample buffer containing βME (beta-mercaptoethanol) were loaded, approximately 15 to 20 μl (about to 7.5 to 10 μl of the culture)/lane, onto an SDS Laemmli gel.

In some cases, instead of chromatography, modified. HRSV F proteins in the crude cell harvests were concentrated by 30% sucrose gradient separation method, and then were analyzed by SDS-PAGE stained with coomassie, or Western Blot using anti-RSV F monoclonal antibody.

Crude cell harvest containing modified recombinant F proteins, purified recombinant F proteins, or recombinant F proteins concentrated by sucrose gradient can be further analyzed by Western Blot using anti-RSV F monoclonal antibody and/or anti-RSV F polyclonal antibody.

Example 3

Modified HRSV F Gene Encoding F Protein BV #541

Initial attempts to express the full length HRSV F protein proved unsuccessful in achieving high levels of expression. The F gene sequence used in the expression was SEQ ID NO: 1 (wild type HRSV F gene, GenBank Accession No. M11486). It encodes an inactive precursor ($F_0$) of 574 aa. This precursor is cleaved twice by furin-like proteases during maturation to yield two disulfide-linked polypeptides, subunit $F_2$ from the N terminus and $F_1$ from the C terminus (FIG. 1). The two cleavages sites are at residues 109 and 136, which are preceded by furin-recognition motifs (RARR, aa 106-109 (SEQ ID NO: 23) and KKRKRR, aa 131-136 (SEQ ID NO: 24)). The F gene sequence of SEQ ID NO: 1 contains suboptimal codon usage for expression in Sf9 insect cells and harbors 3 errors, producing a protein that can exhibit less than optimal folding (SEQ ID NO: 2, GenBank Accession No. AAB59858). In addition, a possible Poly (A) adenylation site (ATAAAA) was identified at the region encoding the $F_2$ subunit. Moreover, the wild type F gene sequence is approximately 65% AT rich, while desired GC-AT ratio of a gene sequence in Sf9 insect cell expression system is approximately 1:1.

In attempt to overcome poor expression levels of HRSV F protein, a new F gene sequence was designed so that:
 (a) the three GenBank sequencing errors were corrected;
 (b) the cryptic poly (A) site at the region encoding F2 subunit was modified;
 (c) F gene codons were optimized; and
 (d) the F gene encodes a modified F protein with inactivated primary cleavage site.

The three corrected amino acids errors were P102A, I379V, and M447V. The cryptic poly (A) site in the HRSV F gene was corrected without changing the amino acid sequence.

The codon optimization scheme was based on the following criteria: (1) abundance of aminoacyl-tRNAs for a particular codon in Lepidopteran species of insect cells for a given amino acid as described by Levin, D. B. et al, (Journal of General Virology, 2000, vol. 81, pp. 2313-2325), (2) maintenance of GC-AT ratio in gene sequences at approximately 1:1, (3) minimal introduction of palindromic or stem-loop DNA structures, and (4) minimal introduction of transcription and post-transcription repressor element sequences. An example of optimized F gene sequence was shown as SEQ ID NO: 19 (RSV-F BV #368).

To inactivate the primary cleavage site (1° CS. KKRKRR, aa 131-136) of HRSV F protein, the furin recognition site was mutated to either KKQKQQ (SEQ ID NO: 28) or GRRQQR (SEQ ID NO: 29). Several modified F proteins with such cleavage site mutations were evaluated to determine the efficiency of cleavage prevention. FIG. 2 shows several of the modified F proteins that were evaluated. The results indicate that the primary cleavage site of HRSV F protein can be inactivated by three conservative amino acid changes R133Q, R135Q, and R136Q. These conservative amino acid changes from Arginine (R) which is a polar-charged molecule, to Glutamine (Q) which is a polar-neutral molecule, altered the charge status at these sites and prevented cleavage by furin-like proteases (see FIG. 3), while still preserving the F protein 3D structure. Prevention of cleavage at 1° CS resulted reduced membrane fusion activity of the F protein.

A non-limiting exemplary modified HRSV F gene sequence designed to have all modifications mentioned above is shown in FIG. 4. This modified F gene (SEQ ID NO: 5, RSV-F BV #541) encodes a modified F protein of SEQ ID NO: 6. The gene sequence was synthesized in vitro as overlapping oligonucleotides, cloned and expressed in host cells. Modified HRSV F protein BV #541 was purified from the infected Sf9 insect cell culture harvests, and was analyzed by SDS-PAGE stained by coomassie. The method of purification and SDS-PAGE analysis is described in Example 2. The expression level of the F protein RSV-F BV #541 (e.g. F protein 541 was improved as compared to the wild type $F_0$ protein in SF9 insect cells.

Example 4

Modified HRSV F Protein with $F_1$ Subunit Fusion Domain Partial Deletion

To further improve expression of the RSV F protein, additionally modified HRSV F genes were designed that comprised the following modifications:
 (a) the three GenBank sequencing errors were corrected;
 (b) the cryptic poly (A) site at the region encoding F2 subunit was modified;
 (c) F gene codons were optimized; and
 (d) the nucleotide sequences encoding the $F_1$ subunit fusion domain was partially deleted. In one experiment, the nucleotide sequence encoding the first 10 amino acids of the $F_1$ subunit fusion domain was deleted (corresponding to amino acids 137-146 of SEQ ID NO: 2).

Figure 5:
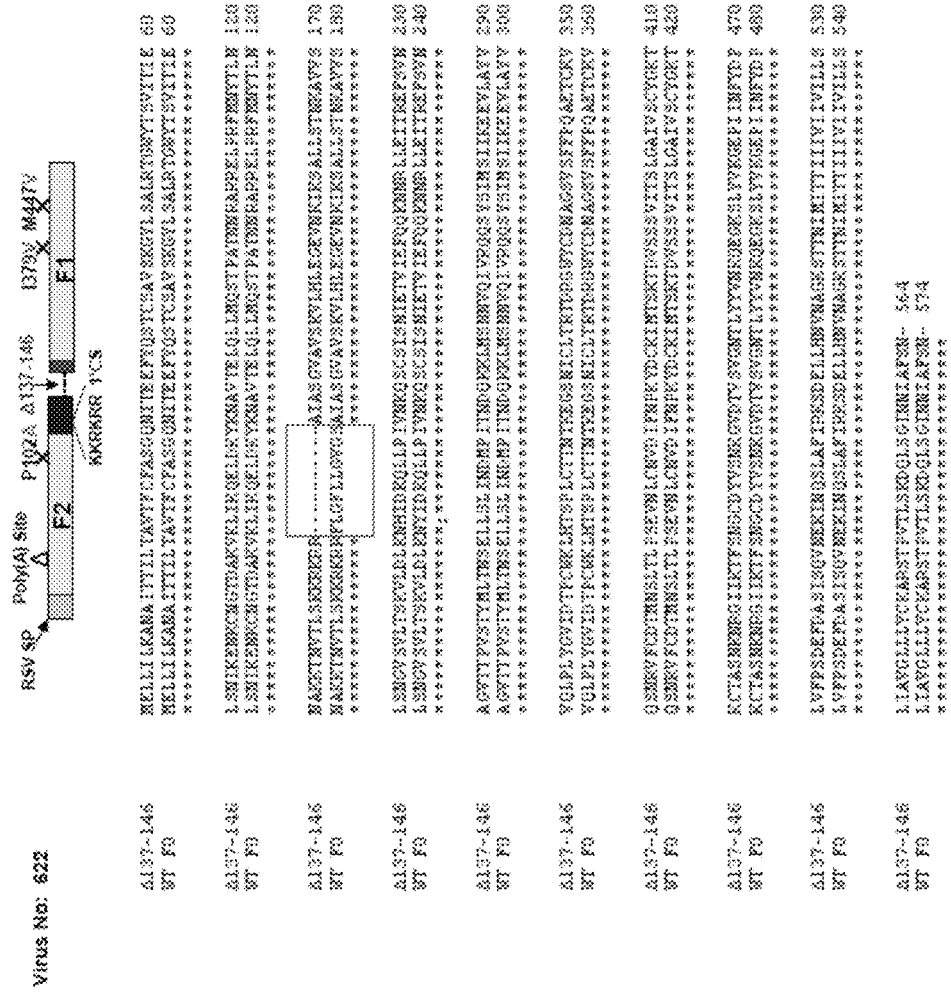
FIG. 5 depicts sequence and structure of modified HRSV F protein BV #622 (SEQ ID NO: 10), and the KKRKRR cleavage site (SEQ ID NO:24)
Figure 6:
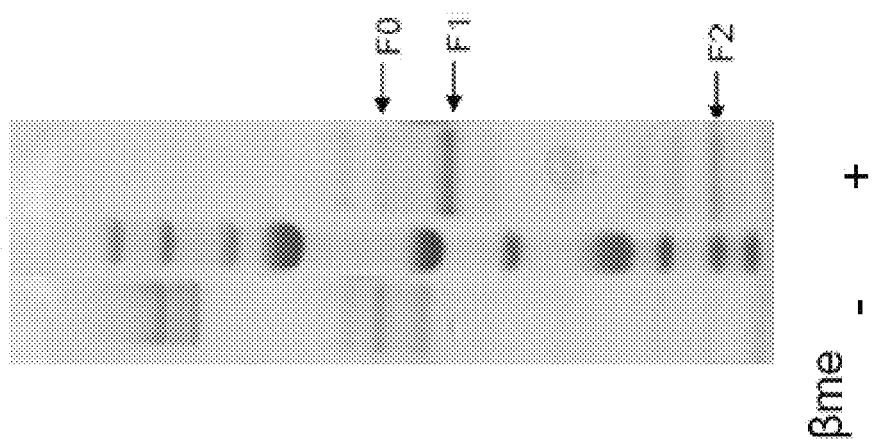
FIG. 6 depicts SDS-PAGE coomassie-stained gel of purified recombinant HRSV F protein BV #622 with or without the presence of βME.

A non-limiting exemplary modified. RSV F gene comprising said modifications is shown in FIG. 5, designated as SEQ ID NO: 9 (RSV-F BV #622, e.g. F protein 622), encoding a modified F protein of SEQ ID NO: 10. The modified HRSV F protein BV #622 was purified from the infected SF9 insect cell culture harvests, and was analyzed by SDS-PAGE stained with coomassie. The method of purification and SDS-PAGE analysis is described in Example 2. High expression levels of HRSV F protein BV #622 were observed, as displayed in the SDS-PAGE FIG. 6.

Example 5

Modified HRSV F Protein with Both Inactivated Primary Cleavage Site and $F_1$ Fusion Domain Partial Deletion To determine if the combination of inactivated primary cleavage site and $F_1$ fusion domain partial deletion can further promote expression of the RSV F protein, particularly in the Sf9 insect cells, another modified RSV F gene was designed comprising following modifications:

(a) the three GenBank sequencing errors were corrected;
(b) the cryptic poly (A) site at the region encoding F2 subunit was modified;
(c) F gene codons were optimized;
(d) the primary cleavage site was inactivated; and
(e) the nucleotide sequence encoding the F1 subunit fusion domain was partially deleted. In one experiment, the nucleotide sequence encoding the first 10 amino acids of the $F_1$ subunit fusion domain was deleted (corresponding to amino acids 137-146 of SEQ ID NO: 2).

Figure 8:
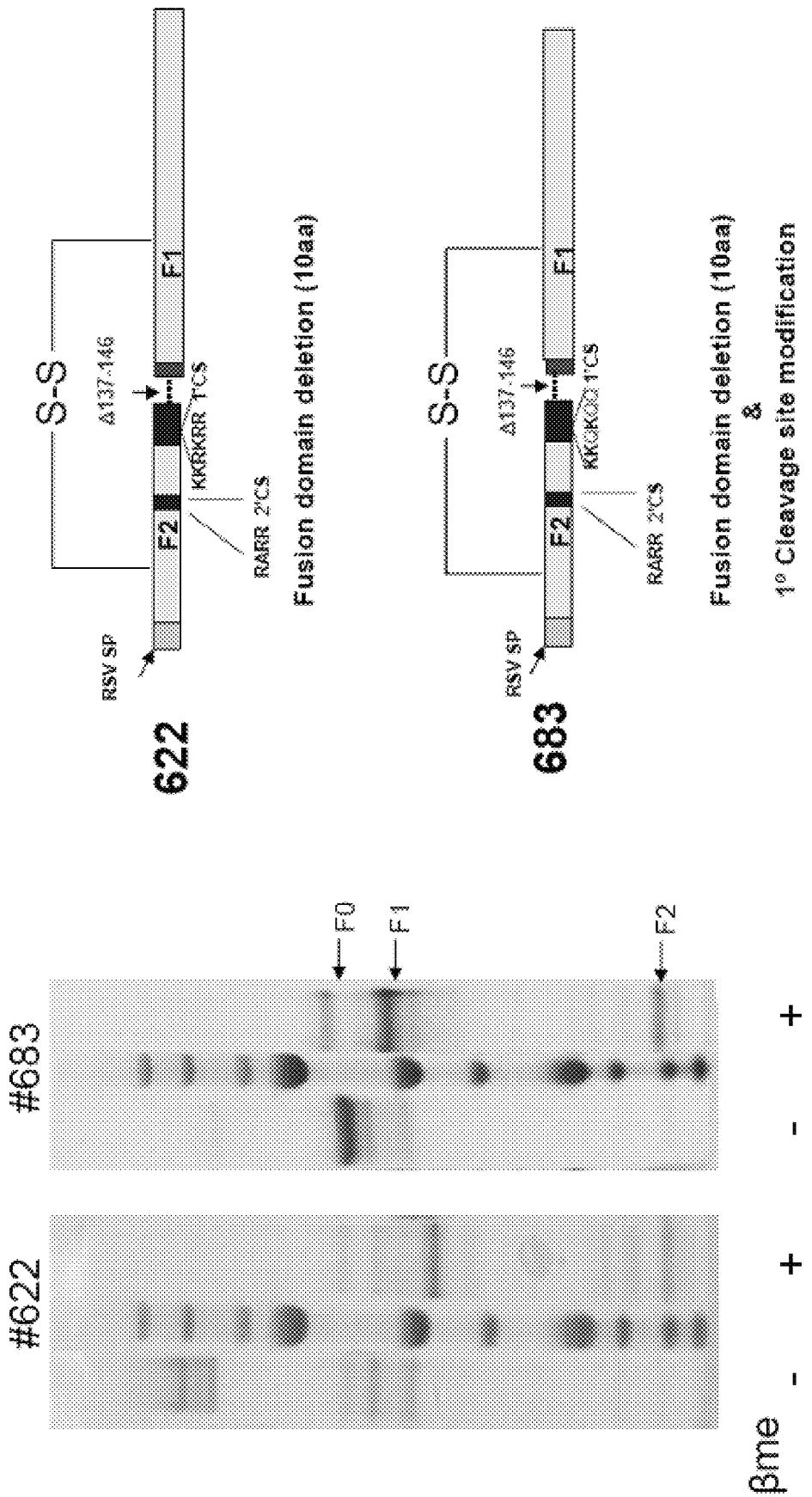
FIG. 8 depicts SDS-PAGE coomassie-stained gels of purified recombinant HRSV F proteins BV #622 and BV #683 with or without the presence of βME (on the left), and their structures; as well as the KKQKQQ cleavage site (SEQ ID NO:28) and the KKRKRR cleavage site (SEQ ID NO:24).

An non-limiting exemplary modified RSV F gene comprising said modifications is shown in FIG. 7, designated as SEQ ID NO: 7 (RSV-F BV #683, e.g. F protein 683), encoding the modified F protein of SEQ ID NO: 8. The modified RSV F protein BV #683 (e.g. F protein 683) was purified from the infected Sf9 insect cell culture harvests and analyzed by SDS-PAGE stained with coomassie. The method of purification and SDS-PAGE analysis is described in Example 2. Further enhancements in the of expression levels were achieved, as displayed in the SDS-PAGE in FIG. 8.

Example 6

Expression and Purification of Modified HRSV F Protein BV #683

Modified HRSV F protein BV #683 (e.g. F protein 683, SEQ ID NO: 8) was expressed in baculovirus expression system as describe in Example 1, and recombinant plaques expressing HRSV F protein BV #683 were picked and confirmed. The recombinant virus was then amplified by infection of Sf9 insect cells. A culture of insect cells was infected at ~3 MOI (Multiplicity of infection=virus ffu or pfu/cell) with baculovirus. The culture and supernatant were harvested 48-72 hrs post-infection. The crude harvest, approximately 30 mL, was clarified by centrifugation for 15 minutes at approximately 800×g. The resulting crude cell harvests containing HRSV F protein BV #683 were purified as described below.

HRSV F protein BV #683 was purified from the infected Sf9 insect cell culture harvests. Non-ionic surfactant Tergitol® NP-9 (Nonylphenol Ethoxylate) was used to in a membrane protein extraction protocol. Crude extraction was further purified by passing through anion exchange chromatography, lentil lectin affinity/HIC and cation exchange chromatography.

Figure 9:
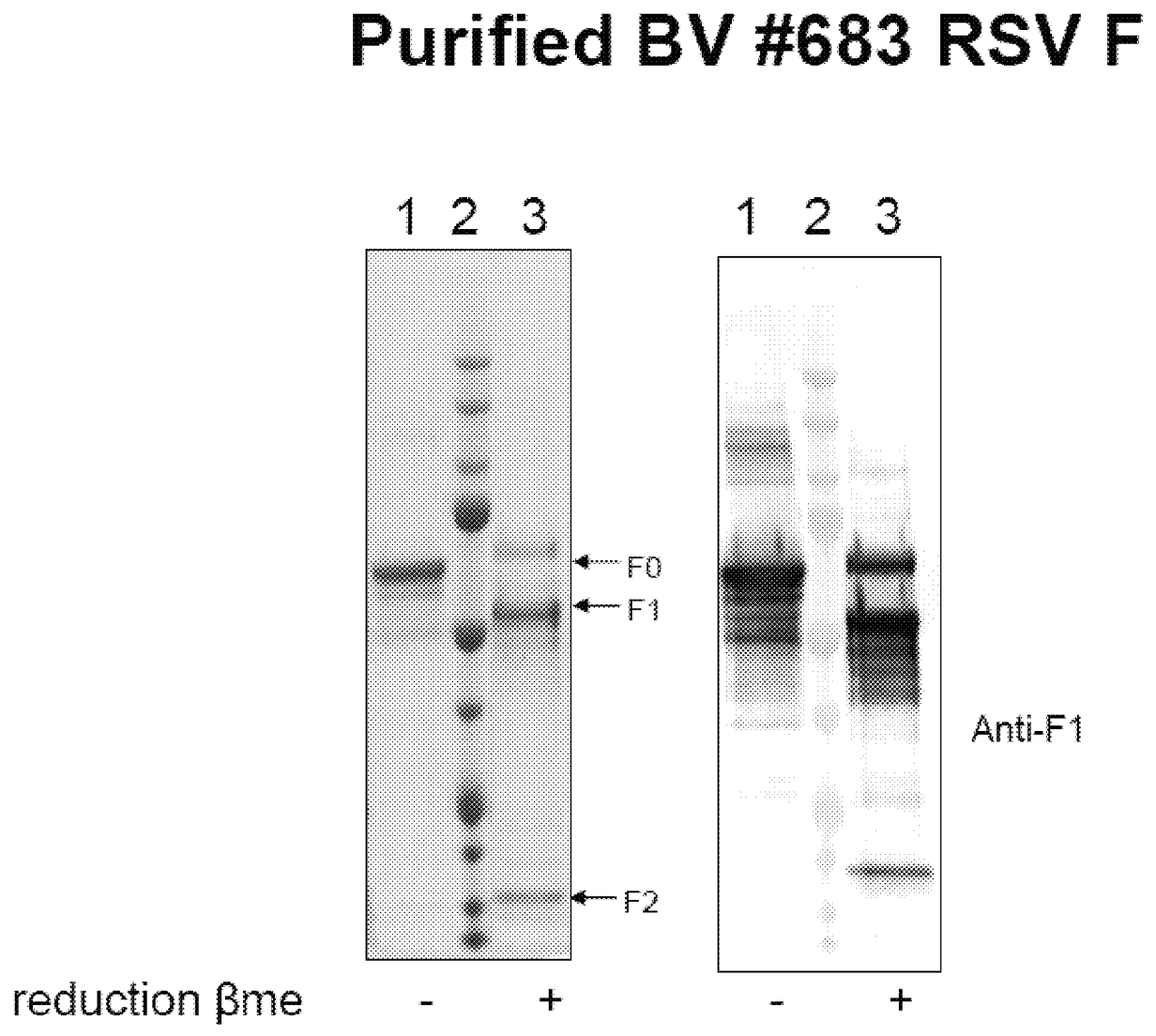
Figure 10:
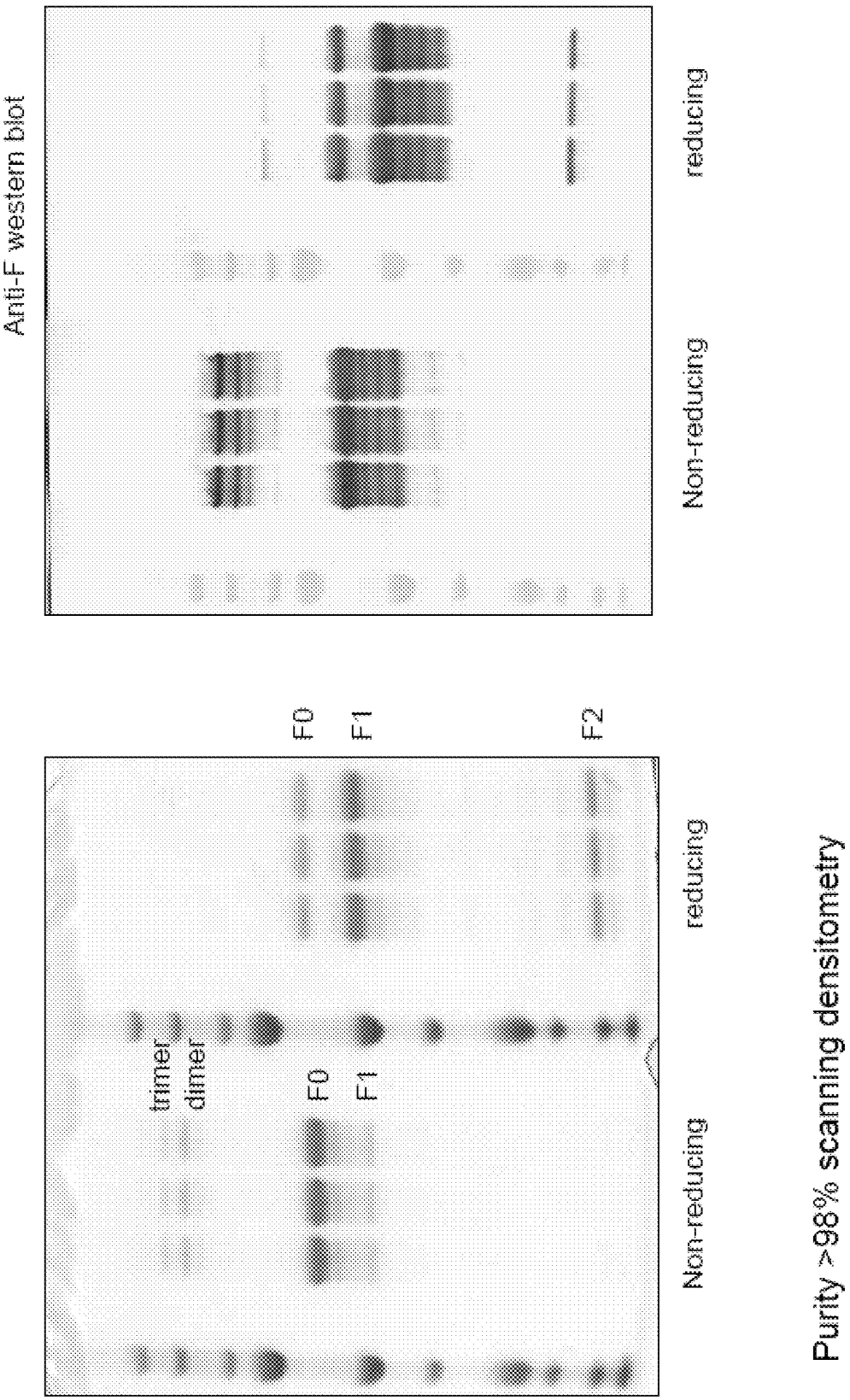
FIG. 10 depicts SDS-PAGE coomassie-stained gel used in purity analysis by scanning densitometry (on the left) and Western Blot (on the right) of purified recombinant HRSV F protein BV #683.

Purified HRSV F protein BV #683 was analyzed by SDS-PAGE stained with coomassie, and Western Blot using anti-RSV F monoclonal antibody as described in Example 2. The results were shown in FIG. 9. Excellent expression levels of the HRSV F protein BV #683 (e.g. F protein 683, SEQ ID NO: 8) were achieved. It was estimated that the expression level was above 10 mg/L in crude cell culture, and recovered F protein BV #683 was about 3.5 mg/L cell culture. In some cases expression levels above 20 mg/L were achieved and about 5 mg/L modified F protein BV #683 was recovered (see FIG. 10). Purity of the recovered F protein BV #683 reached above 98% as determined by scanning densitometry (see FIG. 10).

Example 7

Purified HRSV F Protein BV #683 Micelles (Rosettes)

Figure 12:
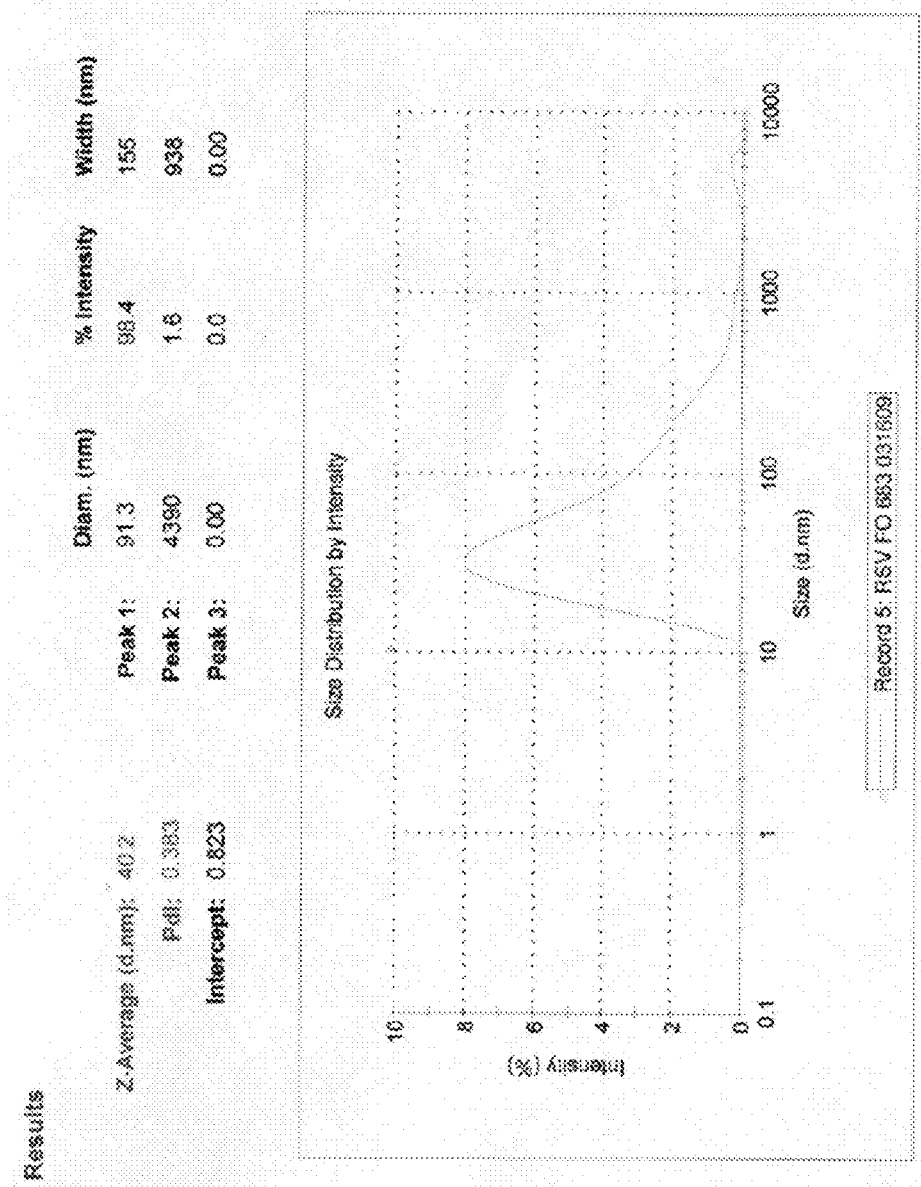
FIG. 12 depicts particle size analysis of HRSV F protein BY #683 micelles.

Purified HRSV F protein BV #683 was analyzed by negative stain electron microscopy (see FIG. 11). F proteins aggregated in the form of micelles (rosettes), similar to those observed for wild type HRSV F protein (Calder et al., 2000, Virology 271, pp. 122-131), and other full-length virus membrane glycoproteins (Wrigley et al., Academic Press, London, 1986. vol. 5, pp. 103-163). Under electron microscopy, the F spikes exhibited lollipop-shaped rod morphology with their wider ends projecting away from the centers of the rosettes. The length of single trimer was about 20 nm, and the micelle particle diameter was about 40 nm (see FIG. 12). These results indicated that HRSV F protein BV #683 has correct 3D structure for a native, active protein.

In summary, a modified recombinant HRSV F protein (e.g., BV #683) has been designed, expressed, and purified. This modified full-length F is glycosylated. Modifications of the primary cleavage site and the fusion domain together greatly enhanced expression level of F protein. In addition, this modified F protein can be cleaved to $F_1$ and $F_2$ subunits, which are disulfide-linked. Trimers of the $F_1$ and $F_2$ subunits form lollipop-shaped spikes of 19.6 nm and particles of 40.2 nm. Moreover, this modified F protein is highly expressed in Sf9 insect cells. Purity of micelles >98% is achieved after purification. The fact that the spikes of this modified protein have a lollipop morphology, which can further form micelles particles of 40 nm, indicates that modified F protein BV #683 has correct 3D structure of a native protein.

Example 8

Co-Expression of Modified HRSV F Protein with BRSV M and/or HRSV N in VLP Production The present invention also provides VLPs comprising a modified or mutated RSV F protein. Such VLPs are useful to induce neutralizing antibodies to viral protein antigens and thus can be administered to establish immunity against RSV. For example, such VLPs may comprise a modified RSV F protein, and a BRSV M and/or HRSV N proteins. Codons of genes encoding BRSV M (SEQ ID NO: 14) or HRSV N (SEQ ID NO: 18) proteins can be optimized for expression in insect cells. For example, an optimized BRSV M gene sequence is shown in SEQ ID NO: 13 and an optimized RSV N gene sequence is shown in SEQ ID NO: 17.

Figure 13:
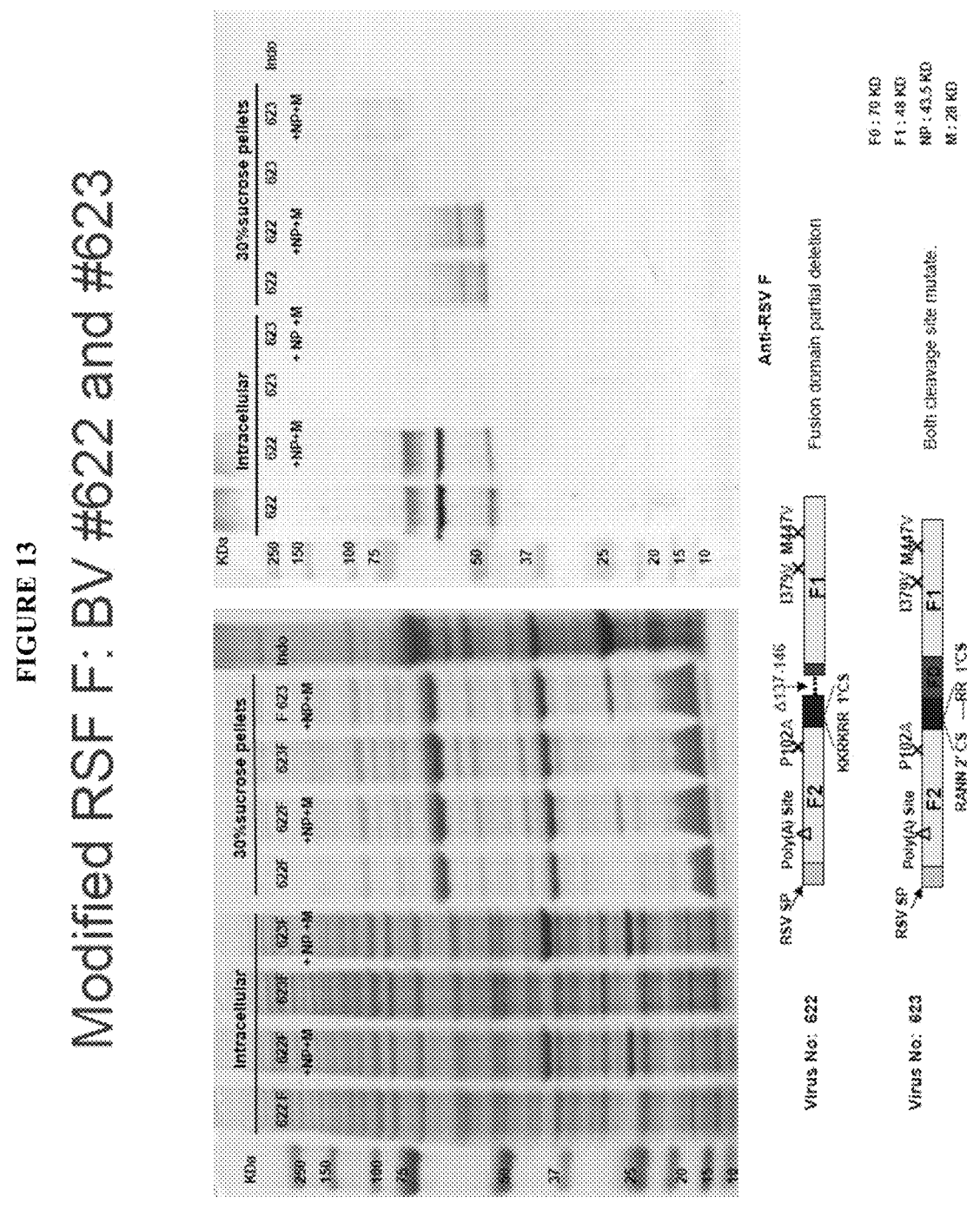

In one experiment, a modified F protein BV #622 and another modified F protein BV #623 (SEQ ID NO: 21, modified such that both cleavage sites are inactivated) were either expressed alone, or co-expressed with HRSV N protein and BRSV M protein. Both crude cell harvests containing VLPs (intracellular) and VLPs pellets collected from 30% sucrose gradient separation were analyzed by SDS-PAGE stained with coomassie, and Western Blot using anti-RSV F monoclonal antibody. FIG. 13 shows the structure of the modified F proteins BV #622 and BV #623, and results of SDS-PAGE and Western Blot analysis. BV #622 was highly expressed by itself or co-expressed with HRSV N protein and BRSV M protein, while BV #623 had very poor expression, indicating inactivation of both cleavage sites inhibits F protein expression.

Figure 14:
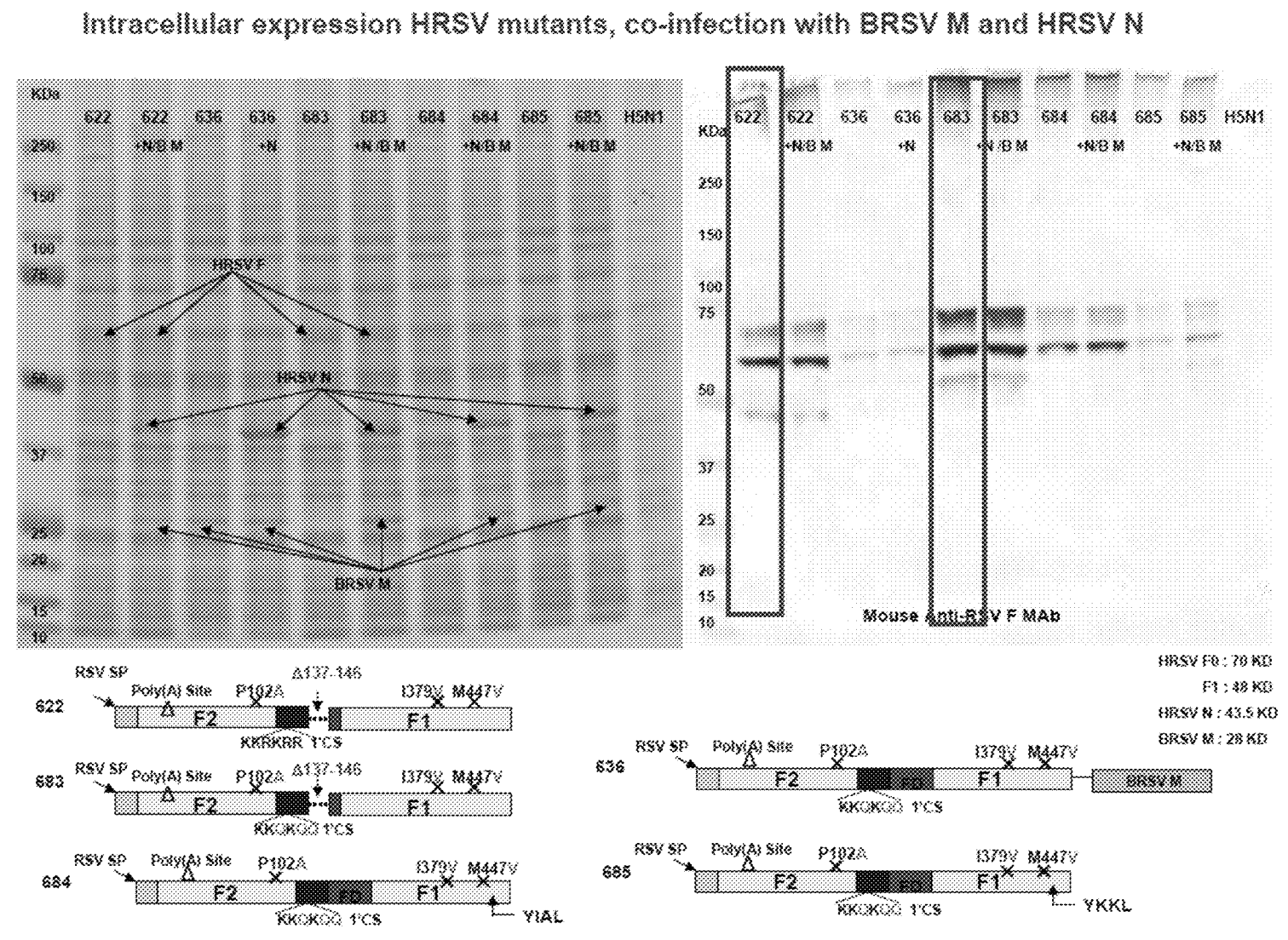
Figure 15:
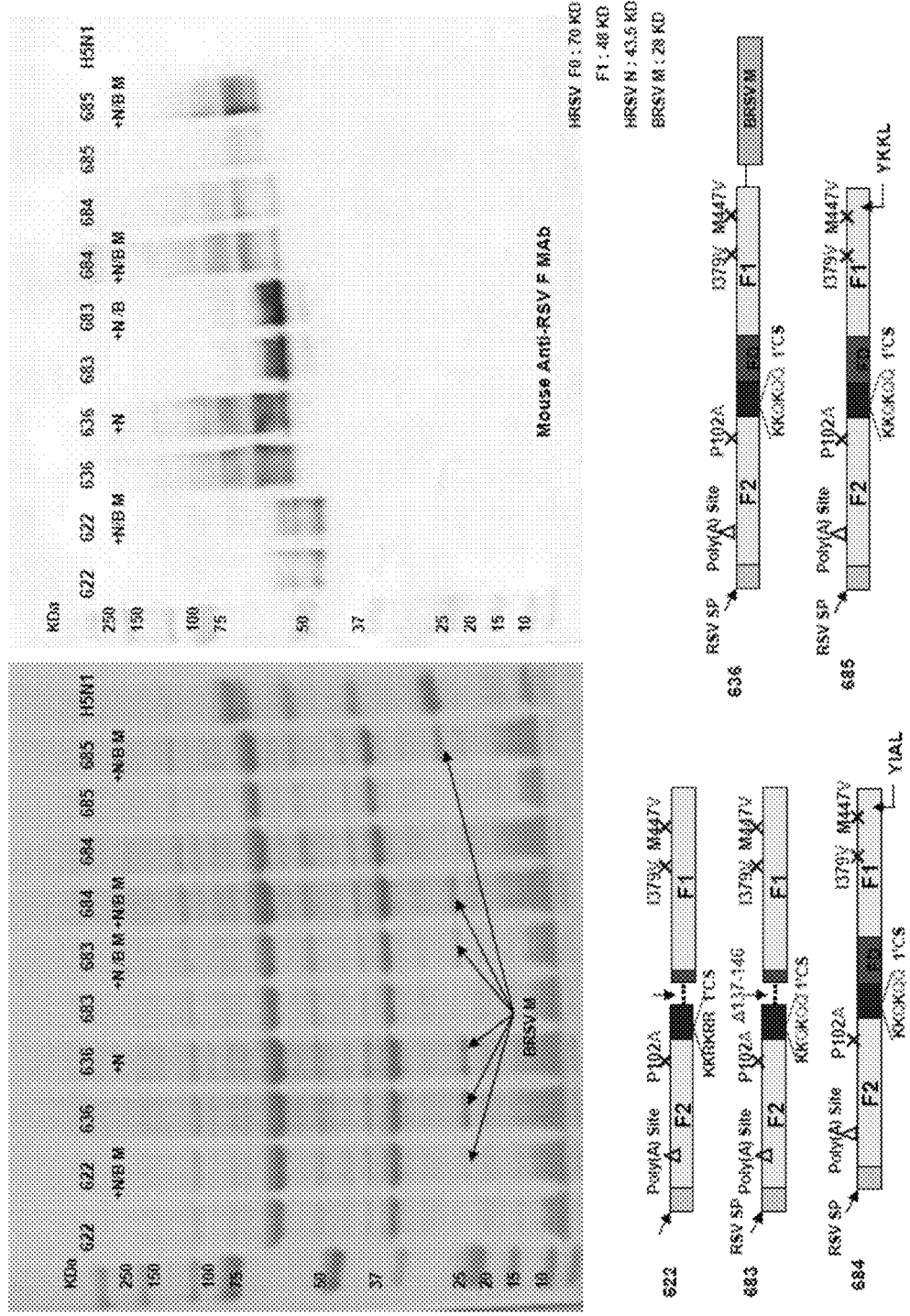
FIG. 15 depicts SDS-PAGE coomassie-stained gel (on the left) and Western Blot (on the right) analysis of modified RSV F protein BV #622 (SEQ ID NO: 10), double tandem chimeric BV #636 (BV #541 +BRSV M), BV #683 (SEQ ID NO: 8), BV #684 (BV #541 with YIAL L-domain), and BV #685 (BV #541 with YKKL L-domain) with or without co-expression with HRSV N and BRSV M proteins in the pelleted samples by 30% sucrose gradient separation, and structure of each analyzed modified HRSV F protein. Also featured is the KKQKQQ cleavage site (SEQ ID NO:28), and the KKRKRR cleavage site (SEQ ID NO:24).
Figure 16A:
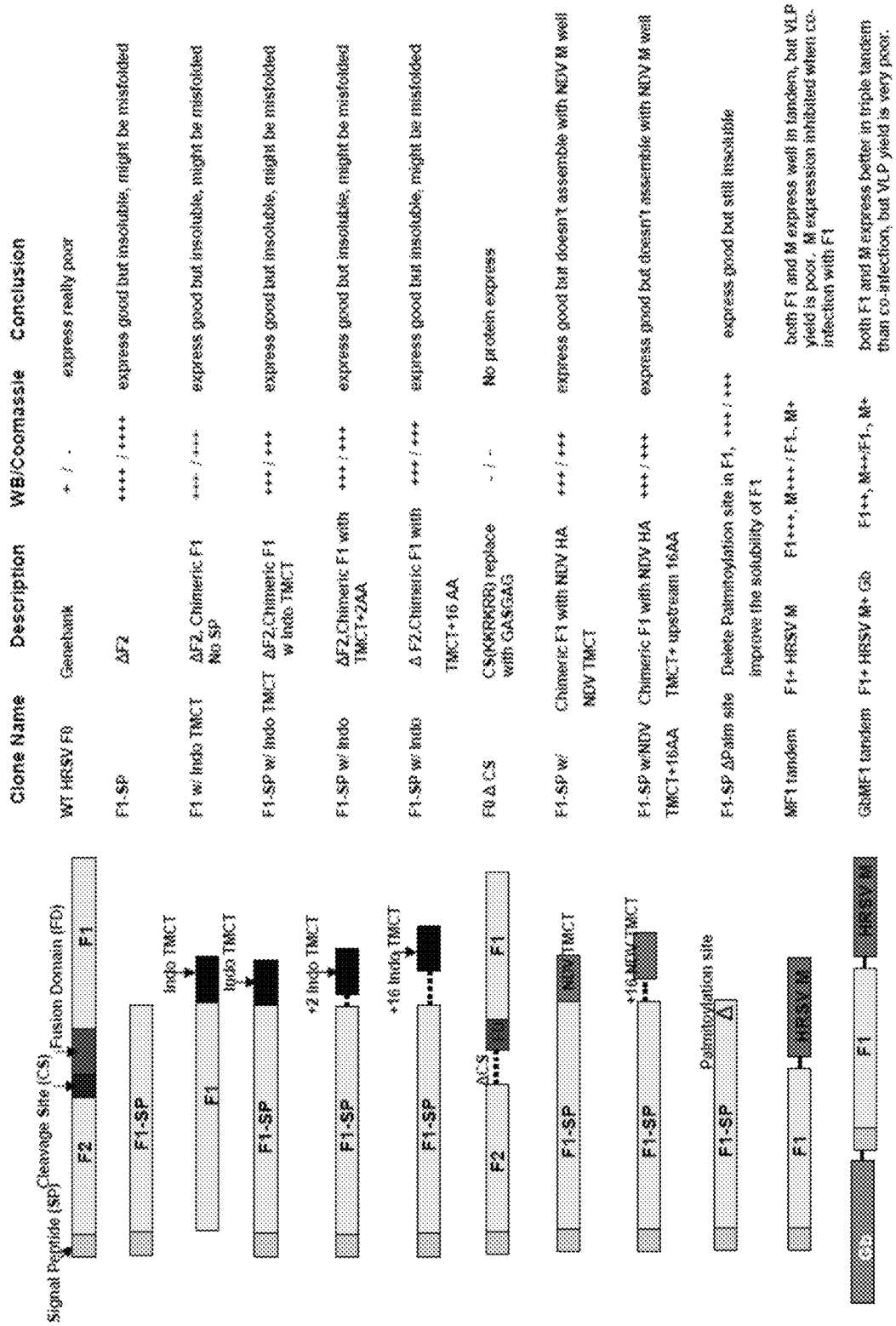

In another experiment, modified F protein BV #622, double tandem gene BV #636 (BV #541+BRSV M), BV #683, BV #684 (BV #541 with YIAL L-domain introduced at the C terminus), and BV #685 (BV #541 with YKKL L-domain introduced at the C terminus) were either expressed alone, or co-expressed with HRSV N protein and BRSV M protein. L-domain (Late domain) is conserved sequence in retroviruses, and presents within Gag acting in conjunction with cellular proteins to efficiently release virions from the surface of the cell (Ott et al., 2005, *Journal of Virology* 79: 9038-9045). The structure of each modified F protein is shown in FIG. 14. Both crude cell harvests containing VLPs (intracellular) and VLPs pellets collected from 30% sucrose gradient separation were analyzed by SDS-PAGE stained with coomassie, and Western Blot using anti-RSV F monoclonal antibody. FIG. 14 shows the results of SDS-PAGE and Western Blot analysis of crude cell harvests containing VLPs (intracellular), and FIG. 15 showed results of SDS-PAGE and Western Blot analysis of VLPs pellets collected from 30% sucrose gradient separation. BV #622 and BV #683 were highly expressed by themselves or co-expressed with HRSV N protein and BRSV M protein, while BV #636, BV #684, and BV #685 had poor expression.

Example 9

Screening of Chimeric HRSV F Proteins with High Expression

Efforts were made to screen for additional RSV F proteins that can be highly expressed in soluble form in insect cells and can form VLPs with better yield. Various F genes were designed, expressed, and analyzed. Both Western Blot and SDS-PAGE were used to evaluate the expression.

FIG. 16a to FIG. 16d summarize the structure, clone name, description, Western Blot/coomassie analysis results, and conclusion for each chimeric HRSV F clone.

As the results indicated, wild type full length F protein was poorly expressed; chimeric HRSV F proteins that contain $F_1$ but not $F_2$ subunit could be expressed well, but the products were either insoluble, which might be due to misfolding, or could not assemble with other viral proteins to form VLPs with good yield after co-infections. Inactivation of the primary cleavage site alone did not result in substantial increases in expression, but better expression was achieved when inactivation of the primary cleavage site was combined with other modification such as deletion of cryptic poly (A) site and correction of GenBank aa errors e.g., BV #541). Introduction of the YKKL L-domain into the C terminus of BV #541 enhanced the secretion of VLPs containing modified F protein for about 2-3 folds in co-expression with BRSV M and HRSV N proteins. The results further showed that a double tandem chimeric gene consisting of BV #541 gene and BRSV M gene displayed both improved intracellular and VLPs yield compared to co-infection of BV #541 and BRSV M proteins, indicating that BRSV M protein can facilitate production of VLPs containing modified HRSV F protein in insect cells when tandemly expressed. A triple tandem chimeric gene consisting of BV #541, BRSV M, and HRSV N had even higher intracellular and much better VLPs yield compared to above mentioned double tandem chimeric gene or co-infection of BV #541, BRSV M, and HRSV N proteins. Furthermore; the results suggested that chimeric HRSV F protein BV #683 (e.g. F protein 683, SEQ ID NO: 8) had the best intracellular expression. Expression of a double tandem chimeric gene consisting of BV #683 and BRSV M genes, or a triple tandem chimeric gene consisting of BV #683, BRSV M, and HRSV N genes is also embodied herein. These double and triple tandem chimeric gene should further improve VLP production compared to co-infection.

Example 10

RSV Neutralization Assay and RSV Challenge Studies in Mice

Figure 17:
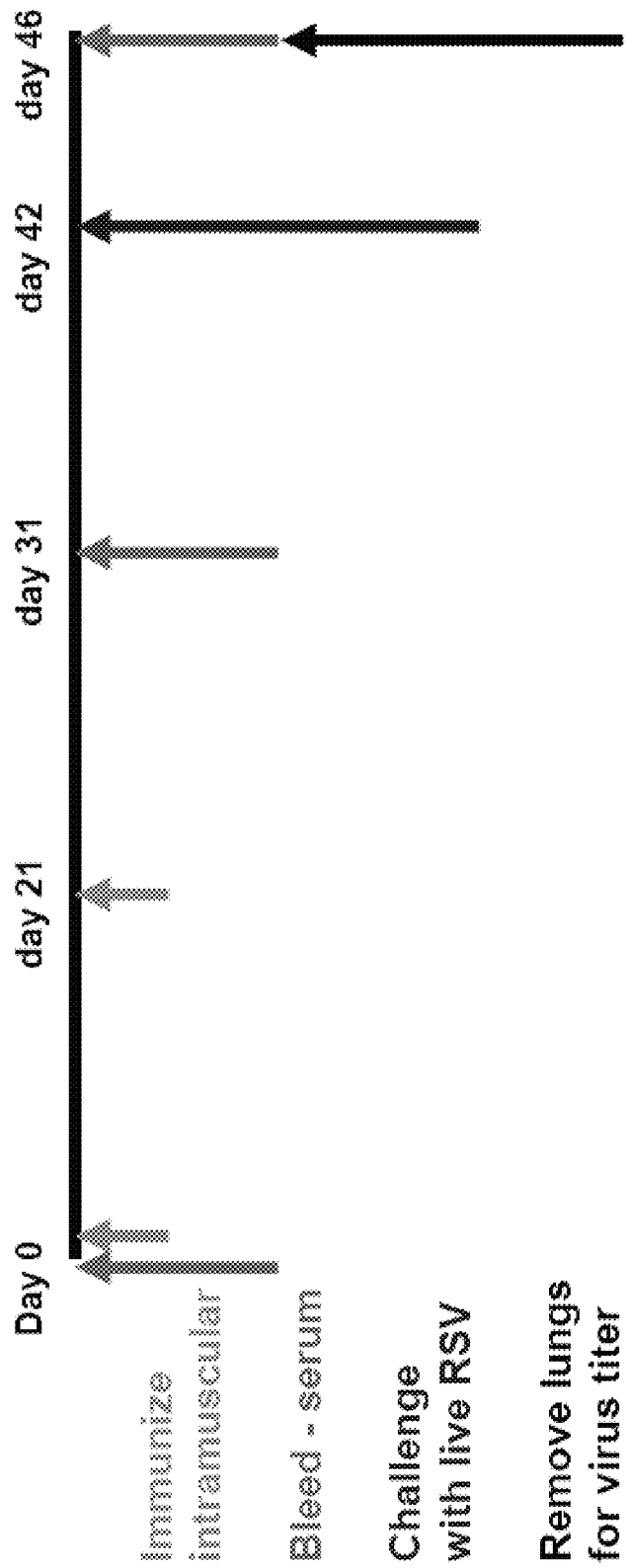
FIG. 17 depicts experimental procedures of the RSV challenge study as described in Example 10.

To test the efficiency of vaccine comprising modified HRSV F protein BV #683 in prohibiting RSV infection, neutralization assay and RSV challenge studies were conducted in mice. The experimental procedures are shown in FIG. 17.

Groups of mice (n=10) were injected intramuscularly (except for live RSV) with placebo (PBS solution), live RSV (given intranasally), formalin inactivated RSV vaccine (FI-RSV), 1 ug purified F particles (PFP, modified F protein BV #683), 1 ug purified F particles with Alum (PFP+Alum), 10 ug purified F particles, 10 ug purified F particles with Alum (PFP+Alum), or 30 ug purified F particles on day 0 and day 21. Each immunized group was challenged by live RSV on day 42 (21 days after the second immunization). Mouse serum from each group was harvested on day 0, day 31 (10 days after the second immunization), and day 46 (4 days following challenge with live RSV).

Figure 18:
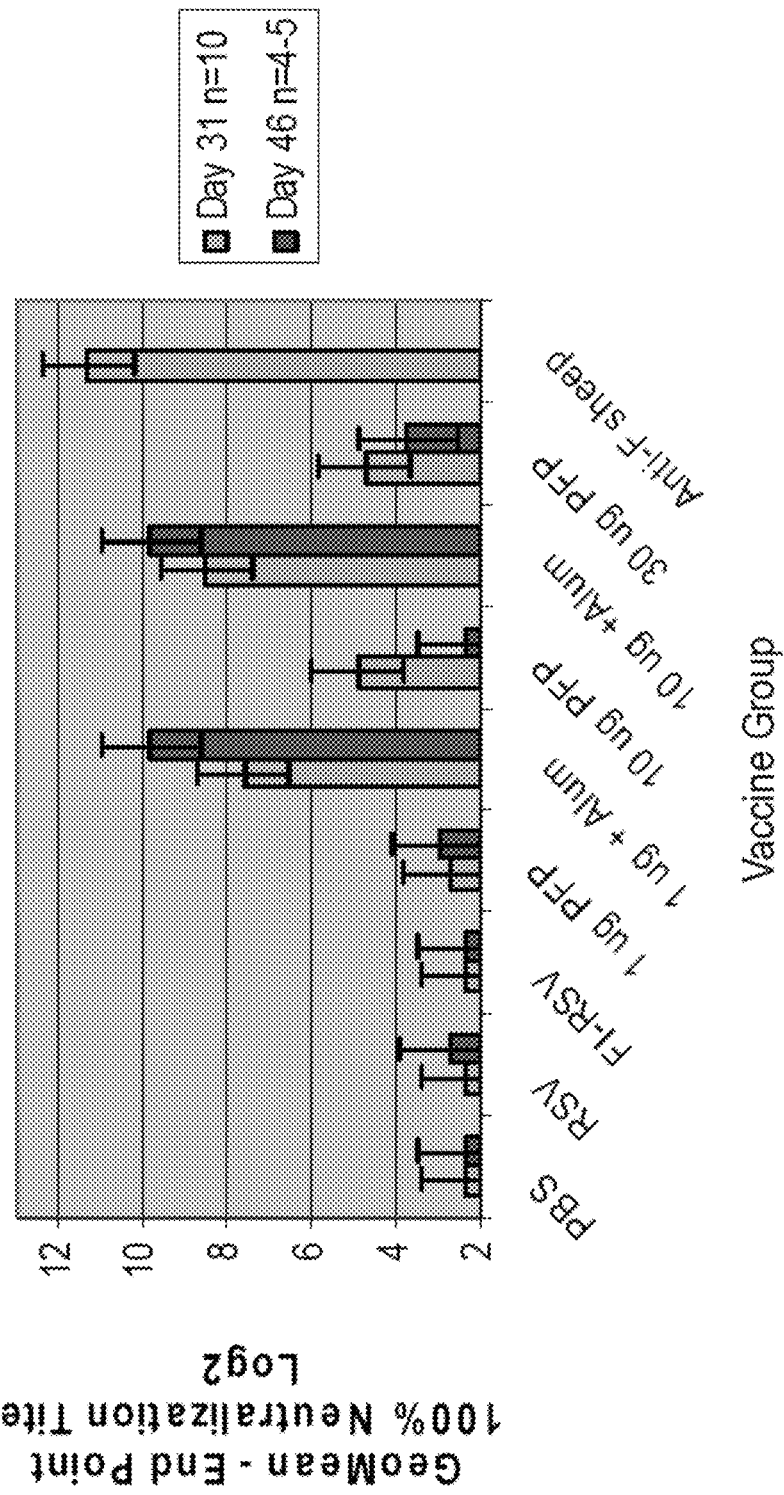
FIG. 18 depicts results of RSV neutralization assay at day 31 and day 46 of mice immunized with PBS, live RSV, FI-RSV, 1 ug PFP. 1 ug PFP+Alum, 10 ug PFP 10 ug PFP+Alum, 30 ug PEP, and positive control (anti-F sheep).
Figure 19:
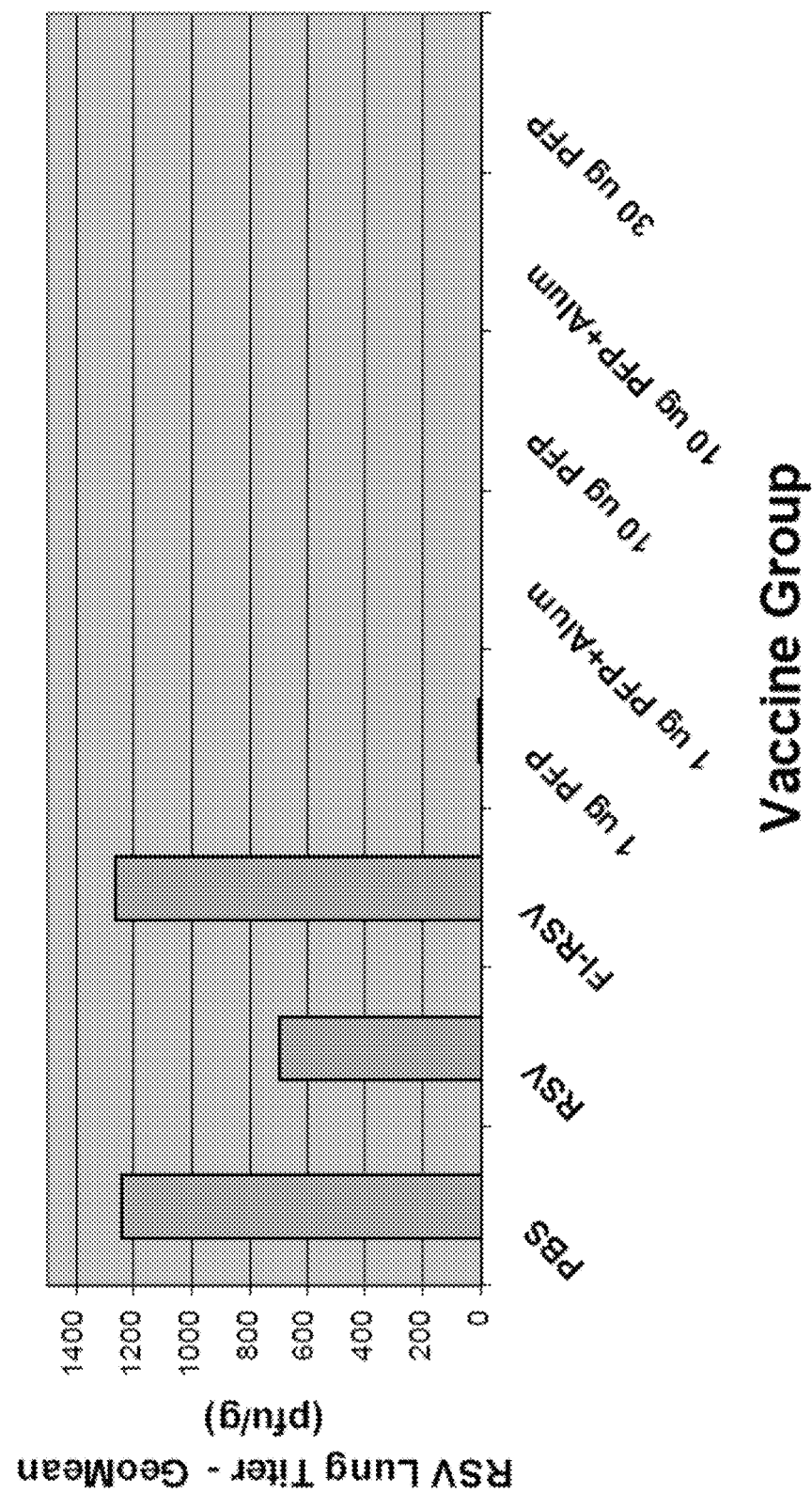
FIG. 19 depicts RSV titers in lung tissues of mice immunized with PBS live RSV, FI-RSV 1 ug PFP, 1 ug PFP+Alum, 10 ug PFP, 10 ug PFP+Alum and 30 ug PFP, 4 days after challenge of infectious RSV.

Mouse serum from each treatment group was assayed for the presence of anti-RSV neutralization antibodies. Dilutions of serum from immunized mice were incubated with infectious RSV in 96-well microtiter plates. Serum was diluted from 1:20 to 1:2560. 50 ul diluted serum was mixed with 50 ul live RSV virus (400 pfu) in each well. The virus/serum mixture was incubated first for 60 minutes at room temperature, and then mixed with 100 ul HEp-2 cells and incubated for 4 days. The number of infectious virus plaques were then counted after stained with crystal violet. The neutralization titer for each serum sample was defined as the inverse of the highest dilution of serum that produced 100% RSV neutralization (e.g., no plaques) and was determined for each animal. The geometric mean serum neutralizing antibody titer at day 31 (10 days after the boost) and day 46 (4 days following challenge with live RSV) were graphed for each vaccine group. FIG. 18 shows the results of neutralization assays. The results indicate that 10 ug or 30 ug purified F protein produce much higher neutralization titer as compared to live RSV. In addition, neutralization titers of PEP are enhanced with co-administration of Alum adjuvant, RSV challenge studies were carried out to determine if immunization could prevent and/or inhibit RSV replication in the lungs of the immunized animals. The amount of RSV in the lungs of immunized mice was determined by plaque assay using HEp-2 cells. Immunized groups of mice mentioned above were infected with $1 \times 10^6$ pfu of infectious RSV long strain intranasally on day 42 (11 days after the second immunization). On day 46 (4 days after RSV infection), lungs of mice were removed, weighed, and homogenized. Homogenized lung tissue was clarified. Supernatant of clarified solution was diluted and subjected to plaque assay using HEp-2 cells to determine RSV titer in lung tissue (calculated as pfu/g lung tissue). Results are shown in FIG. 19, indicating that all mice immunized with recombinant RSV F protein By #683 had undetectable RSV in the lungs, and even 1 ug purified recombinant HRSV F protein BV #683 without adjuvant exhibited excellent efficiency in inhibiting RSV replication (reduced more then 1000 times compared to placebo).

Figure 20:
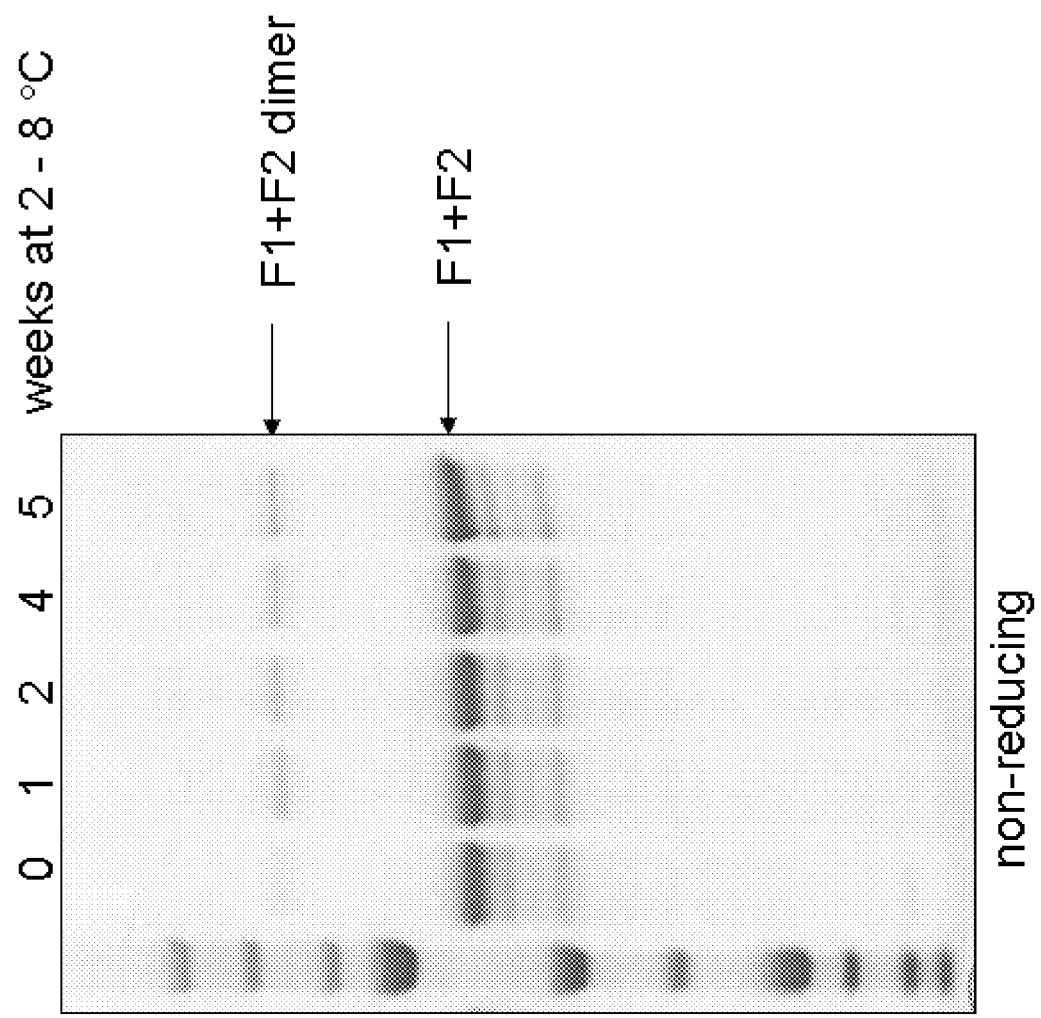
FIG. 20 depicts SDS-PAGE gel stained with coomassie of purified recombinant RSV F protein BV #683 stored at 2-8° C. for 0, 1, 2, 4, and 5 weeks.

To determine the stability of RSV PIT vaccine used above, the vaccine was stored at 2-8° C. for 0, 1, 2, 4, and 5 weeks, and then analyzed by SDS-PAGE stained with coomassie (FIG. 20). The results show that this RSV PFP vaccine is very stable at 2-8° C. and there is no detectable degradation.

Example 11

Recombinant RSV F Micelle Activity in Cotton Rats

In this example, animals groups included immunization at days 0 and 21 with live RSV (RSV), formalin inactivated RSV (FI-RSV), RSV-F protein BV #683 with and without aluminum (PFP and PFP+Aluminum Adjuvant), and PBS controls.

Figure 21:
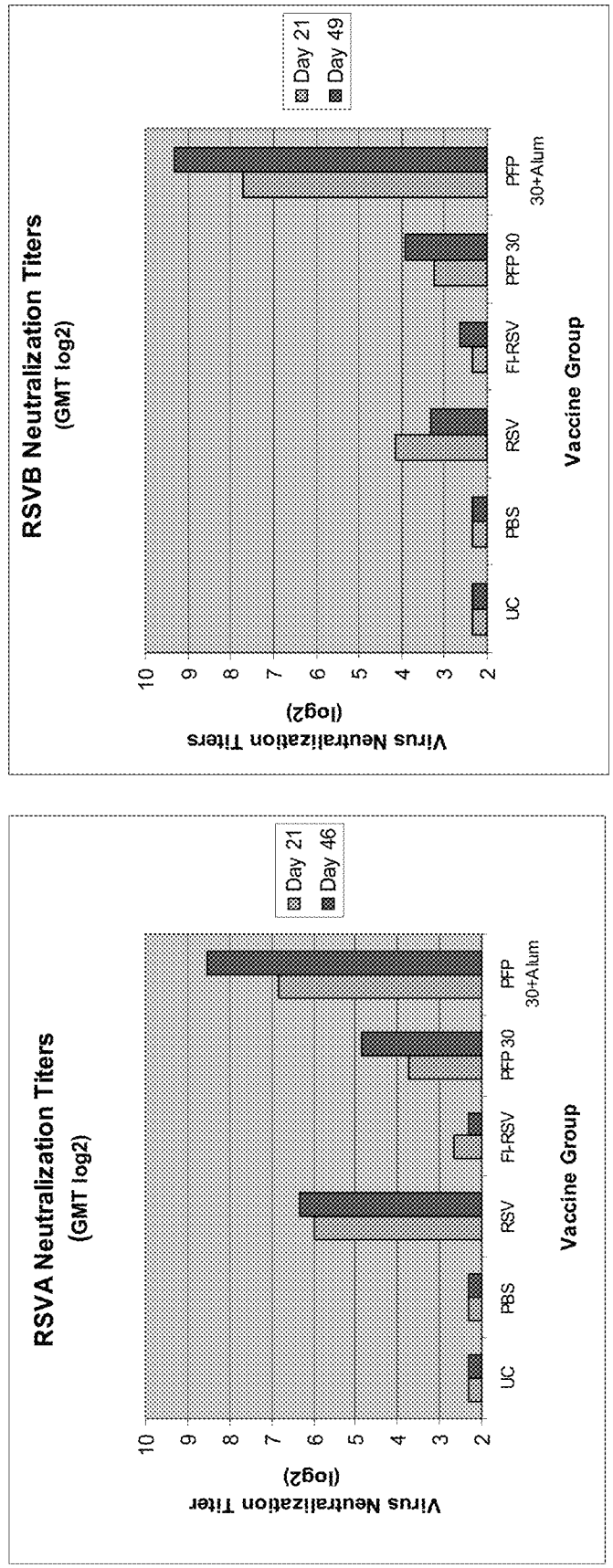
FIG. 21 depicts RSV A and RSV B neutralizing antibody responses following immunization with live RSV (RSV), formalin inactivated RSV (FI-RSV), RSV-F protein BV #683 with and without aluminum (PFP and PFP+Aluminum Adjuvant), and PBS controls.

As shown in FIG. 21, immunization with 30 ug of the F.-micelle vaccine (RSV-F protein BV #683, i.e. F protein 683, SEQ ID NO: 8), with and without aluminum produced robust neutralizing antibody responses following exposure to both RSV A and RSV B. In addition, it was observed that aluminum significantly enhances the antibody response. Moreover, neutralizing antibodies were increased following a boost at day 46 or day 49 in RSV A and RSV B, respectively.

Figure 22:
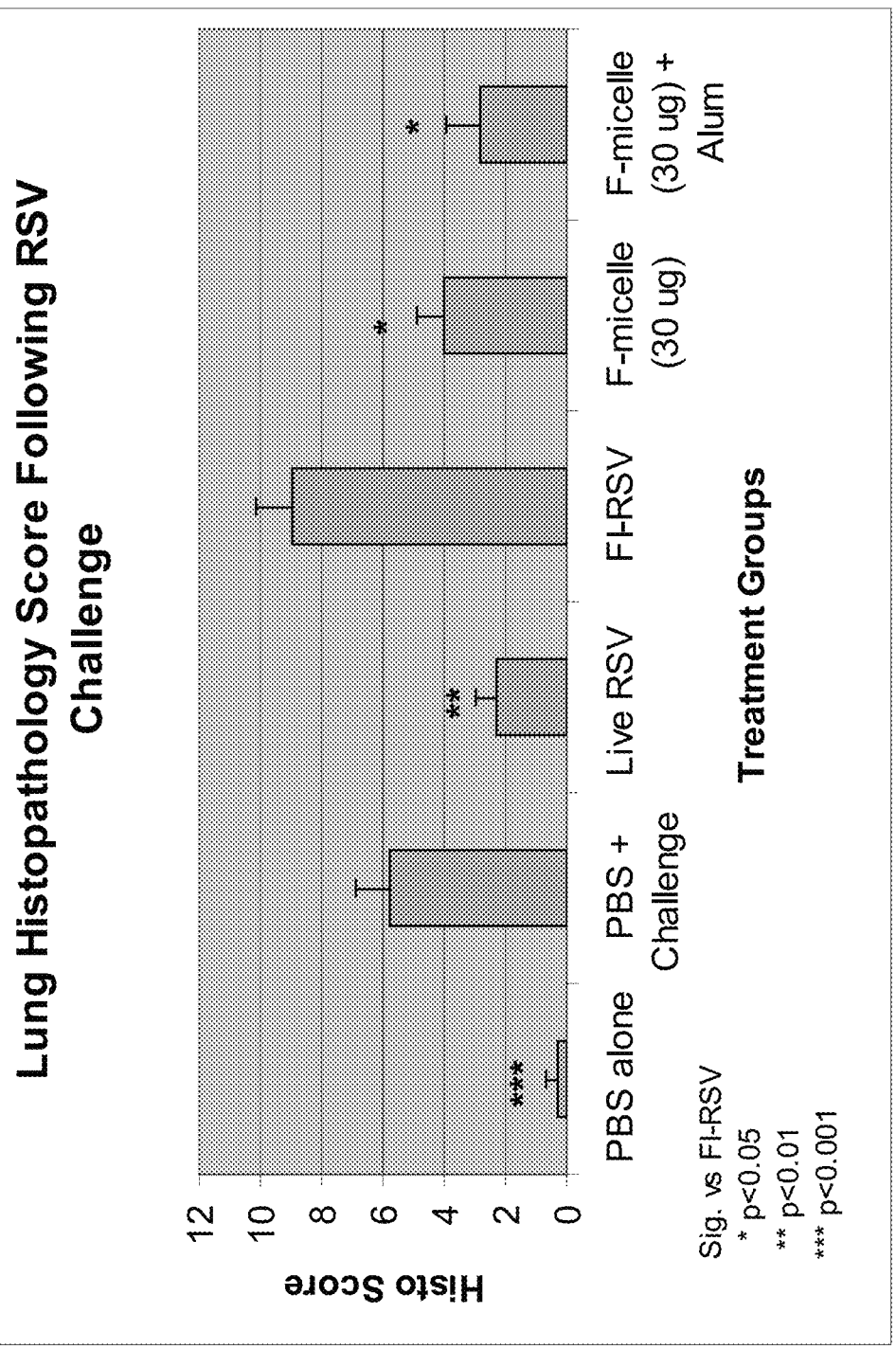
FIG. 22 depicts lung pathology following challenge with RSV in rats immunized with live RSV, formalin inactivated RSV (FI-RSV), RSV-F protein BV #683 with and without aluminum (F-micelle (30 ug) and F-micelle (30 ug)+Aluminum Adjuvant), and PBS controls.

While significant lung pathology was observed in rats immunized with formalin inactivated RSV (FI-RSV), no disease enhancement was seen with the F-micelle vaccine (FIG. 22). The use of the F-micelle vaccine and the F-micelle vaccine with adjuvant produced lower inflammation scores (4.0 and 2.8, respectively) than the primary RSV infection (PBS+RSV challenge) control group (5.8). As noted above, the FI-RSV treated group had a higher inflammation score than the primary RSV infection (PBS+RSV challenge) control group (9.0 versus 5.8). Moreover, the FI-RSV treated group had a significantly higher mean inflammation score (9.0) than the unchallenged placebo controls, live RSV+RSV challenge, F-micelle+RSV challenge, and F-micelle aluminum+RSV challenge.

The foregoing detailed description has been given for clearness of understanding only and no unnecessary limitations should be understood therefrom as modifications will be obvious to those skilled in the art. It is not an admission that any of the information provided herein is prior art or relevant to the presently claimed inventions, or that any publication specifically or implicitly referenced is prior art.

Unless defined otherwise, all technical and scientific terms used herein have the same meaning as commonly understood by one of ordinary skill in the art to which this invention belongs.

Although the application has been broken into sections to direct the reader's attention to specific embodiments, such sections should be not be construed as a division amongst embodiments. The teachings of each section and the embodiments described therein are applicable to other sections.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The invention claimed is:

1. An immunogenic formulation comprising a pharmaceutically acceptable carrier and a respiratory syncytial virus (RSV) F glycoprotein comprising:
   (i) an inactivated primary furin cleavage site; wherein the primary furin cleavage site is inactivated by amino acid substitution of one or more amino acids of arginine 133, arginine 135, and arginine 136;
   (ii) a wild-type secondary furin cleavage site having an amino acid sequence of RARR (SEQ ID NO: 23),
   (iii) a p27 protein; and
   (iv) a transmembrane domain;
   wherein the RSV F glycoprotein lacks an N-terminal signal peptide;
   wherein the RSV F glycoprotein is cleaved into F1 and F2 subunits which are disulfide linked;
   wherein the p27 protein is connected to the F1 subunit via an amide bond; and
   wherein the amino acids of the RSV F glycoprotein are numbered according to the RSV F glycoprotein of SEQ ID NO: 2.

2. The immunogenic formulation of claim 1, wherein one amino acid of arginine 133, arginine 135, and arginine 136 is substituted.

3. The immunogenic formulation of claim 1, wherein two amino acids of arginine 133, arginine 135, and arginine 136 are substituted.

4. The immunogenic formulation of claim 1, wherein each of arginine 133, arginine 135, and arginine 136 are substituted.

5. The immunogenic formulation of claim 2, wherein the one amino acid is substituted with glutamine.

6. The immunogenic formulation of claim 3, wherein the two amino acids are substituted with glutamine.

7. The immunogenic formulation of claim 4, wherein each of arginine 133, arginine 135, and arginine 136 are substituted with glutamine.

8. The immunogenic formulation of claim 1, wherein the RSV F glycoprotein comprises a deletion of the fusion domain corresponding to amino acids 137-146 of SEQ ID NO: 2.

9. The immunogenic formulation of claim 7, wherein the RSV F glycoprotein comprises a deletion of the fusion domain corresponding to amino acids 137-146 of SEQ ID NO: 2.

10. The immunogenic formulation of claim 1, comprising an adjuvant.

11. A method of eliciting an immune response to an RSV infection in a human comprising administering the immunogenic formulation of claim 1.

12. The method of claim 11, wherein the human is an infant.

13. The method of claim 11, wherein the administering is intramuscular.

14. The immunogenic formulation of claim 1, wherein the RSV F glycoprotein comprises up to four mutations relative to the RSV F glycoprotein of SEQ ID NO: 2.

* * * * *

SEQUENCE LISTING

```
Sequence total quantity: 35
SEQ ID NO: 1            moltype = DNA  length = 1725
FEATURE                 Location/Qualifiers
source                  1..1725
                        mol_type = other DNA
                        organism = Respiratory syncytial virus
SEQUENCE: 1
atggagttgc taatcctcaa agcaaatgca attaccacaa tcctcactgc agtcacattt    60
tgttttgctt ctggtcaaaa catcactgaa gaattttatc aatcaacatg cagtgcagtt   120
agcaaaggct atcttagtgc tctgagaact ggttggtata ccagtgttat aactatagaa   180
ttaagtaata tcaaggaaaa taagtgtaat ggaacagatg ctaaggtaaa attgataaaa   240
caagaattag ataaatataa aaatgctgta acagaattgc agttgctcat gcaaagcaca   300
ccaccaacaa acaatcgagc cagaagagaa ctaccaaggt ttatgaatta tactctcaac   360
aatgccaaaa aaaccaatgt aacattaagc aagaaaagga aagaagatt tcttggtttt   420
ttgttaggtg ttggatctgc aatcgccagt ggcgttgctg tatctaaggt cctgcaccta   480
gaagggaag tgaacaagat caaaagtgct ctactatcca caaacaaggc tgtagtcagc   540
ttatcaaatg gagttagtgt cttaaccagc aaagtgttag acctcaaaaa ctatatagat   600
aaacaattgt tacctattgt gaacaagcaa agctgcagca tcaaatat agaaactgtg   660
atagagttcc aacaaaagaa caacagacta ctagagatta ccagggaatt tagtgttaat   720
gcaggtgtaa ctacacctgt aagcacttac atgttaacta atagtgaatt attgtcatta   780
atcaatgata tgcctataac aaatgatcag aaaaagttaa tgtccaacaa tgttcaaata   840
gttagacagc aaagttactc tatcatgtcc ataataaag aggaagtctt agcatatgta   900
gtacaattac cactatatgg tgttatagat acacccctgt ggaaactaca cacatcccct   960
ctatgtacaa ccaacacaaa agaagggtcc aacatctgtt taacaagaac tgacagagga  1020
tggtactgtg acaatgcagg atcagtatct ttcttcccac aagctgaaac atgtaaagtt  1080
caatcaaatc gagtattttg tgacacaatg aacagtttaa cattaccaag tgaaataaat  1140
ctctgcaatg ttgacatatt caaccccaaa tatgattgta aaattatgac ttcaaaaaca  1200
gatgtaagca gctccgttat cacatctcta ggagccattg tgtcatgcta tggcaaaact  1260
aaatgtacag catccaataa aaatcgtgga atcataaaga cattttctaa cgggtgcgat  1320
tatgtatcaa ataaagggat ggacactgtg tctgtaggta acacattata ttatgtaaat  1380
aagcaagaag gtaaaagtct ctatgtaaaa ggtgaaccaa taataaattt ctatgaccca  1440
ttagtattcc cctctgatga atttgatgca tcaatatctc aagtcaacga gaagattaac  1500
cagagcctag catttattcg taaatccgat gaattattac ataatgtaaa tgctggtaaa  1560
tccaccacaa atatcatgat aactactata attatagtga ttatagtaat attgttatca  1620
ttaattgctg ttggactgct cttatactgt aaggccagaa gcacaccagt cacactaagc  1680
aaagatcaac tgagtggtat aaataatatt gcatttagta actaa                  1725
```

```
SEQ ID NO: 2            moltype = AA   length = 574
FEATURE                 Location/Qualifiers
source                  1..574
                        mol_type = protein
                        organism = Respiratory syncytial virus
SEQUENCE: 2
MELLILKANA ITTILTAVTF CFASGQNITE EFYQSTCSAV SKGYLSALRT GWYTSVITIE    60
LSNIKENKCN GTDAKVKLIK QELDKYKNAV TELQLLMQST PPTNNRARRE LPRFMNYTLN   120
NAKKTNVTLS KKRKRRFLGF LLGVGSAIAS GVAVSKVLHL EGEVNKIKSA LLSTNKAVVS   180
LSNGVSVLTS KVLDLKNYID KQLLPIVNKQ SCSISNIETV IEFQQKNNRL LEITREFSVN   240
AGVTTPVSTY MLTNSELLSL INDMPITNDQ KKLMSNNVQI VRQQSYSIMS IIKEEVLAYV   300
VQLPLYGVID TPCWKLHTSP LCTTNTKEGS NICLTRTDRG WYCDNAGSVS FFPQAETCKV   360
QSNRVFCDTM NSLTLPSEIN LCNVDIFNPK YDCKIMTSKT DVSSSVITSL GAIVSCYGKT   420
KCTASNKNRG IIKTFSNGCD YVSNKGMDTV SVGNTLYYVN KQEGKSLYVK GEPIINFYDP   480
LVFPSDEFDA SISQVNEKIN QSLAFIRKSD ELLHNVNAGK STTNIMITTI IIVIIVILLS   540
LIAVGLLLYC KARSTPVTLS KDQLSGINNI AFSN                              574

SEQ ID NO: 3            moltype = DNA  length = 1725
FEATURE                 Location/Qualifiers
misc_feature            1..1725
                        note = F Protein 576
source                  1..1725
                        mol_type = other DNA
                        organism = synthetic construct
SEQUENCE: 3
atggagctgc tcatcttgaa ggctaacgcc attaccacta tccttacagc ggtgacgttc     60
tgctttgcat ccggtcagaa tattaccgaa gagttctacc aatctacttg tagcgctgtc   120
tcaaaaggct atctgtcggc cctccgtaca ggatggtaca cgagtgttat caccatcgaa   180
ttgtccaaca ttaaggagaa caagtgcaac ggtactgacg cgaaggtaaa gcttatcaaa   240
caggaactgg ataagtacaa gaacgcagtg acagagctcc aattgctgat gcagtctacc   300
cccgctacga ataaccgcgc taggagagaa cttccacgat tcatgaacta tactctcaat   360
aacgccaaaa agaccaacgt cacattgagc aaaaagcgta agcgcaggtt tctgggcttc   420
ctcctgggag ttggttcagc tattgcgtcg gcgtagccg tgagtaaagt ccttcacttg   480
gagggagaag ttaataagat caagtccgca ctcctgtcta ctaacaaagc tgtggtcagc   540
ttgtcaaacg gtgtatccgt gctgacctcg aaggttcttg acctcaaaaa ttacatcgat   600
aagcaattgc tgccgattgt caacaagcag agttgttcta tcagcaatat tgagacggtg   660
atcgagttcc aacagaaaaa caacagactc ctggaaatca cacgtgagtt ttcagtaaat   720
gccggcgtta ctaccccgt ctccacgtac atgcttacaa actcggaatt gctcagtctg   780
attaacgaca tgcctatcac taatgatcag aagaagctta tgtctaacaa cgtgcaaatt   840
gtccgccagc aaagctattc catcatgtca atcattaaag aggaagtgtt ggcgtacgta   900
gttcagctcc cactgtacgg agtcatcgac acccgtgct ggaagcttca tacctcgccc   960
ttgtgtacga caaatactaa agagggtct aacatttgcc tcaccaggac ggatcgaggc  1020
tggtattgcg ataacgctgg aagtgtgagc ttcttccctc aagcagaaac atgtaaggta  1080
cagtccaata gagttttttg cgacactatg aactcactga cccttccatc tgaggtcaat  1140
ttgtgtaacg tcgatatctt caacccgaag tacgactgca aaattatgac gtccaagaca  1200
gatgtgtcga gtagcgtaat cacttcactc ggtgccatcg tttcttgcta cggcaagacc  1260
aaatgtacgg cttccaataa gaaccgtgga attatcaaga cattctcaaa cggttgcgac  1320
tatgtcagca ataagggcgt ggacactgtg agtgtaggaa acaccctgta ctacgttaac  1380
aagcaagaag gtaaatcact gtatgtcaag ggcgagccca ttatcaattt ttacgatcct  1440
cttgtgttcc catccgacga gttcgatgcg tctatcagcc aggtaaacga aaagattaac  1500
cagtccttgg catttatccg caaatcggac gagctcctgc acaatgttaa cgccggaaag  1560
agtacgacaa acattatgat cactaccatc attatcgtca ttatcgtgat ccttttgtca  1620
ctcattgctg taggtctgct tttgtactgt aaagcgaggt ctacgcccgt tacactcagc  1680
aaggatcaac tgtccggcat caataacatt gccttctcga attaa                  1725

SEQ ID NO: 4            moltype = AA   length = 574
FEATURE                 Location/Qualifiers
REGION                  1..574
                        note = F Protein 576
source                  1..574
                        mol_type = protein
                        organism = synthetic construct
SEQUENCE: 4
MELLILKANA ITTILTAVTF CFASGQNITE EFYQSTCSAV SKGYLSALRT GWYTSVITIE    60
LSNIKENKCN GTDAKVKLIK QELDKYKNAV TELQLLMQST PATNNRARRE LPRFMNYTLN   120
NAKKTNVTLS KKRKRRFLGF LLGVGSAIAS GVAVSKVLHL EGEVNKIKSA LLSTNKAVVS   180
LSNGVSVLTS KVLDLKNYID KQLLPIVNKQ SCSISNIETV IEFQQKNNRL LEITREFSVN   240
AGVTTPVSTY MLTNSELLSL INDMPITNDQ KKLMSNNVQI VRQQSYSIMS IIKEEVLAYV   300
VQLPLYGVID TPCWKLHTSP LCTTNTKEGS NICLTRTDRG WYCDNAGSVS FFPQAETCKV   360
QSNRVFCDTM NSLTLPSEVN LCNVDIFNPK YDCKIMTSKT DVSSSVITSL GAIVSCYGKT   420
KCTASNKNRG IIKTFSNGCD YVSNKGVDTV SVGNTLYYVN KQEGKSLYVK GEPIINFYDP   480
LVFPSDEFDA SISQVNEKIN QSLAFIRKSD ELLHNVNAGK STTNIMITTI IIVIIVILLS   540
LIAVGLLLYC KARSTPVTLS KDQLSGINNI AFSN                              574

SEQ ID NO: 5            moltype = DNA  length = 1725
FEATURE                 Location/Qualifiers
misc_feature            1..1725
                        note = F Protein 541
source                  1..1725

```
                        mol_type = other DNA
                        organism = synthetic construct
SEQUENCE: 5
atggagctgc tcatcttgaa ggctaacgcc attaccacta tccttacagc ggtgacgttc    60
tgctttgcat ccggtcagaa tattaccgaa gagttctacc aatctacttg tagcgctgtc   120
tcaaaaggct atctgtcggc cctccgtaca ggatggtaca cgagtgttat caccatcgaa   180
ttgtccaaca ttaaggagaa caagtgcaac ggtactgacg cgaaggtaaa gcttatcaaa   240
caggaactgg ataagtacaa gaacgcagtg acagagctcc aattgctgat gcagtctacc   300
cccgctacga ataaccgcgc taggagagaa cttccacgat tcatgaacta tactctcaat   360
aacgccaaaa agaccaacgt cacattgagc aaaaagcaga agcaacagtt tctgggcttc   420
ctcctgggag ttggttcagc tattgcgtcg ggcgtagccg tgagtaaagt ccttcacttg   480
gagggagaag ttaataagat caagtccgca ctcctgtcta ctaacaaagc tgtggtcagc   540
ttgtcaaacg gtgtatccgt gctgacctcg aaggttcttg acctcaaaaa ttacatcgat   600
aagcaattgc tgccgattgt caacaagcag agttgttcta tcagcaatat tgagacggtg   660
atcgagttcc aacagaaaaa caacagactc tggaaatcac acgtgagtt ttcagtaaat   720
gccggcgtta ctaccccgt ctccacgtac atgcttacaa actcggaatt gctcagtctg   780
attaacgaca tgcctatcac taatgatcag aagaagctta tgtctaacaa cgtgcaaatt   840
gtccgccagc aaagctattc catcatgtca atcattaaag aggaagtgtt ggcgtacgta   900
gttcagctcc cactgtacgg agtcatcgac accccgtgct ggaagcttca tacctcgccc   960
ttgtgtacga caaatactaa agagggttct aacatttgcc tcaccaggac ggatcgaggc  1020
tggtattgcg ataacgctgg aagtgtgagc ttcttccctc aagcagaaac atgtaaggta  1080
cagtccaata gagttttttg cgacactatg aactcactga cccttccatc tgaggtcaat  1140
ttgtgtaacg tcgatatctt caaccccgaag tacgactgca aaattatgac gtccaagaca  1200
gatgtgtcga gtagcgtaat cacttcactc ggtgccatcg tttcttgcta cggcaagacc  1260
aaaatgtacg cttccaataa gaaccgtgga attatcaaaa cattctcgaa cggttgcgac  1320
tatgtcagca ataagggcgt ggacactgtg agtgtaggaa acaccctgta ctacgttaac  1380
aagcaagaag gtaaatcact gtatgtcaag ggcgagccca ttcaatttt tacgatcct   1440
cttgtgttcc catccgacga gttcgatgcg tctatcagcc aggtaaacga aaagattaac  1500
cagtccttgg catttatccg caaatcggac gagctcctgc acaatgttaa cgccggaaag  1560
agtacgacaa acattatgat cactaccatc attatcgtaa ttatcgtgat cctttttgtca  1620
ctcattgctg taggtctgct ttttgtactgt aaagcgaggt ctacgccgt tacactcagc  1680
aaggatcaac tgtccggcat caataacatt gccttctcga attaa                  1725

SEQ ID NO: 6             moltype = AA   length = 574
FEATURE                  Location/Qualifiers
REGION                   1..574
                         note = F protein 541
source                   1..574
                         mol_type = protein
                         organism = synthetic construct
SEQUENCE: 6
MELLILKANA ITTILTAVTF CFASGQNITE EFYQSTCSAV SKGYLSALRT GWYTSVITIE    60
LSNIKENKCN GTDAKVKLIK QELDKYKNAV TELQLLMQST PATNNRARRE LPRFMNYTLN   120
NAKKTNVTLS KKQKQQFLGF LLGVGSAIAS GVAVSKVLHL EGEVNKIKSA LLSTNKAVVS   180
LSNGVSVLTS KVLDLKNYID KQLLPIVNKQ SCSISNIETV IEFQQKNNRL LEITREFSVN   240
AGVTTPVSTY MLTNSELLSL INDMPITNDQ KKLMSNNVQI VRQQSYSIMS IIKEEVLAYV   300
VQLPLYGVID TPCWKLHTSP LCTTNTKEGS NICLTRTDRG WYCDNAGSVS FFPQAETCKV   360
QSNRVFCDTM NSLTLPSEVN LCNVDIFNPK YDCKIMTSKT DVSSSVITSL GAIVSCYGKT   420
KCTASNKNRG IIKTFSNGCD YVSNKGVDTV SVGNTLYYVN KQEGKSLYVK GEPIINFYDP   480
LVFPSDEFDA SISQVNEKIN QSLAFIRKSD ELLHNVNAGK STTNIMITTI IIVIIVILLS   540
LIAVGLLLYC KARSTPVTLS KDQLSGINNI AFSN                              574

SEQ ID NO: 7             moltype = DNA   length = 1695
FEATURE                  Location/Qualifiers
misc_feature             1..1695
                         note = F Protein 683
source                   1..1695
                         mol_type = other DNA
                         organism = synthetic construct
SEQUENCE: 7
atggagctgc tcatcttgaa ggctaacgcc attaccacta tccttacagc ggtgacgttc    60
tgctttgcat ccggtcagaa tattaccgaa gagttctacc aatctacttg tagcgctgtc   120
tcaaaaggct atctgtcggc cctccgtaca ggatggtaca cgagtgttat caccatcgaa   180
ttgtccaaca ttaaggagaa caagtgcaac ggtactgacg cgaaggtaaa gcttatcaaa   240
caggaactgg ataagtacaa gaacgcagtg acagagctcc aattgctgat gcagtctacc   300
cccgctacga ataaccgcgc taggagagaa cttccacgat tcatgaacta tactctcaat   360
aacgccaaaa agaccaacgt cacattgagc aaaaagcaga agcaacaggc tattgcgtcg   420
ggcgtagccg tgagtaaagt ccttcacttg gagggagaag ttaataagat caagtccgca   480
ctcctgtcta ctaacaaagc tgtggtcagc ttgtcaaacg gtgtatccgt gctgacctcg   540
aaggttcttg acctcaaaaa ttacatcgat aagcaattgc tgccgattgt caacaagcag   600
agttgttcta tcagcaatat tgagacggtg atcgagttcc aacagaaaaa caacagactc   660
tggaaatcac acgtgagtt ttcagtaaat gccggcgtta ctaccccgt ctccacgtac    720
atgcttacaa actcggaatt gctcagtctg attaacgaca tgcctatcac taatgatcag   780
aagaagctta tgtctaacaa cgtgcaaatt gtccgccagc aaagctattc catcatgtca   840
atcattaaag aggaagtgtt ggcgtacgta gttcagctcc cactgtacgg agtcatcgac   900
accccgtgct ggaagcttca tacctcgccc ttgtgtacga caaatactaa agagggttct   960
aacatttgcc tcaccaggac ggatcgaggc tggtattgcg ataacgctgg aagtgtgagc  1020
ttcttccctc aagcagaaac atgtaaggta cagtccaata gagttttttg cgacactatg  1080
aactcactga cccttccatc tgaggtcaat ttgtgtaacg tcgatatctt caaccccgaag  1140
```

```
tacgactgca aaattatgac gtccaagaca gatgtgtcga gtagcgtaat cacttcactc  1200
ggtgccatcg tttcttgcta cggcaagacc aaatgtacgg cttccaataa gaaccgtgga  1260
attatcaaaa cattctcgaa cggttgcgac tatgtcagca ataagggcgt ggacactgtg  1320
agtgtaggaa cacccctgta ctacgttaac aagcaagaag gtaaatcact gtatgtcaag  1380
ggcgagccca ttatcaattt ttacgatcct cttgtgttcc catccgacga gttcgatgcg  1440
tctatcagcc aggtaaacga aaagattaac cagtccttgg catttatccg caaatcggac  1500
gagctcctgc acaatgttaa cgccggaaag agtacgacaa acattatgat cactaccatc  1560
attatcgtca ttatcgtgat ccttttgtca ctcattgctg taggtctgct tttgtactgt  1620
aaagcgaggt ctacgcccgt tacactcagc aaggatcaac tgtccggcat caataacatt  1680
gccttctcga attaa                                                    1695

SEQ ID NO: 8          moltype = AA  length = 564
FEATURE               Location/Qualifiers
REGION                1..564
                      note = F protein 683
source                1..564
                      mol_type = protein
                      organism = synthetic construct
SEQUENCE: 8
MELLILKANA ITTILTAVTF CFASGQNITE EFYQSTCSAV SKGYLSALRT GWYTSVITIE   60
LSNIKENKCN GTDAKVKLIK QELDKYKNAV TELQLLMQST PATNNRARRE LPRFMNYTLN  120
NAKKTNVTLS KKQKQQAIAS GVAVSKVLHL EGEVNKIKSA LLSTNKAVVS LSNGVSVLTS  180
KVLDLKNYID KQLLPIVNKQ SCSISNIETV IEFQQKNNRL LEITREFSVN AGVTTPVSTY  240
MLTNSELLSL INDMPITNDQ KKLMSNNVQI VRQQSYSIMS IIKEEVLAYV VQLPLYGVID  300
TPCWKLHTSP LCTTNTKEGS NICLTRTDRG WYCDNAGSVS FFPQAETCKV QSNRVFCDTM  360
NSLTLPSEVN LCNVDIFNPK YDCKIMTSKT DVSSSVITSL GAIVSCYGKT KCTASNKNRG  420
IIKTFSNGCD YVSNKGVDTV SVGNTLYYVN KQEGKSLYVK GEPIINFYDP LVFPSDEFDA  480
SISQVNEKIN QSLAFIRKSD ELLHNVNAGK STTNIMITTI IIVIIVILLS LIAVGLLLYC  540
KARSTPVTLS KDQLSGINNI AFSN                                         564

SEQ ID NO: 9          moltype = DNA  length = 1695
FEATURE               Location/Qualifiers
misc_feature          1..1695
                      note = F protein 622
source                1..1695
                      mol_type = other DNA
                      organism = synthetic construct
SEQUENCE: 9
atggagctgc tcatcttgaa ggctaacgcc attaccacta tccttacagc ggtgacgttc   60
tgctttgcat ccggtcagaa tattaccgaa gagttctacc aatctacttg tagcgctgtc  120
tcaaaaggct atctgtcggc cctccgtaca ggatggtaca cgagtgttat caccatcgaa  180
ttgtccaaca ttaaggagaa caagtgcaac ggtactgacg cgaaggtaaa gcttatcaaa  240
caggaactgg ataagtacaa gaacgcagtg acagagctcc aattgctgat gcagtctacc  300
cccgctacga ataaccgcgc taggagagaa cttccacgat tcatgaacta tactctcaat  360
aacgccaaaa agaccaacgt cacattgagc aaaaagcgta agcgcagggc tattgcgtcg  420
ggcgtagccg tgagtaaagt ccttcacttg gagggagaag ttaataagat caagtccgca  480
ctcctgtcta ctaacaaagc tgtggtcagc ttgtcaaacg gtgtatccgt gctgacctcg  540
aaggttcttg acctcaaaaa tcacatcgat aagcaattgc tgccgattgt caacaagcag  600
agttgttcta tcagcaatat tgagacggtg atcgagttcc aacagaaaaa caacagactc  660
ctggaaatca cacgtgagtt ttcagtaaat gccggcgtta ctaccccgt ctccacgtac  720
atgcttacaa actcggaatt gctcagtctg attaacgaca tgcctatcac taatgatcag  780
aagaagctta tgtctaacaa cgtgcaaatt gtccgccagc aaagctattc catcatgtca  840
atcattaaag aggaagtgtt ggcgtacgta gttcagctcc cactgtacgg agtcatcgac  900
accccgtgct ggaagcttca tacctcgccc ttgtgtacga caaatactaa agagggttcc  960
aacatttgcc tcaccaggac ggatcgaggc tggtattgca ataacgctgg aagtgtgagc  1020
ttcttccctc aagcagaaac atgtaaggta cagtccaata gagttttttg cgacactatg  1080
aactcactga cccttccatc tgaggtcaat ttgtgtaacg tcgatatctt caacccgaag  1140
tacgactgca aaattatgac gtccaagaca gatgtgtcga gtagcgtaat cacttcactc  1200
ggtgccatcg tttcttgcta cggcaagacc aaatgtacgg cttccaataa gaaccgtgga  1260
attatcaaaa cattctcgaa cggttgcgac tatgtcagca ataagggcgt ggacactgtg  1320
agtgtaggaa cacccctgta ctacgttaac aagcaagaag gtaaatcact gtatgtcaag  1380
ggcgagccca ttatcaattt ttacgatcct cttgtgttcc catccgacga gttcgatgcg  1440
tctatcagcc aggtaaacga aaagattaac cagtccttgg catttatccg caaatcggac  1500
gagctcctgc acaatgttaa cgccggaaag agtacgacaa acattatgat cactaccatc  1560
attatcgtca ttatcgtgat ccttttgtca ctcattgctg taggtctgct tttgtactgt  1620
aaagcgaggt ctacgcccgt tacactcagc aaggatcaac tgtccggcat caataacatt  1680
gccttctcga attaa                                                    1695

SEQ ID NO: 10         moltype = AA  length = 564
FEATURE               Location/Qualifiers
REGION                1..564
                      note = F protein 622
source                1..564
                      mol_type = protein
                      organism = synthetic construct
SEQUENCE: 10
MELLILKANA ITTILTAVTF CFASGQNITE EFYQSTCSAV SKGYLSALRT GWYTSVITIE   60
LSNIKENKCN GTDAKVKLIK QELDKYKNAV TELQLLMQST PATNNRARRE LPRFMNYTLN  120
NAKKTNVTLS KKRKRRAIAS GVAVSKVLHL EGEVNKIKSA LLSTNKAVVS LSNGVSVLTS  180
```

```
KVLDLKNHID KQLLPIVNKQ SCSISNIETV IEFQQKNNRL LEITREFSVN AGVTTPVSTY    240
MLTNSELLSL INDMPITNDQ KKLMSNNVQI VRQQSYSIMS IIKEEVLAYV VQLPLYGVID    300
TPCWKLHTSP LCTTNTKEGS NICLTRTDRG WYCDNAGSVS FFPQAETCKV QSNRVFCDTM    360
NSLTLPSEVN LCNVDIFNPK YDCKIMTSKT DVSSSVITSL GAIVSCYGKT KCTASNKNRG    420
IIKTFSNGCD YVSNKGVDTV SVGNTLYYVN KQEGKSLYVK GEPIINFYDP LVFPSDEFDA    480
SISQVNEKIN QSLAFIRKSD ELLHNVAGK STTNIMITTI IIVIIVILLS LIAVGLLLYC     540
KARSTPVTLS KDQLSGINNI AFSN                                          564

SEQ ID NO: 11            moltype = DNA  length = 771
FEATURE                  Location/Qualifiers
source                   1..771
                         mol_type = other DNA
                         organism = Bovine respiratory syncytial virus
SEQUENCE: 11
atggagacat acgtgaacaa actccatgaa ggatcaactt acacagctgc tgttcagtac     60
aatgtcatag aaaaagatga tgatcctgca tctctcacaa tatgggttcc tatgttccaa    120
tcatccatct ctgctgattt gcttataaaa gaactaatca atgtgaacat attagttcga    180
caaatttcta ctctgaaagg tccttcattg aagattatga taaactcaag aagtgctgta    240
ctagcccaaa tgcccagcaa atttaccata agtgcaaatg tatcattgga tgaacgaagc    300
aaattagcat atgacataac tactccttgt gaaattaagg cttgtagttt aacatgttta    360
aaggtgaaaa atatgctcac aactgtgaaa gatctcacca tgaaaacatt caatcctacc    420
catgagatca ttgcactgtg tgaatttgaa aatatcatga gtacaaaag agttgttata    480
ccaactttct taaggtcaat caatgtaaaa gcaaaggatt tggactcact agagaatata    540
gctaccacag agttcaaaaa tgccatcact aatgctaaaa ttatacctta tgctgggttg    600
gtattagtta tcactgtaac tgacaataaa ggggcattca gtacattaa accacaaagt    660
caatttatag tagatcttgg tgcatatcta gagaaagaga gcatatatta tgtaactaca    720
aattggaaac acacggccac taaattctcc attaagccta tagaggactg a             771

SEQ ID NO: 12            moltype = AA  length = 256
FEATURE                  Location/Qualifiers
source                   1..256
                         mol_type = protein
                         organism = Bovine respiratory syncytial virus
SEQUENCE: 12
METYVNKLHE GSTYTAAVQY NVIEKDDDPA SLTIWVPMFQ SSISADLLIK ELINVNILVR     60
QISTLKGPSL KIMINSRSAV LAQMPSKFTI SANVSLDERS KLAYDITTPC EIKACSLTCL    120
KVKNMLTTVK DLTMKTFNPT HEIIALCEFE NIMTSKRVVI PTFLRSINVK AKDLDSLENI    180
ATTEFKNAIT NAKIIPYAGL VLVITVTDNK GAFKYIKPQS QFIVDLGAYL EKESIYYVTT    240
NWKHTATKFS IKPIED                                                    256

SEQ ID NO: 13            moltype = DNA  length = 771
FEATURE                  Location/Qualifiers
misc_feature             1..771
                         note = Codon Optimized Bovine RSV M
source                   1..771
                         mol_type = other DNA
                         organism = synthetic construct
SEQUENCE: 13
atggagactt acgtgaacaa gctgcacgag ggttccacct acaccgctgc tgtgcagtac     60
aacgtgatcg agaaggacga cgaccccgct tccctgacca tctgggtgcc catgttccag    120
tcctccatct ccgctgacct gctgatcaag gagctgatca acgtcaacat cctcgtgcgt    180
cagatctcca ccctgaaggg tccagcctg aagatcatga tcaactcccg ttccgctgtg    240
ctggctcaga tgccctccaa gttcaccatc tccgccaacg tgtccctgga cgagcgttcc    300
aagctggctt acgacatcac cacccccctgc gagatcaagg cttgctccct gacctgcctg    360
aaggtcaaga acatgctgac caccgtgaag gacctgacca tgaagacctt caaccccacc    420
cacgagatca tcgctctgtg cgagttcgag aacatcatga cctccaagcg tgtggtcatc    480
cccaccttcc tccgctccat caacgtgaag gctaaggacc tggactccct cgagaacatc    540
gctaccaccg agttcaagaa cgctatcacc aacgctaaga tcatcccta cgctggcctg    600
gtgctggtca tcaccgtgac cgacaacaag ggcgctttca agtacatcaa gccccagtcc    660
cagttcatcg tggacctggg cgcttacctc gagaaggagt ccatctacta cgtcaccacc    720
aactggaagc acaccgctac caagttctcc atcaagccca tcgaggacta a             771

SEQ ID NO: 14            moltype = AA  length = 256
FEATURE                  Location/Qualifiers
REGION                   1..256
                         note = Codon Optimized Bovine RSV M
source                   1..256
                         mol_type = protein
                         organism = synthetic construct
SEQUENCE: 14
METYVNKLHE GSTYTAAVQY NVIEKDDDPA SLTIWVPMFQ SSISADLLIK ELINVNILVR     60
QISTLKGPSL KIMINSRSAV LAQMPSKFTI SANVSLDERS KLAYDITTPC EIKACSLTCL    120
KVKNMLTTVK DLTMKTFNPT HEIIALCEFE NIMTSKRVVI PTFLRSINVK AKDLDSLENI    180
ATTEFKNAIT NAKIIPYAGL VLVITVTDNK GAFKYIKPQS QFIVDLGAYL EKESIYYVTT    240
NWKHTATKFS IKPIED                                                    256

SEQ ID NO: 15            moltype = DNA  length = 1176
FEATURE                  Location/Qualifiers
source                   1..1176
```

```
                        mol_type = other DNA
                        organism = Respiratory syncytial virus
SEQUENCE: 15
atggctctta gcaaagtcaa gttgaatgat acactcaaca aagatcaact tctgtcatcc    60
agcaaataca ccatccaacg gagcacagga gatagtattg atactcctaa ttatgatgtg   120
cagaaacaca tcaataagtt atgtggcatg ttattaatca cagaagatgc taatcataaa   180
ttcactgggt taataggtat gttatatgcg atgtctaggt taggaagaga agacaccata   240
aaaatactca gagatgcggg atatcatgta aaagcaaatg gagtagatgt aacaacacat   300
cgtcaagaca ttaatggaaa agaaatgaaa tttgaagtgt taacattggc aagcttaaca   360
actgaaattc aaatcaacat tgagatagaa tctagaaaat cctacaaaaa aatgctaaaa   420
gaaatgggag aggtagctcc agaatacagg catgactctc ctgattgtgg gatgataata   480
ttatgtatag cagcattagt aataactaaa ttagcagcag ggacagatc tggtcttaca    540
gccgtgatta ggagagctaa taatgtccta aaaatgaaa tgaaacgtta caaaggctta    600
ctacccaagg acatagccaa cagcttctat gaagtgtttg aaaaacatcc ccactttata   660
gatgtttttg ttcatttggg tatagcacaa tcttctacca gaggtggcag tagagttgaa   720
gggattttg caggattgtt tatgaatgcc tatggtgcag gcaagtgat gttacggtgg     780
ggagtcttag caaaatcagt taaaaatatt atgttaggac atgctagtgt gcaagcagaa   840
atggaacaag ttgttgaggt ttatgaatat gcccaaaaat tgggtggtga agcaggattc   900
taccatatat tgaacaaccc aaaagcatca ttattatctt tgactcaatt tcctcacttc   960
tccagtgtag tattaggcaa tgctgctggc ctaggcataa tgggagagta cagaggtaca  1020
ccgaggaatc aagatctata tgatgcagca aaggcatatg ctgaacaact caagaaaat  1080
ggtgtgatta actacagtgt actagacttg acagcagaag aactagaggc tatcaaacat  1140
cagcttaatc caaagataa tgatgtagag ctttga                             1176

SEQ ID NO: 16           moltype = AA   length = 391
FEATURE                 Location/Qualifiers
source                  1..391
                        mol_type = protein
                        organism = Respiratory syncytial virus
SEQUENCE: 16
MALSKVKLND TLNKDQLLSS SKYTIQRSTG DSIDTPNYDV QKHINKLCGM LLITEDANHK    60
FTGLIGMLYA MSRLGREDTI KILRDAGYHV KANGVDVTTH RQDINGKEMK FEVLTLASLT   120
TEIQINIEIE SRKSYKKMLK EMGEVAPEYR HDSPDCGMII LCIAALVITK LAAGDRSGLT   180
AVIRRANNVL KNEMKRYKGL LPKDIANSFY EVFEKHPHFI DVFVHFGIAQ SSTRGGSRVE   240
GIFAGLFMNA YGAGQVMLRW GVLAKSVKNI MLGHASVQAE MEQVVEVYEY AQKLGGEAGF   300
YHILNNPKAS LLSLTQFPHF SSVVLGNAAG LGIMGEYRGT PRNQDLYDAA KAYAEQLKEN   360
GVINYSVLDL TAEELEAIKH QLNPKDNDVE L                                  391

SEQ ID NO: 17           moltype = DNA   length = 1176
FEATURE                 Location/Qualifiers
misc_feature            1..1176
                        note = Codon Optimized RSV N
source                  1..1176
                        mol_type = other DNA
                        organism = synthetic construct
SEQUENCE: 17
atggctctgt ccaaggtcaa gctgaacgac accctgaaca aggaccagct gctgtcctcc    60
tccaagtaca ccatccagcg gttccaccgg gactccatcg acacccccaa ctacgacgtg   120
cagaagcaca tcaacaagct gtgcggcatg ctgctgatca ccgaggacgc taaccacaag   180
ttcaccggtc tgatcggcat gctgtacgct atgtcccgtc tgggtcgtga ggacaccatc   240
aagatcctgc gtgacgctgg ttaccacgtg aaggctaacg gtgtcgacgt gaccacccac   300
cgtcaggaca tcaacggcaa ggagatgaag ttcgaggtcc tgaccctggc ttccctgacc   360
accgagatcc agatcaacat cgagatcgag tcccgtaagt cctacaagaa gatgctgaag   420
gagatgggcg aggtcgcccc cgagtaccgt cacgactccc ccgactgcgg catgatcatc   480
ctgtgcatcg ctgctctcgt catcaccaag ctggctgctg gtgaccgttc cggtctgacc   540
gctgtgatcc gtcgtgctaa caacgtgctg aagaacgaga tgaagcgcta caagggtctg   600
ctgcccaagg acatcgctaa cagcttctac gaggtgttcg agaagcaccc ccacttcatc   660
gacgtgttcg tgcacttcgg tatcgctcag tcctccaccc gtggtggttc ccgtgtggag   720
ggcatcttcg ctggtctgtt catgaacgct tacggtgctg gccaggtcat gctgcgttgg   780
ggtgtgctgg ctaagtccgt gaagaacatc atgctgggtc acgcttccgt gcaggctgag   840
atggagcagg tggtggaggt gtacgagtac gctcagaagc tgggcggcga ggctggtttc   900
taccacatct tgaacaaccc caaggcttcc ctgctgtccc tgacccagtt cccccacttc   960
tcctccgtgg tgctgggtaa cgctgctggt ctgggtatca tgggcgagta ccgtggcacc  1020
ccccgtaacc aggacctgta cgacgctgct aaggcttacg ccgagcagct caaggagaac  1080
ggcgtcatca actactccgt gctggacctg accgctgagg agctggaggc tatcaagcac  1140
cagctgaacc ccaagacaa cgacgtggag ctgtaa                             1176

SEQ ID NO: 18           moltype = AA   length = 391
FEATURE                 Location/Qualifiers
REGION                  1..391
                        note = Codon Optimized RSV N
source                  1..391
                        mol_type = protein
                        organism = synthetic construct
SEQUENCE: 18
MALSKVKLND TLNKDQLLSS SKYTIQRSTG DSIDTPNYDV QKHINKLCGM LLITEDANHK    60
FTGLIGMLYA MSRLGREDTI KILRDAGYHV KANGVDVTTH RQDINGKEMK FEVLTLASLT   120
TEIQINIEIE SRKSYKKMLK EMGEVAPEYR HDSPDCGMII LCIAALVITK LAAGDRSGLT   180
AVIRRANNVL KNEMKRYKGL LPKDIANSFY EVFEKHPHFI DVFVHFGIAQ SSTRGGSRVE   240
```

```
GIFAGLFMNA YGAGQVMLRW GVLAKSVKNI MLGHASVQAE MEQVVEVYEY AQKLGGEAGF    300
YHILNNPKAS LLSLTQFPHF SSVVLGNAAG LGIMGEYRGT PRNQDLYDAA KAYAEQLKEN    360
GVINYSVLDL TAEELEAIKH QLNPKDNDVE L                                  391

SEQ ID NO: 19           moltype = DNA   length = 1725
FEATURE                 Location/Qualifiers
misc_feature            1..1725
                        note = F protein 368
source                  1..1725
                        mol_type = other DNA
                        organism = synthetic construct
SEQUENCE: 19
atggagctgc tcatcttgaa ggctaacgcc attaccacta tccttacagc ggtgacgttc     60
tgctttgcat ccggtcagaa tattaccgaa gagttctacc aatctacttg tagcgctgtc    120
tcaaaaggct atctatcggc cttacgtaca ggatggtaca cgagtgttat caccatcgaa    180
ctgtccaaca ttaaggagaa taaatgcaac ggtactgacg cgaaggtaaa gctcatcaaa    240
caggaattgg ataagtacaa gaacgcagtg acagagcttc aactgctaat gcagtctacc    300
ccccctacga ataaccgcgc taggagagaa ctcccacgat tcatgaacta tactttaaat    360
aacgccaaaa agaccaacgt cacattgagc aaaaagcgta agcgcaggtt tctgggcttc    420
cttctcggag ttggttcagc tattgcgtcg ggcgtagccg tgagtaaagt cttgcacctg    480
gagggagaag ttaataagat caagtccgca ctcctgtcta ctaacaaagc tgtggtcagc    540
ctatcaaacg gtgtatccgt gttaacctcg aaggttctgg acttgaaaaa ttacatcgat    600
aagcaactcc tgccgattgt caacaagcag agttgttcta tcagcaatat tgagacggtg    660
atcgagttcc aacagaaaaa caacagattg ctggaaatca cacgtgagtt ttcagtaaat    720
gccggcgtta ctaccccgt ctccacgtac atgctaacaa actcggaatt acttagtctc    780
attaacgaca tgcctatcac taatgatcag aagaagttga tgtctaacaa cgtgcaaatt    840
gtccgccagc aaagctattc catcatgtca atcattaaag aggaagtgct ggcgtacgta    900
gttcagctcc cactgtacgg agtcatcgac acccgtgct ggaagctaca tacctcgccc    960
ttatgtacga caaatactaa agagggtct aacatttgcc ttaccaggac ggatcgaggc    1020
tggtattgcg ataacgctgg aagtgtgagc ttcttccctc aagcagaaac atgtaaggta    1080
cagtccaata gagttttttg cgacactatg aactcattga ccctcccatc tgagatcaat    1140
ctgtgtaacg tcgatatctt caacccgaag tacgactgca aaattatgac gtccaagaca    1200
gatgtgtcga gtagcgtaat cacttcacta ggtgccatcg tttcttgcta cggcaagacc    1260
aaatgtcagca cttccaataa gaaccgtgga attatcaaga cattctcgaa cggttgcgac    1320
tatgtcagca ataagggcat ggacactgtg agtgtaggaa acaccttata ctacgttaac    1380
aagcaagaag gtaaatcact ttatgtcaag ggcgagccca ttcaattt ttacgatcct    1440
ttggtgttcc catccgacga gttcgatgcg tctatcagcc aggtaaacga aaagattaac    1500
cagtccctcg catttatccg caaatcggac gagctgctac acaatgttaa cgccggaaag    1560
agtacgacaa acattatgat cactaccatc attatcgtaa ttatcgtgat cctttttgtca    1620
ctcattgctg taggtctgtt actatactgt aaagcgaggt ctacgcccgt tacacttagc    1680
aaggatcaat tgtccggcat caataacatt gccttctcga attaa               1725

SEQ ID NO: 20           moltype = AA   length = 574
FEATURE                 Location/Qualifiers
REGION                  1..574
                        note = F protein 368
source                  1..574
                        mol_type = protein
                        organism = synthetic construct
SEQUENCE: 20
MELLILKANA ITTILTAVTF CFASGQNITE EFYQSTCSAV SKGYLSALRT GWYTSVITIE     60
LSNIKENKCN GTDAKVKLIK QELDKYKNAV TELQLLMQST PPTNNRARRE LPRFMNYTLN    120
NAKKTNVTLS KKRKRRFLGF LLGVGSAIAS GVAVSKVLHL EGEVNKIKSA LLSTNKAVVS    180
LSNGVSVLTS KVLDLKNYID KQLLPIVNKQ SCSISNIETV IEFQQKNNRL LEITREFSVN    240
AGVTTPVSTY MLTNSELLSL INDMPITNDQ KKLMSNNVQI VRQQSYSIMS IIKEEVLAYV    300
VQLPLYGVID TPCWKLHTSP LCTTNTKEGS NICLTRTDRG WYCDNAGSVS FFPQAETCKV    360
QSNRVFCDTM NSLTLPSEIN LCNVDIFNPK YDCKIMTSKT DVSSSVITSL GAIVSCYGKT    420
KCTASNKNRG IIKTFSNGCD YVSNKGMDTV SVGNTLYYVN KQEGKSLYVK GEPIINFYDP    480
LVFPSDEFDA SISQVNEKIN QSLAFIRKSD ELLHNVNAGK STTNIMITTI IIVIIVILLS    540
LIAVGLLLYC KARSTPVTLS KDQLSGINNI AFSN                                574

SEQ ID NO: 21           moltype = AA   length = 560
FEATURE                 Location/Qualifiers
REGION                  1..560
                        note = F protein 623
source                  1..560
                        mol_type = protein
                        organism = synthetic construct
SEQUENCE: 21
MELLILKANA ITTILTAVTF CFASGQNITE EFYQSTCSAV SKGYLSALRT GWYTSVITIE     60
LSNIKENKCN GTDAKVKLIK QELDKYKNAV TELQLLMQST PATNNRANNE LPRFMNYTLN    120
NAKKTNVTLS RRAIASGVAV SKVLHLEGEV NKIKSALLST NKAVVSLSNG VSVLTSKVLD    180
LKNHIDKQLL PIVNKQSCSI SNIETVIEFQ QKNNRLLEIT REFSVNAGVT TPVSTYMLTN    240
SELLSLINDM PITNDQKKLM SNNVQIVRQQ SYSIMSIIKE EVLAYVVQLP LYGVIDTPCW    300
KLHTSPLCTT NTKEGSNICL TRTDRGWYCD NAGSVSFFPQ AETCKVQSNR VFCDTMNSLT    360
LPSEVNLCNV DIFNPKYDCK IMTSKTDVSS SVITSLGAIV SCYGKTKCTA SNKNRGIIKT    420
FSNGCDYVSN KGVDTSVGN TLYYVNKQEG KSLYVKGEPI INFYDPLVFP SDEFDASISQ    480
VNEKINQSLA FIRKSDELLH NVNAGKSTTN IMITTIIIVI IVILLSLIAV GLLLYCKARS    540
TPVTLSKDQL SGINNIAFSN                                                560
```

```
SEQ ID NO: 22          moltype = AA  length = 252
FEATURE                Location/Qualifiers
source                 1..252
                       mol_type = protein
                       organism = Avian influenza virus
SEQUENCE: 22
MSLLTEVETY VLSIIPSGPL KAEIAQKLED VFAGKNTDLE ALMEWLKTRP ILSPLTKGIL  60
GFVFTLTVPS ERGLQRRRFV QNALNGNGDP NNMDRAVKLY KKLKREITFH GAKEVSLSYS  120
TGALASCMGL IYNRMGTVTT EVAFGLVCAT CEQIADSQHR SHRQMATITN PLIRHENRMV  180
LASTTAKAME QMAGSSEQAA EAMEVANQAR QMVQAMRTIG THPNSSAGLR DNLLENLQAY  240
QKRMGVQMQR FK                                                      252

SEQ ID NO: 23          moltype = AA  length = 4
FEATURE                Location/Qualifiers
REGION                 1..4
                       note = Secondary Cleavage Site
source                 1..4
                       mol_type = protein
                       organism = synthetic construct
SEQUENCE: 23
RARR                                                               4

SEQ ID NO: 24          moltype = AA  length = 6
FEATURE                Location/Qualifiers
REGION                 1..6
                       note = Primary Cleavage Site
source                 1..6
                       mol_type = protein
                       organism = synthetic construct
SEQUENCE: 24
KKRKRR                                                             6

SEQ ID NO: 25          moltype = DNA  length = 897
FEATURE                Location/Qualifiers
misc_feature           1..897
                       note = Codon Optimized RSV G
source                 1..897
                       mol_type = other DNA
                       organism = synthetic construct
SEQUENCE: 25
atgtccaaga acaaagacca gcgtaccgct aagactctgg agcgcacatg ggatacgctc  60
aatcacttgc ttttcatctc tagctgcctg tacaaactca acttgaagtc agtggcccaa  120
attacccttt cgatcctggc gatgattatc agtacttccc tcatcattgc agctatcatt  180
tttatcgcct ctgcgaatca taaggtcaca cccacgaccg caatcattca ggacgctact  240
agccaaatca aaaacacaac ccctacgtat ttgactcaga acccacaact gggtatttca  300
ccgtcgaatc ccagtgaaat cacctcccag atcacaacta ttcttgcctc taccacgcct  360
ggcgttaaga gcacactcca atcaactacc gtaaagacga aaaacacaac taccacccag  420
acgcagccat ccaagccgac aactaaacaa aggcagaaca agcccccttc gaagccaaat  480
aacgatttcc acttcgaggt gtttaacttc gtcccgtgta gtatctgctc taataacccc  540
acctgttggg ctatttgcaa aagaatccct aacaagaagc caggaaaaaa gacgacaact  600
aaacccacca agaagcctac gttgaaaaca actaagaagg acccgaaacc acaaaccacg  660
aagagcaaag aagttcccac aactaagcct accgaggaac cgacgatcaa tacaactaag  720
accaacatta tcacgacact gctcacttca aataccactg gtaacccaga gctgacctcc  780
cagatggaaa ccttccattc gacgagttct gagggcaacc ccagcccttc ccaagtatca  840
acaacttcgg aatacccatc tcagcccagt agccctccga ataccccacg acaataa     897

SEQ ID NO: 26          moltype = AA  length = 298
FEATURE                Location/Qualifiers
REGION                 1..298
                       note = Codon Optimized RSV G
source                 1..298
                       mol_type = protein
                       organism = synthetic construct
SEQUENCE: 26
MSKNKDQRTA KTLERTWDTL NHLLFISSCL YKLNLKSVAQ ITLSILAMII STSLIIAAII  60
FIASANHKVT PTTAIIQDAT SQIKNTTPTY LTQNPQLGIS PSNPSEITSQ ITTILASTTP  120
GVKSTLQSTT VKTKNTTTTQ TQPSKPTTKQ RQNKPPSKPN NDFHFEVFNF VPCSICSNNP  180
TCWAICKRIP NKKPGKKTTT KPTKKPTLKT TKKDPKPQTT KSKEVPTTKP TEEPTINTTK  240
TNIITTLLTS NTTGNPELTS QMETFHSTSS EGNPSPSQVS TTSEYPSQPS SPPNTPRQ    298

SEQ ID NO: 27          moltype = AA  length = 65
FEATURE                Location/Qualifiers
source                 1..65
                       mol_type = protein
                       organism = Respiratory syncytial virus
SEQUENCE: 27
MGNTSITIEF TSKFWPYFTL IHMILTLISL LIIITIMIAI LNKLSEHKTF CNNTLELGQM  60
HQINT                                                              65

```
SEQ ID NO: 28             moltype = AA   length = 6
FEATURE                   Location/Qualifiers
REGION                    1..6
                          note = Furin Recognition Site Mutation
source                    1..6
                          mol_type = protein
                          organism = synthetic construct
SEQUENCE: 28
KKQKQQ                                                                    6

SEQ ID NO: 29             moltype = AA   length = 6
FEATURE                   Location/Qualifiers
REGION                    1..6
                          note = Furin Recognition Site Mutation
source                    1..6
                          mol_type = protein
                          organism = synthetic construct
SEQUENCE: 29
GRRQQR                                                                    6

SEQ ID NO: 30             moltype = AA   length = 9
FEATURE                   Location/Qualifiers
REGION                    1..9
                          note = Secondary Cleavage Site
source                    1..9
                          mol_type = protein
                          organism = synthetic construct
SEQUENCE: 30
NNRARRELP                                                                 9

SEQ ID NO: 31             moltype = AA   length = 11
FEATURE                   Location/Qualifiers
REGION                    1..11
                          note = Primary Cleavage Site
source                    1..11
                          mol_type = protein
                          organism = synthetic construct
SEQUENCE: 31
LSKKRKRRFL G                                                             11

SEQ ID NO: 32             moltype = AA   length = 6
FEATURE                   Location/Qualifiers
REGION                    1..6
                          note = Furin Recognition Site Mutation
source                    1..6
                          mol_type = protein
                          organism = synthetic construct
SEQUENCE: 32
KKQKRQ                                                                    6

SEQ ID NO: 33             moltype = AA   length = 4
FEATURE                   Location/Qualifiers
REGION                    1..4
                          note = Furin Recognition Site Mutation
source                    1..4
                          mol_type = protein
                          organism = synthetic construct
SEQUENCE: 33
RAQQ                                                                      4

SEQ ID NO: 34             moltype = AA   length = 4
FEATURE                   Location/Qualifiers
REGION                    1..4
                          note = Furin Recognition Site Mutation
source                    1..4
                          mol_type = protein
                          organism = synthetic construct
SEQUENCE: 34
RANN                                                                      4
```

```
SEQ ID NO: 35         moltype = AA  length = 11
FEATURE               Location/Qualifiers
REGION                1..11
                      note = RSV F protein containing a Furin recognition site
                      mutation
source                1..11
                      mol_type = protein
                      organism = synthetic construct
SEQUENCE: 35
LSKKQKQQFL G                                                              11
```